(12) United States Patent
Jung et al.

(10) Patent No.: US 11,730,009 B2
(45) Date of Patent: Aug. 15, 2023

(54) COMPOUND AND ORGANIC LIGHT-EMITTING ELEMENT COMPRISING SAME

(71) Applicant: LG Chem, Ltd., Seoul (KR)

(72) Inventors: Min Woo Jung, Daejeon (KR); Dong Hoon Lee, Daejeon (KR); Jungoh Huh, Daejeon (KR)

(73) Assignee: LG Chem, Ltd.

( * ) Notice: Subject to any disclaimer, the term of this patent is extended or adjusted under 35 U.S.C. 154(b) by 402 days.

(21) Appl. No.: 15/756,683

(22) PCT Filed: Sep. 23, 2016

(86) PCT No.: PCT/KR2016/010644
§ 371 (c)(1),
(2) Date: Mar. 1, 2018

(87) PCT Pub. No.: WO2017/052259
PCT Pub. Date: Mar. 30, 2017

(65) Prior Publication Data
US 2018/0254427 A1    Sep. 6, 2018

(30) Foreign Application Priority Data
Sep. 24, 2015  (KR) .................... 10-2015-0135775

(51) Int. Cl.
*C07D 251/12* (2006.01)
*C07D 251/24* (2006.01)
(Continued)

(52) U.S. Cl.
CPC ........... *H10K 50/12* (2023.02); *C07D 251/12* (2013.01); *C07D 251/24* (2013.01);
(Continued)

(58) Field of Classification Search
CPC ........ C09K 15/04; C09K 15/30; C09K 19/00; C09K 19/04; C09K 19/06; C09K 19/067;
(Continued)

(56) References Cited

U.S. PATENT DOCUMENTS 4,122,270 A * 10/1978 De Jonge ............. C07D 251/26
252/403
5,298,067 A * 3/1994 Valet .................... C08K 5/3492
106/506
(Continued)

FOREIGN PATENT DOCUMENTS

CN    1580095 A    2/2005
CN    102585186 A    7/2012
(Continued)

OTHER PUBLICATIONS

Huang, W.Y., and Huang, S.Y., 2010, Sterically Encumbered Fluorene-Based Poly(arylene ether)s Containing Spiro-Annulated Substituents on the Main Chain, Macromolecules, 43, 10355-10365 (Year: 2010).*
(Continued)

*Primary Examiner* — Sean M DeGuire
*Assistant Examiner* — Rachel Simbana
(74) *Attorney, Agent, or Firm* — Lerner David LLP

(57) ABSTRACT

The present specification relates to a compound and an organic light emitting device comprising the same.

18 Claims, 2 Drawing Sheets

(51) Int. Cl.

| | | |
|---|---|---|
| *C07D 401/10* | (2006.01) | |
| *C07D 401/12* | (2006.01) | |
| *C07D 403/10* | (2006.01) | |
| *C07D 403/12* | (2006.01) | |
| *C09K 11/06* | (2006.01) | |
| *H10K 50/00* | (2023.01) | |
| *H10K 50/12* | (2023.01) | |
| *H10K 50/15* | (2023.01) | |
| *H10K 50/16* | (2023.01) | |
| *H10K 50/17* | (2023.01) | |
| *H10K 50/18* | (2023.01) | |
| *H10K 50/81* | (2023.01) | |
| *H10K 50/82* | (2023.01) | |
| *H10K 85/60* | (2023.01) | |

(52) U.S. Cl.
CPC ......... *C07D 401/10* (2013.01); *C07D 401/12* (2013.01); *C07D 403/10* (2013.01); *C07D 403/12* (2013.01); *C09K 11/06* (2013.01); *H10K 50/00* (2023.02); *H10K 50/15* (2023.02); *H10K 50/16* (2023.02); *H10K 50/171* (2023.02); *H10K 50/18* (2023.02); *H10K 50/81* (2023.02); *H10K 50/82* (2023.02); *H10K 85/654* (2023.02)

(58) Field of Classification Search
CPC ...... C09K 19/08; C09K 19/32; C09K 19/322; C09K 19/34; C09K 19/3441; C09K 19/3444; C09K 19/345; C09K 19/3452; C09K 19/3455; C09K 19/3458; C09K 19/3472; C09K 19/3475; C09K 19/3804; C09K 19/3814; C09K 19/3823; C09K 19/3828; C09K 19/44; C09K 19/48; C09K 19/50; C09K 2019/327; C09K 2019/328; C09K 15/00; C09K 15/16; C09K 15/18; C09K 15/20; C09K 15/22; C09K 11/06; C09K 2211/1029; C09K 2211/1044; C09K 2211/1059; H01L 51/005; H01L 51/0052; H01L 51/0054; H01L 51/0059; H01L 51/5024; H01L 51/50; H01L 51/5056; H01L 51/5072; H01L 51/5092; H01L 51/5096; H01L 51/0067; H01L 51/5206; H01L 51/5221; H01L 51/0071; H01L 51/0072; H01L 51/0073; H01L 51/0074; H01L 51/0062; C07D 403/10; C07D 401/10; C07D 251/24; C07D 403/12; C07D 401/12; C07D 251/12; C07D 239/26; C07D 213/24; C07D 213/30; C07D 213/32; C07D 213/38; Y02E 10/549; H10K 85/652; H10K 85/654

See application file for complete search history.

(56) References Cited

U.S. PATENT DOCUMENTS

| | | | | |
|---|---|---|---|---|
| 5,888,422 | A * | 3/1999 | Manero | C07C 17/2632 252/299.62 |
| 6,352,791 | B1 * | 3/2002 | Fink | H01L 51/0067 428/917 |
| 6,821,643 | B1 | 11/2004 | Hu et al. | |
| 2005/0249972 | A1 * | 11/2005 | Hatwar | H01L 51/5265 428/690 |
| 2011/0087023 | A1 | 4/2011 | Kamimoto et al. | |
| 2012/0071496 | A1 | 3/2012 | Maechling et al. | |
| 2013/0204033 | A1 * | 8/2013 | Cheng | A61K 47/6829 562/443 |
| 2014/0103325 | A1 | 4/2014 | Shin et al. | |
| 2015/0340627 | A1 | 11/2015 | Jatsch et al. | |
| 2017/0271597 | A1 | 9/2017 | Miyata et al. | |

FOREIGN PATENT DOCUMENTS

| | | | | |
|---|---|---|---|---|
| EP | 0096657 | A2 * | 12/1983 | ........... C07D 409/04 |
| EP | 271195 | A * | 6/1988 | ........... C07D 251/24 |
| EP | 0434608 | A1 * | 6/1991 | ........... C07D 405/12 |
| EP | 0704437 | A2 * | 4/1996 | ........... C08K 5/3492 |
| GB | 1115303 | A | 5/1968 | |
| JP | H0689024 | A | 3/1994 | |
| JP | H07199462 | A | 8/1995 | |
| JP | H11514143 | A | 11/1999 | |
| JP | 2005186607 | A | 7/2005 | |
| JP | 2006131796 | A | 5/2006 | |
| JP | 2008242179 | A | 10/2008 | |
| JP | 2012517966 | A | 8/2012 | |
| JP | 2013145791 | A | 7/2013 | |
| KR | 20110016044 | A | 2/2011 | |
| KR | 20110026432 | A | 3/2011 | |
| KR | 101417285 | B1 | 7/2014 | |
| KR | 20150010016 | A | 1/2015 | |
| KR | 20160060572 | A | 5/2016 | |
| WO | WO-9507278 | A1 * | 3/1995 | ............. A01N 43/54 |
| WO | 2005047268 | A2 | 5/2005 | |
| WO | 2009148040 | A1 | 12/2009 | |
| WO | 2013086394 | A1 | 6/2013 | |
| WO | 2014106524 | A2 | 7/2014 | |
| WO | 2014121040 | A1 | 8/2014 | |
| WO | 2014121055 | A2 | 8/2014 | |
| WO | 2015009076 | A1 | 1/2015 | |
| WO | 2015175678 | A1 | 11/2015 | |
| WO | 2016017757 | A1 | 2/2016 | |
| WO | 2016116520 | A1 | 7/2016 | |
| WO | WO-2016116520 | A1 * | 7/2016 | ........... C07D 335/16 |
| WO | 2018021714 | A1 | 2/2018 | |

OTHER PUBLICATIONS

Itami, K.; Yamazaki, D.; Yoshida, Y., 2004, Pyrimidine-Core extended—Systems: General Synthesis and Interesting Fluorescent Properties, J. Am. Chem. Soc., 126, 15396-15397 (Year: 2004).*

Zong, L.; Liu, C.; Liu, R.; Wang, J.; Jian, X., 2014, Soluble and thermally stable copoly(phenyl-s-triazine)s containing both diphenylfluorene and phthalazinone units in the backbone, Polym. Bull., 71, 2641-2660 (Year: 2014).*

ROthmann, M.M.; Fuchs, E.; Schildknecht, C.; Langer, N.; Lennartz, C.; Munster, I.; Strohriegl, P., 2011, Designing a bipolar host material for blue phosphorescent OLEDs: Phenoxy-carbazole substituted triazine, Organic Electronics, 1192-1197. (Year: 2011).*

Fink, R.; Heischkel, Y.; Thelakkat, M.; Schmidt, H.W., 1998, Synthesis and Application of Dimeric 1,3,5-Triazine ethers as Hole-Blocking Materials in Electroluminescent Devices, Chem. Mater., 10, 3620-3625 (Year: 1998).*

WO-2016116520-A1—Translated (Year: 2016).*

Andreev, V.M.; Kharkova, G.M.; Fokin, E.P.; Khachaturyan, V.M., 1979, Stabilization of temperature-indicating polymer films, Izvestiya Sibirskogo Otdeleniya Akademii Nauk SSSR (2), 124-129 (Year: 1979).*

English Abstract—Andreev, V.M.; Kharkova, G.M.; Fokin, E.P.; Khachaturyan, V.M., 1979, Stabilization of temperature-indicating polymer films, Izvestiya Sibirskogo Otdeleniya Akademii Nauk SSSR (2), 124-129 (Year: 1979).*

Fink et al. (Fink, R.; Heischkel, Y.; Thellakkat, M.; Schmidt, H., 1998, Synthesis and Application of Dimeric 1,3,5-Triazine Ethers as Hole-Blocking Materials in Electroluminescent Devices, Chem. Mater. 10, 3620-3625) (Year: 1998).*

Bozic-Weber et al. (Bozic-Weber, B.; Constable, E.C.; Figgemeier, E.; Housecroft, C.E.; Kylberg, W., 2008, Evaluation of polynuclear dendrons as photosensitizers for dye-sensitized solar cells, Energy Environ. Sci., 2, 299-305) (Year: 2008).*

EP-0096657-A2—translation (Year: 1983).*

Zhou et al. (Zhou, L.; Kou, K.; Wang, Y., 2014, Synthesis of soluble and theramlly stable polyimides with phthalimide as pendent groups from pyridin-containing triamine, J. Mater. Sci., 49, 5141-5150 (Year: 2014).*

(56) References Cited

OTHER PUBLICATIONS

Murase, T. and Fujita, M., 2005, Highly Blue Luminescent Triazine-Amine Conjugated Oligomers, J. Org. Chem. 70, 9269-9278 (Year: 2005).*

Search report from International Application No. PCT/KR2016/010644, dated Jan. 3, 2017.

Shen, Jie, et al., "Synthesis and Properties of Hyperbranched Polyimides Derived from Novel Triamine with Prolonged Chain Segments." Journal of Polymer Science, Part A: Polymer Chemistry, vol. 51, Recieved: Dec. 10, 2012 Revised: Jan. 29, 2013; Accepted Feb. 1, 2013; Published online: Mar. 19, 2013, pp. 2425-2437.

Andreev, V.M. et al, Stabilization of temperature-indicating polymer films, Izvestiya Sibirskogo Otdeleniya Akademii Nauk SSSR, Seriya Tekhnicheskikh Nauk, 1979, (2), 124-129. (See attached statement for concise explanation of relevancy).

Bozic-Weber, B. et al, Evaluation of polynuclear dendrons as photosensitizers for dye-sensitized solar cells, Energy & Environmental Science, Jan. 2009, 2(3), 299-305.

Constable, E. C. et al, Metal-mediated synthesis of multidomain ligands—a new strategy for metallosupramolecular chemistry, Chemistry—A European Journal, 1995, 1(6), 360-367.

Japanese Office Action for Application No. 2018-507007 dated Apr. 16, 2019.

Katsuo Akagane, J.E.Laine, G.G.Allan, The Reaction of Cellulose Fiber with Novel Imidazolic Chelating Agents Using a Cyanuric Chloride and Application to Metal Ion Indicator Paper, Japan Tappi Journal, 1974, vol. 28, 4, 171-175 (Abstract in English).

Naseer, M. M. et al, Suzuki-Miyaura cross-coupling reaction of dichloro-heteroaromatics: synthesis of functionalized dinucleophilic fragments, Journal of the Chilean Chemical Society, Dec. 2014, 59(4), 2717-2720.

RN 300358-66-1 Registry, Database Registry [Online] Retrieved from STN, Oct. 30, 2000.

RN 330981-50-5 Registry, Database Registry [Online] Retrieved from STN, Apr. 12, 2001.

RN 418793-19-8 Registry, Database Registry [Online] Retrieved from STN, May 20, 2002.

RN 4688-08-8 Registry, Database Registry [Online] Retrieved from STN, Nov. 16, 1984.

RN 477856-74-9, 477862-18-3 Registry, Database Registry [Online] Retrieved from STN, Dec. 31, 2002.

RN 864431-67-4, 864431-78-7, 864431-86-7 Registry, Database Registry [Online] Retrieved from STN, Oct. 4, 2005.

RN 887440-07-5 Registry, Database Registry [Online] Retrieved from STN, Jun. 12, 2006.

Amutha et al., "Synthesis and Characterization of Pyridine and Anthracene Containing Bismaleimides, Bisnadimides and Polyaspartimides", Journal or Polymer Research, vol. 15, No. 6, Dec. 2008, pp. 487-499.

DATABASE PubChem: Compound Summary for CID 89991932, https://pubchem.ncbi.nlm.nih.gov/compound/89991932#section=Top, Feb. 13, 2015, 3 pages.

Extended European Search Report and Written Opinion for EP Application No. 16848984.7, dated Jul. 27, 2018.

Fink, et al., "Aromatic Ethers with 1,3,5-Triazine Units as Hole-Blocking/Electron-Transport Materials in LEDs", InOrganic Light-Emitting Materials and Devices, vol. 3148, Dec. 1997, pp. 194-201.

Fink, et al., "Synthesis and Application of Dimeric 1,3,5-Triazine Ethers as Hole-Blocking Materials in Electroluminescent Devices", Chemistry of Materials, vol. 10, No. 11, Nov. 1998, pp. 3620-3625.

Ma, et al., "Syntehsis of a New Aromatic Diacid Containing Pyridine Ring and Related Polybenzimidazole", Chinese Chemical Letters, vol. 21, No. 8, Aug. 2010, pp. 976-978.

Yan, et al., "Optical Transparency and Light Colour of Highly Soluble Fluorinated Polyimides Derived from a Novel Pyridine-Containing Diamine m, p-3FPAPP and Various Aromatic Dianhydrides", Designed Monomers and Polymers, vol. 14, No. 6, Jan. 2011, pp. 579-592.

Yan, et al., "Soluble Polyimides Based on a Novel Pyridine-Containing Diamine mp-PAPP and Various Aromatic Dianhydrides", Polymer Bulletin, vol. 66, No. 9, May 2011, pp. 1191-1206.

* cited by examiner

[FIG. 1]
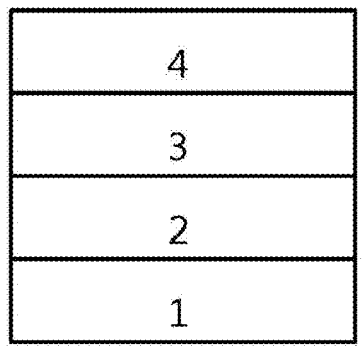
[FIG. 2]
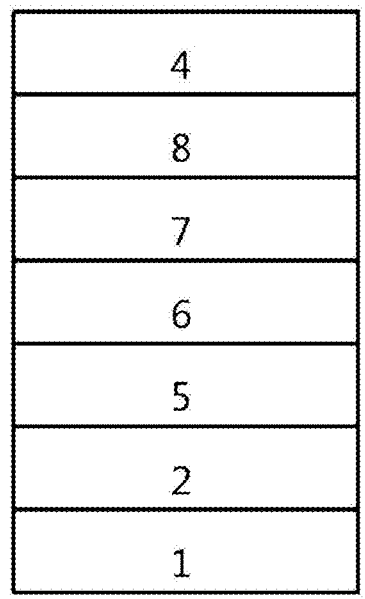

[FIG. 3]
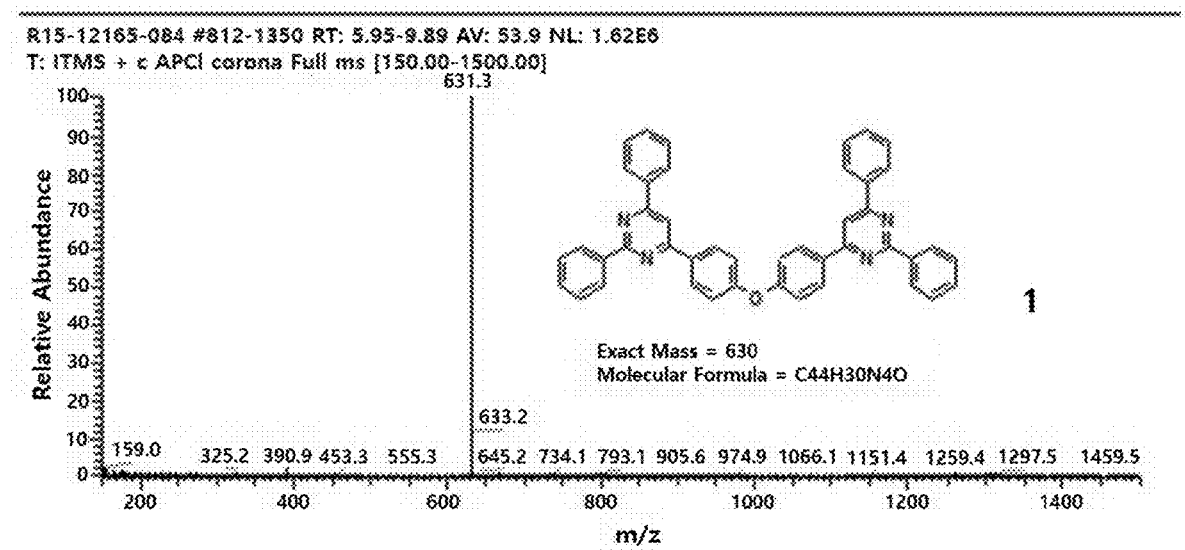
[FIG. 4]
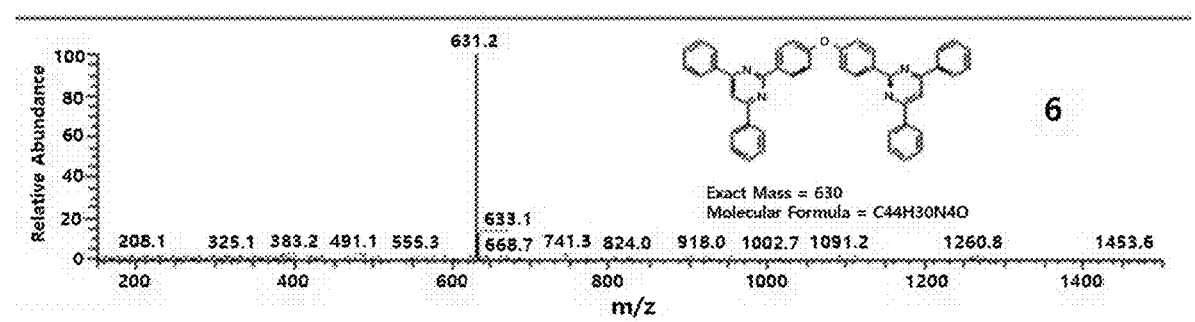

COMPOUND AND ORGANIC LIGHT-EMITTING ELEMENT COMPRISING SAME

CROSS-REFERENCE TO RELATED APPLICATIONS

The present application is a national phase entry under 35 U.S.C. § 371 of International Application No. PCT/KR2016/010644 filed on Sep. 23, 2016, which claims priority from Korean Patent Application No. 10-2015-0135775 filed in the Korean Intellectual Property Office on Sep. 24, 2015, the entire contents of which are incorporated herein by reference.

TECHNICAL FIELD

The present specification relates to a compound and an organic light emitting device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DISCLOSURE

Technical Problem

The present specification has been made in an effort to provide a compound and an organic light emitting device comprising the same.

Technical Solution

An exemplary embodiment of the present specification provides a compound represented by the following Chemical Formula 1.

[Chemical Formula 1]

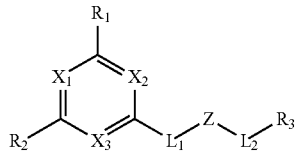

In Chemical Formula 1, at least one of $X_1$ to $X_3$ is N, and the others are the same as or different from each other, and are each independently N or CR, R is hydrogen; deuterium; a halogen group; a cyano group; a nitro group; a substituted or unsubstituted aryl group, or a substituted or unsubstituted heteroaryl group comprising one or more of N, O, and S atoms, Z is O, S, Se, or Te, $L_1$ is a direct bond; a substituted or unsubstituted arylene group; or a substituted or unsubstituted heteroarylene group comprising one or more of N, O, and S atoms, $L_2$ is a substituted or unsubstituted arylene group; or a substituted or unsubstituted heteroarylene group comprising one or more of N, O, and S atoms, $R_1$ and $R_2$ are the same as or different from each other, and are each independently a halogen group; a cyano group; a nitro group; a substituted or unsubstituted alkyl group; a substituted or unsubstituted cycloalkyl group; a substituted or unsubstituted aryl group; or a substituted or unsubstituted heteroaryl group comprising one or more of N, O, and S atoms, and $R_3$ is a halogen group; a cyano group; a nitro group; a substituted or unsubstituted silyl group; a substituted or unsubstituted boron group; a substituted or unsubstituted alkyl group; a substituted or unsubstituted cycloalkyl group; a substituted or unsubstituted alkenyl group; a substituted or unsubstituted aralkyl group; a substituted or unsubstituted aralkenyl group; a substituted or unsubstituted aryl group; a substituted or unsubstituted alkylaryl group; a substituted or unsubstituted arylphosphine group; a substituted or unsubstituted phosphine oxide group; a substituted or unsubstituted amine group; a substituted or unsubstituted alkylamine group; a substituted or unsubstituted arylamine group; or a substituted or unsubstituted heteroaryl group comprising one or more of N, O, and S atoms.

Further, an exemplary embodiment of the present specification provides an organic electronic device comprising: a first electrode; a second electrode provided to face the first electrode; and one or more organic material layers provided between the first electrode and the second electrode, in which one or more layers of the organic material layers comprise the above-described compound.

Advantageous Effects

The compound described in the present specification may be used as a material for an organic material layer of an organic light emitting device. The compound according to at least one exemplary embodiment may improve the efficiency, achieve low driving voltage and/or improve lifetime characteristics in the organic light emitting device. In particular, the compound described in the present specification may be used as a material for hole injection, hole transport, hole injection and hole transport, light emission, electron transport, or electron injection.

DESCRIPTION OF DRAWINGS

FIG. 1 illustrates an example of an organic light emitting device in which a substrate (1), a positive electrode (2), a light emitting layer (3), and a negative electrode (4) are sequentially stacked.

FIG. 2 illustrates an example of an organic light emitting device composed of a substrate (1), a positive electrode (2), a hole injection layer (5), a hole transport layer (6), a light emitting layer (7), an electron transport layer (8), and a negative electrode (4).

FIG. 3 is a view illustrating MS data values of Compound 2.

FIG. 4 is a view illustrating MS data values of Compound 3.

1: Substrate
2: Positive electrode
3: Light emitting layer
4: Negative electrode
5: Hole injection layer
6: Hole transport layer
7: Electron transport layer
8: Electron injection layer

MODE FOR INVENTION

Hereinafter, the present specification will be described in more detail.

An exemplary embodiment of the present specification provides the compound represented by Chemical Formula 1.

According to an exemplary embodiment of the present specification, the compound represented by Chemical Formula 1 has the core structure, and thus has an advantage in that the feature of each core is maximized to maximize the lifetime through an effect of cutting off the feature and conjugation, which elements of each Z have. Further, a symmetric form of the compound represented by Chemical Formula 1 has characteristics in that Tg is enhanced, the stability is increased, and the light emitting efficiency and performance are enhanced as compared to an asymmetric form of the compound.

In the present specification,

means a bond linked to another substituent.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitrile group; a nitro group; an imide group; an amino group; a silyl group; a boron group; a hydroxy group; a carbonyl group; an alkyl group; a cycloalkyl group; an alkenyl group; an alkoxy group; an aryloxy group; an alkylthioxy group; an arylthioxy group; an aryl group; an aralkyl group; an aralkenyl group; an alkylaryl group; a heteroaryl group; an amine group; an alkylamine group; an aralkylamine group; a heteroarylamine group; an arylamine group; a phosphoryl group; an arylphosphine group; a phosphine oxide group; or a heteroaryl group including one or more of N, O, S, Se, and Si atoms or being substituted with a substituent to which two or more substituents are linked among the exemplified substituents, or having no substituent. For example, "the substituent to which two or more substituents are linked" may be a biphenyl group. That is, the biphenyl group may also be an aryl group, and may be interpreted as a substituent to which two phenyl groups are linked. The biphenyl group means a substituent to which two aryl groups are linked, but "the substituent to which two or more substituents are linked" may also be a substituent to which two or more different substituents are linked. For example, "the substituent to which two or more substituents are linked" may be a phenyl group substituted with a pyridyl group, which is a substituent to which the pyridyl group and the phenyl group are linked, or a phenyl group substituted with a quinolinyl group, which is a substituent to which the quinolinyl group and the phenyl group are linked, or a phenyl group substituted with a cyano group, which is a substituent to which the cyano group and the phenyl group are linked.

In the present specification, examples of a halogen group include fluorine, chlorine, bromine or iodine.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of a boron group include a trimethylboron group, a triethylboron group, a t-butyldimethylboron group, a triphenylboron group, a phenylboron group, and the like, but are not limited thereto.

In the present specification, an alkyl group may be straight-chained or branch-chained, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but preferably has 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, a phosphoryl group includes $P(=O)$ and is a substituent to which the P atom is directly linked as a radical, and is represented by $—P(=O)R_{102}R_{103}$, and $R_{102}$ and $R_{103}$ are the same as or different from each other, and may be each independently a substituent composed of at least one of hydrogen; deuterium; a halogen group; an alkyl group; an alkenyl group; an alkoxy group; a cycloalkyl group; an aryl group; and a heterocyclic group. For example, specific examples of a case where the phosphoryl group has an aryl group as a substitution product include a diphenylphosphoryl group, a phenylbiphenylphosphoryl group, a biphenylbiphenylphosphoryl group, a phenylterphenylphosphoryl group, a biphenylterphenylphosphoryl group, and the like, but are not limited thereto.

In the present specification, specific examples of the phosphine oxide group include a diphenylphosphine oxide group, dinaphthylphosphine oxide, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

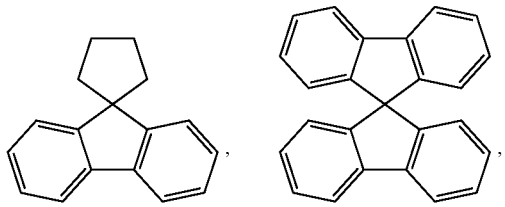

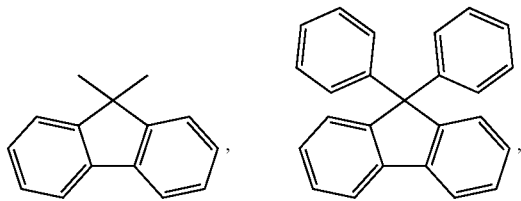

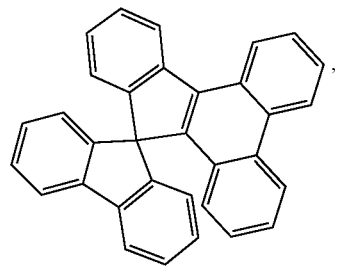

-continued

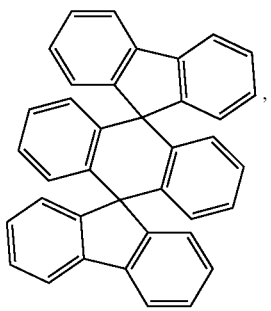

and the like. However, the fluorenyl group is not limited thereto.

In the present specification, a heteroaryl group includes one or more of an atom other than carbon, that is, a heteroatom, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of the heteroaryl group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a dibenzofuranyl group, and the like, but are not limited thereto.

In the present specification, the fused structure may be a structure in which an aromatic hydrocarbon ring is fused with the corresponding substituent.

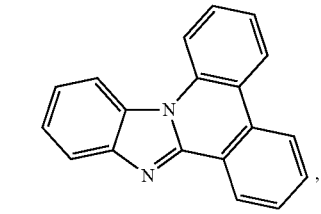

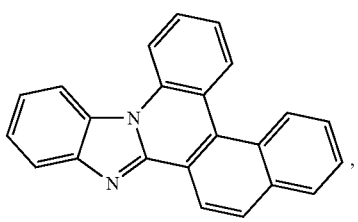

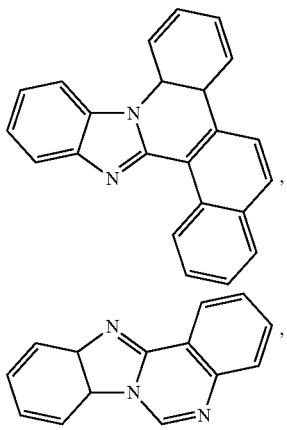

and the like, but are not limited thereto.

Examples of a fused ring of acridine include

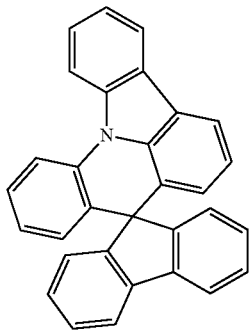 [SMILES: c1ccc2c(c1)-c1ccccc1C21c2ccccc2-n2c3ccccc3c3cccc1c32]

(spiro[fluorene-9,8'-indolo[3,2,1-de]acridine]), and the like, but are not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups combine with each other to form a ring means that adjacent groups combine with each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

In the present specification, an amine group means a monovalent amine in which at least one hydrogen atom of an amino group (—NH$_2$) is substituted with another substitution product, and is represented by —NR$_{100}$R$_{101}$, and R$_{100}$ and R$_{101}$ are the same as or different from each other, and may be each independently a substituent composed of at least one of hydrogen; deuterium; a halogen group; an alkyl group; an alkenyl group; an alkoxy group; a cycloalkyl group; an aryl group; and a heterocyclic group (however, at least one of R$_{100}$ and R$_{101}$ is not hydrogen). For example, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, the alkyl group in the alkylamine group, the N-alkylarylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, the heterocyclic group may be monocyclic or polycyclic, may be an aromatic ring, an aliphatic ring, or a fused ring of the aromatic ring and the aliphatic ring, and may be selected among the examples of the heteroaryl group.

In the present specification, the alkylene group means that there are two bonding positions in an alkyl group, that is, a divalent group. The above-described description on the alkyl group may be applied, except that the alkylene groups are each a divalent group.

In the present specification, the cycloalkylene group means that there are two bonding positions in a cycloalkyl group, that is, a divalent group. The above-described description on the cycloalkyl group may be applied, except that the cycloalkylene groups are each a divalent group.

In the present specification, the above-described description on the heteroaryl group may be applied to a heteroarylene except for a divalent heteroarylene group.

In the present specification, the above-described description on the aryl group may be applied to an aryl group in an aryloxy group, an aralkyl group, an aralkenyl group, and an alkylaryl group.

In the present specification, the above-described description on the alkyl group may be applied to an alkyl group in an aralkyl group and an alkylaryl group.

In the present specification, the above-described description on the aryl group may be applied to an arylene except for a divalent arylene group.

According to an exemplary embodiment of the present specification, at least one of $X_1$ to $X_3$ is N.

According to an exemplary embodiment of the present specification, $X_1$ to $X_3$ are the same as or different from each other, and are each independently N or CR.

According to an exemplary embodiment of the present specification, R is hydrogen, deuterium, a halogen group, a cyano group, a nitro group, a substituted or unsubstituted aryl group, or a substituted or unsubstituted heteroaryl group including one or more of N, O, and S atoms.

According to an exemplary embodiment of the present specification, R is an aryl group having 6 to 20 carbon atoms.

According to an exemplary embodiment of the present specification, R is a substituted or unsubstituted phenyl group, a substituted or unsubstituted biphenyl group, a substituted or unsubstituted terphenyl group, or a substituted or unsubstituted naphthyl group.

According to an exemplary embodiment of the present specification, R is a heteroaryl group having 6 to 30 carbon atoms, which includes one or more of N, O, and S atoms.

According to an exemplary embodiment of the present specification, R is hydrogen.

According to an exemplary embodiment of the present specification, Z is O, S, Se, or Te.

According to an exemplary embodiment of the present specification, Z is O or S.

According to an exemplary embodiment of the present specification, Z is O.

According to an exemplary embodiment of the present specification, Z is S.

According to an exemplary embodiment of the present specification, $L_1$ is a direct bond, or a substituted or unsubstituted arylene group, or a substituted or unsubstituted heteroarylene group comprising one or more of N, O, and S atoms.

According to an exemplary embodiment of the present specification, $L_2$ is a substituted or unsubstituted arylene group, or a substituted or unsubstituted heteroarylene group comprising one or more of N, O, and S atoms.

According to an exemplary embodiment of the present specification, $L_1$ or $L_2$ is a substituted or unsubstituted arylene group having 2 to 30 carbon atoms.

According to an exemplary embodiment of the present specification, $L_1$ or $L_2$ is a substituted or unsubstituted phenylene group, a substituted or unsubstituted biphenylene group, a substituted or unsubstituted terphenylene group, a substituted or unsubstituted naphthylene group, a substituted or unsubstituted anthracenyl group, or a substituted or unsubstituted fluorenylene group.

According to an exemplary embodiment of the present invention, $L_1$ or $L_2$ is a phenylene group, a biphenylene group, a terphenylene group, a naphthylene group, an anthracenyl group, or a fluorenylene group.

According to an exemplary embodiment of the present specification, $L_1$ is a direct bond, or a phenylene group or a biphenylene group.

According to an exemplary embodiment of the present specification, $L_2$ is a phenylene group or a biphenylene group.

According to an exemplary embodiment of the present specification, $R_1$ and $R_2$ are the same as or different from each other, and are each independently a halogen group; a cyano group; a nitro group; a substituted or unsubstituted alkyl group; a substituted or unsubstituted cycloalkyl group; a substituted or unsubstituted aryl group; or a substituted or unsubstituted heteroaryl group comprising one or more of N, O, and S atoms.

According to an exemplary embodiment of the present specification, $R_1$ and $R_2$ are the same as or different from each other, and are each independently an aryl group which is unsubstituted or substituted with a halogen group, a cyano group, a nitro group, an alkyl group, an alkenyl group, an alkoxy group, a cycloalkyl group, an aryl group, or a heteroaryl group comprising one or more of N, O, and S atoms.

According to an exemplary embodiment of the present specification, $R_1$ and $R_2$ are the same as or different from each other, and are a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted pyrenyl group, a substituted or unsubstituted perylenyl group, a substituted or unsubstituted chrysenyl group, or a substituted or unsubstituted fluorenyl group.

According to an exemplary embodiment of the present specification, $R_1$ and $R_2$ are the same as or different from each other, and are a substituted or unsubstituted phenyl group, a substituted or unsubstituted biphenyl group, a substituted or unsubstituted naphthyl group, or a substituted or unsubstituted fluorenyl group.

According to an exemplary embodiment of the present specification, $R_1$ and $R_2$ are the same as or different from each other, and are a phenyl group, a biphenyl group, a naphthyl group, or a fluorenyl group.

According to an exemplary embodiment of the present specification, $R_1$ and $R_2$ are the same as or different from each other, and are a phenyl group, a biphenyl group, or a naphthyl group.

According to an exemplary embodiment of the present specification, $R_3$ is a halogen group; a cyano group; a nitro group; a substituted or unsubstituted silyl group; a substituted or unsubstituted boron group; a substituted or unsubstituted alkyl group; a substituted or unsubstituted cycloalkyl group; a substituted or unsubstituted aryl group; a substituted or unsubstituted alkylaryl group; a substituted or unsubstituted arylphosphine group; a substituted or unsubstituted phosphine oxide group; a substituted or unsubstituted amine group; a substituted or unsubstituted alkylamine group; a substituted or unsubstituted arylamine group; or a substituted or unsubstituted heteroaryl group comprising one or more of N, O, and S atoms.

According to an exemplary embodiment of the present specification, $R_3$ is a substituted or unsubstituted pyridyl group, a substituted or unsubstituted pyrimidyl group, a substituted or unsubstituted triazinyl group, a substituted or unsubstituted acridyl group, a substituted or unsubstituted quinolinyl group, or a substituted or unsubstituted quinazolyl group.

According to an exemplary embodiment of the present specification, $R_3$ is a pyridyl group which is unsubstituted or substituted with a phenyl group, a biphenyl group, a terphenyl group or a naphthyl group, a pyrimidyl group, a triazinyl group which is unsubstituted or substituted with a phenyl group, an acridyl group, a quinolinyl group, or a quinazolyl group.

According to an exemplary embodiment of the present specification, $R_3$ is a triazinyl group which is unsubstituted or substituted with a pyridyl group, a pyrimidyl group, or a phenyl group, which is unsubstituted or substituted with a pyridyl group, a pyrimidyl group, or a triazinyl group.

According to an exemplary embodiment of the present specification, $R_3$ is a triazinyl group which is unsubstituted or substituted with a pyridyl group, a pyrimidyl group, or a phenyl group, which is unsubstituted or substituted with a cyano group, an alkyl group, a cycloalkyl group, or an alkoxy group.

According to an exemplary embodiment of the present specification, $R_3$ is a triazinyl group which is unsubstituted or substituted with a pyridyl group which is substituted with a methoxy group, a pyrimidyl group, or a phenyl group.

According to an exemplary embodiment of the present specification, $R_3$ is a substituted or unsubstituted carbazole group, a substituted or unsubstituted thiophene group, a substituted or unsubstituted furan group, a substituted or unsubstituted benzocarbazole group, a substituted or unsubstituted benzothiophene group, a substituted or unsubstituted benzofuran group, a substituted or unsubstituted dibenzocarbazole group, a substituted or unsubstituted dibenzothiophene group, or a substituted or unsubstituted dibenzofuran group.

According to an exemplary embodiment of the present specification, $R_3$ is a carbazole group, a thiophene group, a furan group, a benzocarbazole group, a benzothiophene group, a benzofuran group, a dibenzocarbazole group, a dibenzothiophene group, or a dibenzofuran group.

According to an exemplary embodiment of the present specification, $R_3$ is a phenyl group, a biphenyl group, a terphenyl group, a carbazole group in which a naphthyl group is substituted or unsubstituted, a thiophene group, a furan group, a benzocarbazole group, a benzothiophene group, a benzofuran group, a dibenzocarbazole group, a dibenzothiophene group, or a dibenzofuran group.

According to an exemplary embodiment of the present specification, $R_3$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted triphenyl group, a substituted or unsubstituted pyrenyl group, or a substituted or unsubstituted chrysenyl group, or a substituted or unsubstituted fluorenyl group.

According to an exemplary embodiment of the present specification, $R_3$ is a phenyl group, a biphenyl group, a terphenyl group, a naphthyl group, an anthracenyl group, a pyrenyl group, a chrysenyl group, or a fluorenyl group.

According to an exemplary embodiment of the present specification, $R_3$ is a pyridyl group, a pyrimidyl group, or a phenyl group which is unsubstituted or substituted with a triazinyl group, a quinolinyl group, or a quinazolyl group, a biphenyl group, a terphenyl group, a naphthyl group, an anthracenyl group, a phenanthryl group, a triphenyl group, or a fluorenyl group.

According to an exemplary embodiment of the present specification, $R_3$ is a phenyl group, a biphenyl group, a terphenyl group, a naphthyl group, an anthracenyl group, a chrysenyl group, spirobifluorene, triphenylene, or a fluorenyl group, which is unsubstituted or substituted with a phenyl group, a biphenyl group, a terphenyl group, or a naphthyl group.

According to an exemplary embodiment of the present specification, $R_3$ is a phenyl group, a biphenyl group, a terphenyl group, or a naphthyl group, in which a cyano group is substituted or unsubstituted.

According to an exemplary embodiment of the present specification, $R_3$ is a phenyl group, a biphenyl group, a terphenyl group, or a naphthyl group, in which benzonitrile is substituted or unsubstituted.

According to an exemplary embodiment of the present specification, $R_3$ is a substituted or unsubstituted phosphine oxide group.

According to an exemplary embodiment of the present specification, $R_3$ is a phosphine oxide group in which a phenyl group, a biphenyl group, or a naphthyl group is substituted or unsubstituted.

According to an exemplary embodiment of the present specification, $R_3$ is an oxadiazole group or a thiadiazolyl group, in which a phenyl group, a biphenyl group, or a naphthyl group is substituted or unsubstituted.

According to an exemplary embodiment of the present specification, $R_3$ is a substituted or unsubstituted tetraphenylsilyl.

According to an exemplary embodiment of the present specification, $R_3$ is a substituted or unsubstituted tetraphenylmethane.

According to an exemplary embodiment of the present specification, $R_3$ is a substituted or unsubstituted dibenzosilole.

According to an exemplary embodiment of the present specification, $R_3$ is substituted or unsubstituted

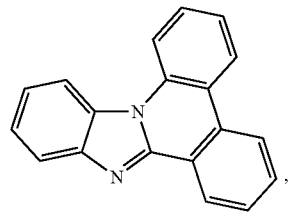 [SMILES: c1ccc2c(c1)nc1c3ccccc3c3ccccc3n21]

substituted or unsubstituted

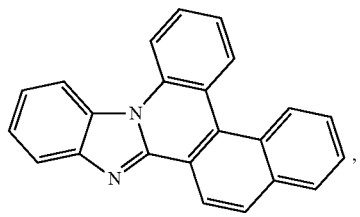 [SMILES: c1ccc2c(c1)ccc1c2c2ccccc2n2c3ccccc3nc12]

substituted or unsubstituted

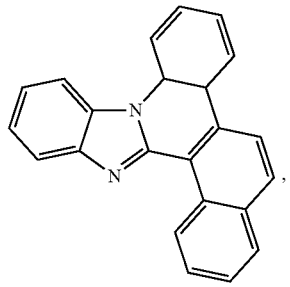 [SMILES: C1=CC2c3ccc4ccccc4c3-c3nc4ccccc4n3C2C=C1]

substituted or unsubstituted

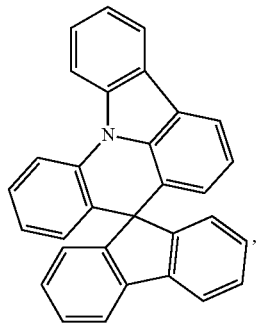 [SMILES: c1ccc2c(c1)-c1ccccc1C21c2ccccc2-n2c3ccccc3c3cccc1c32]

or substituted or unsubstituted

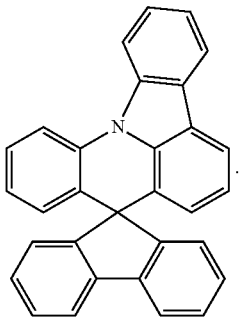 [SMILES: c1ccc2c(c1)-c1ccccc1C21c2ccccc2-n2c3ccccc3c3cccc1c32]

According to an exemplary embodiment of the present specification, $R_3$ is a substituted or unsubstituted spirobifluorene.

According to an exemplary embodiment of the present specification, $R_3$ is a substituted or unsubstituted acridine.

According to an exemplary embodiment of the present specification, Chemical Formula 1 may be represented by the following structures, but is not limited thereto.

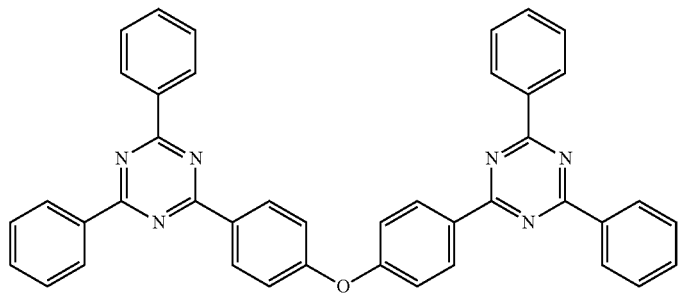

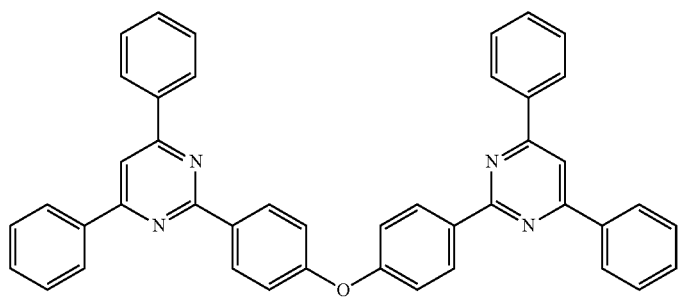

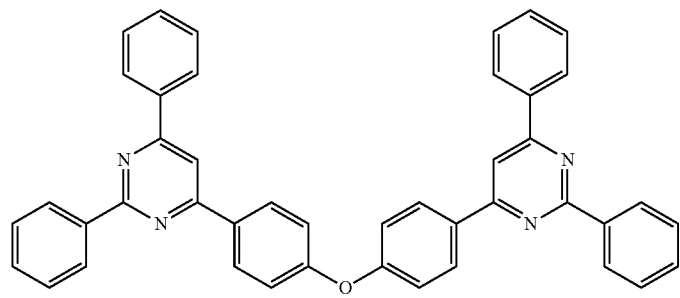
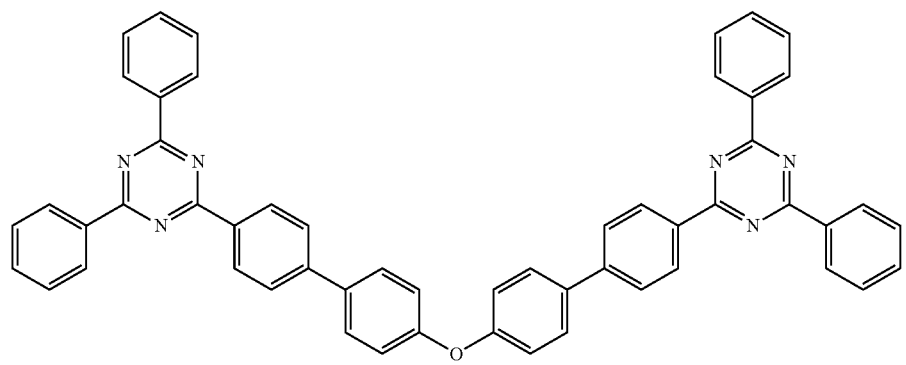
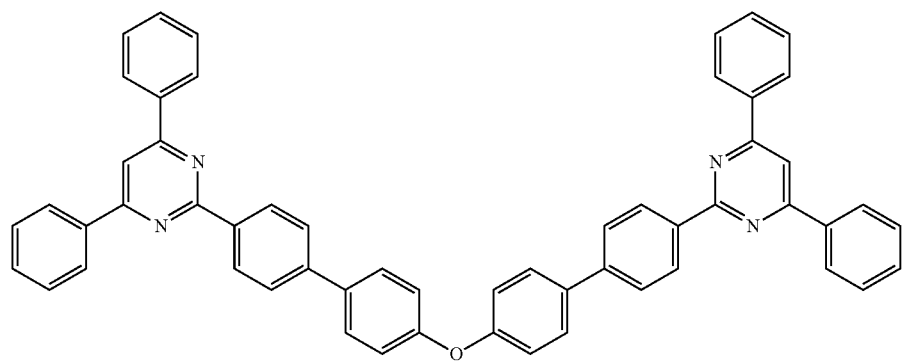
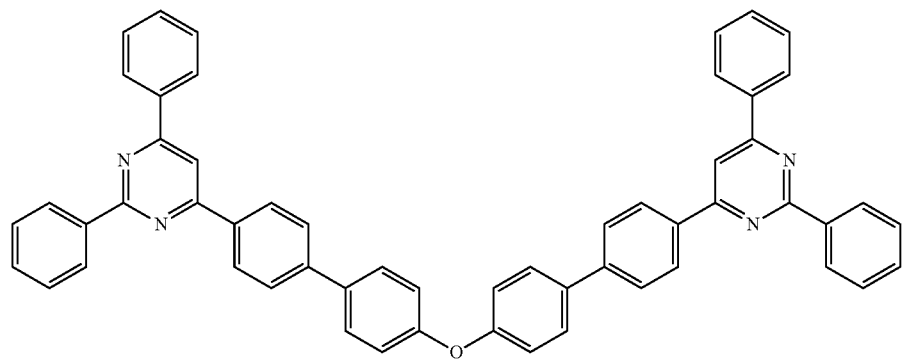

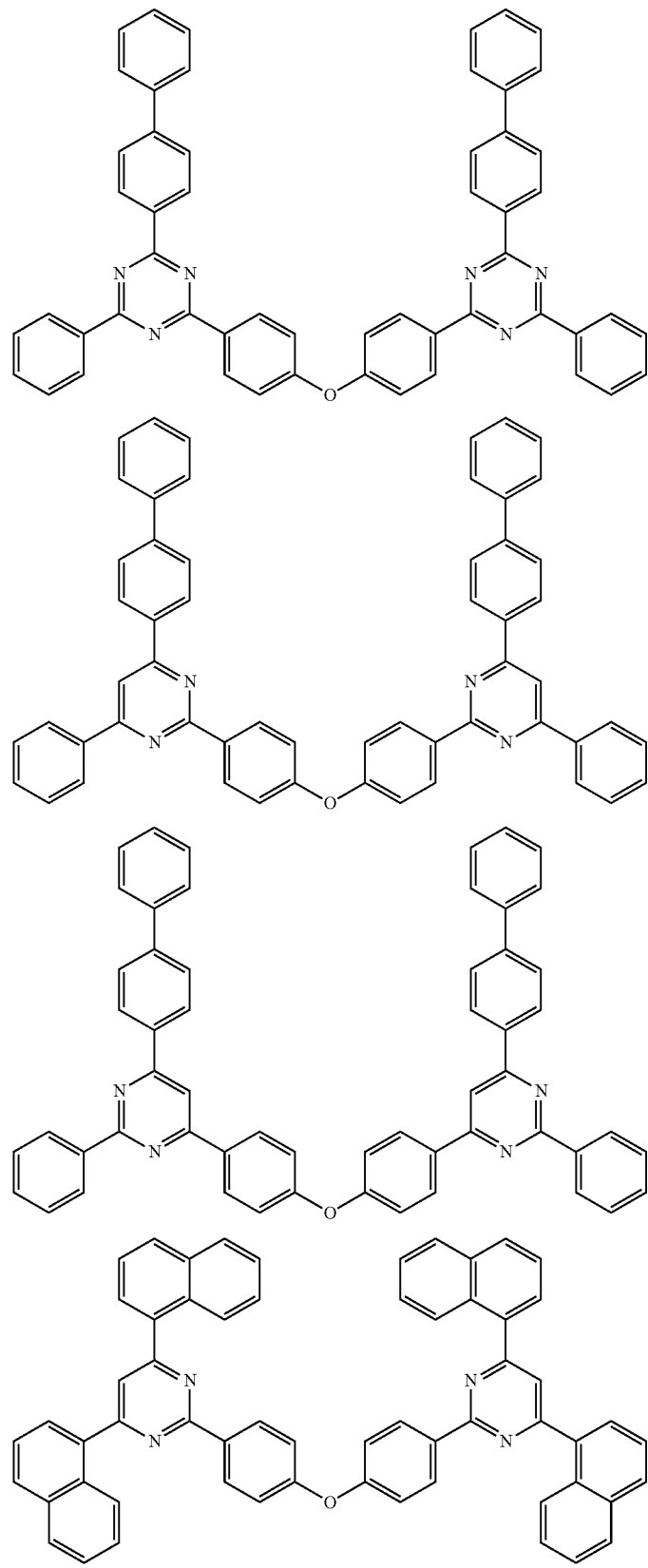

-continued
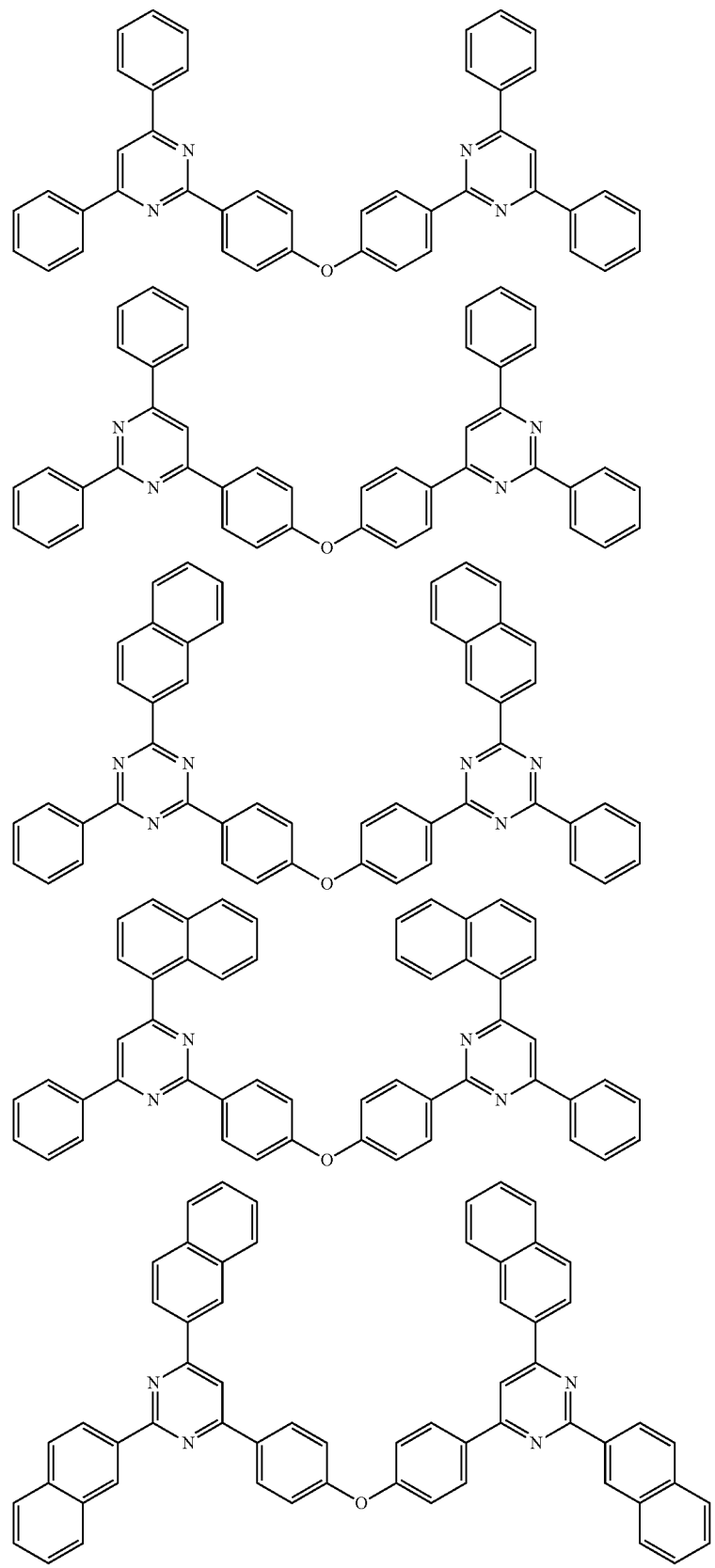

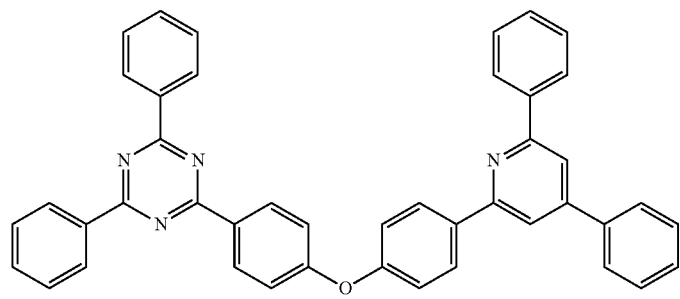
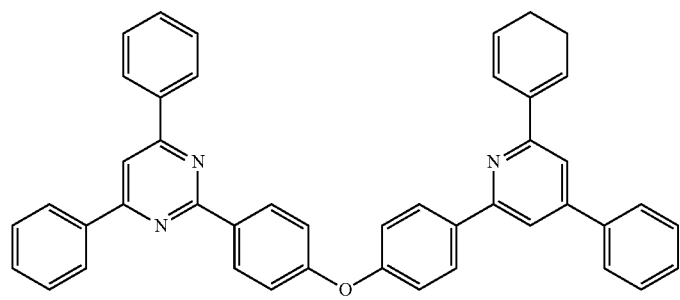
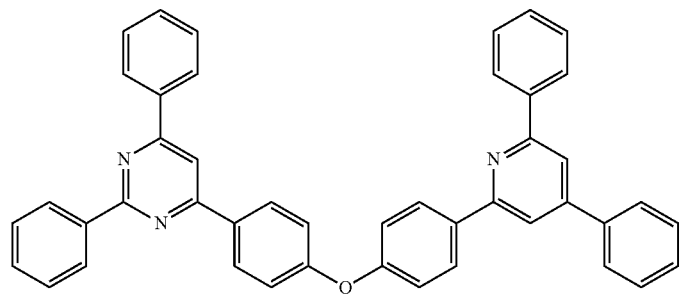
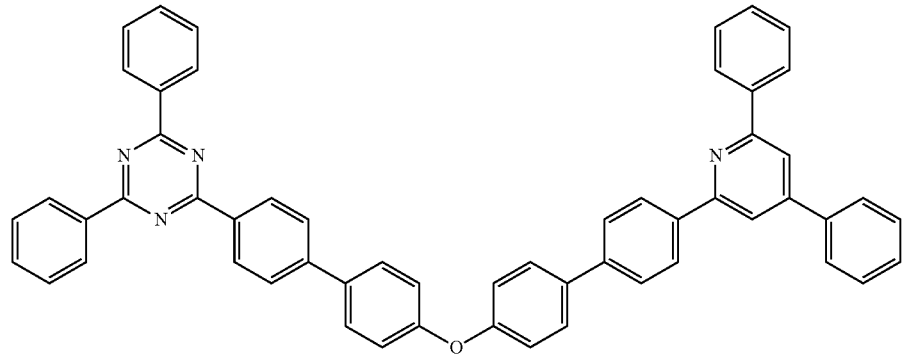
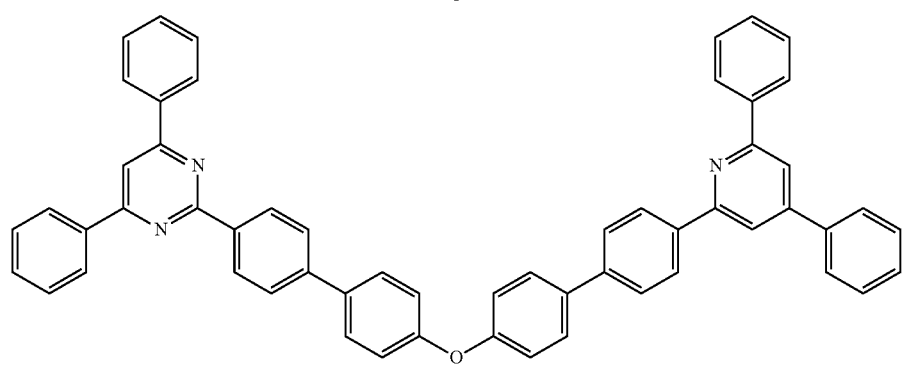

-continued
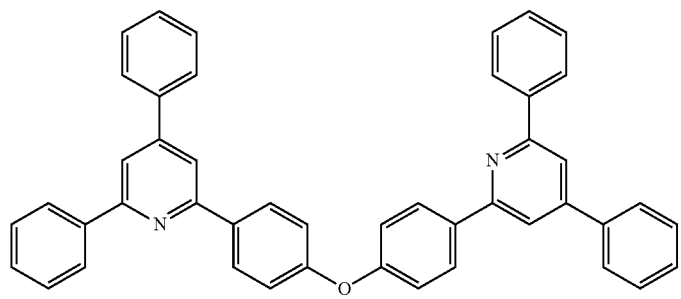
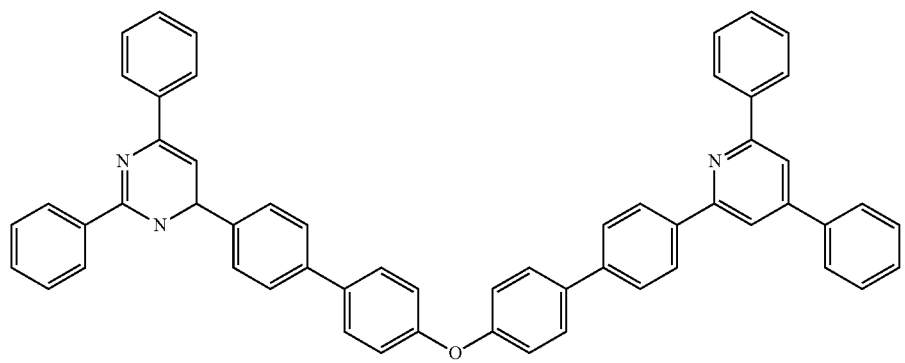
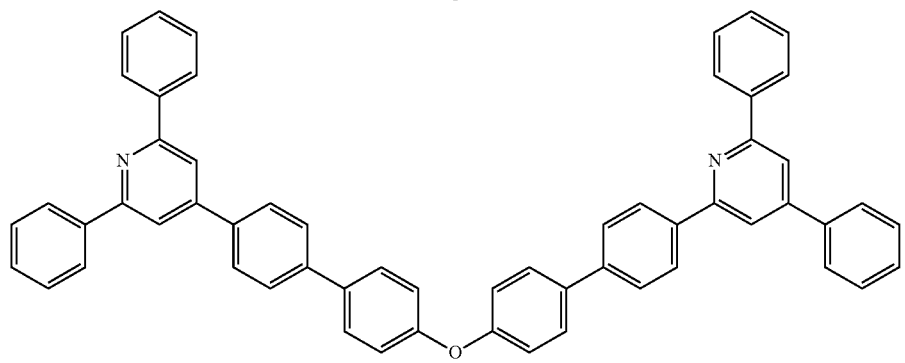
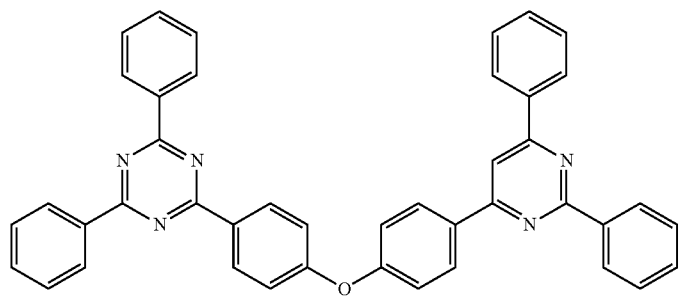
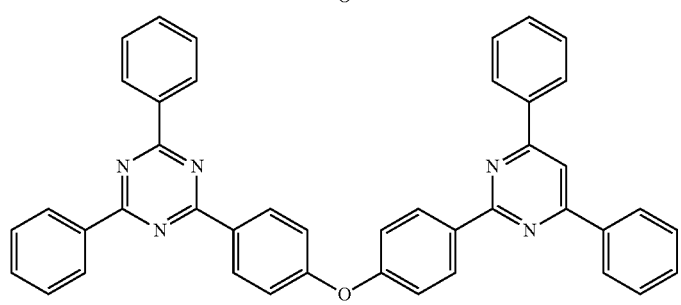

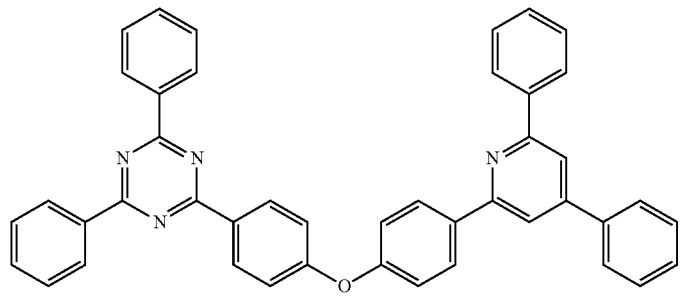
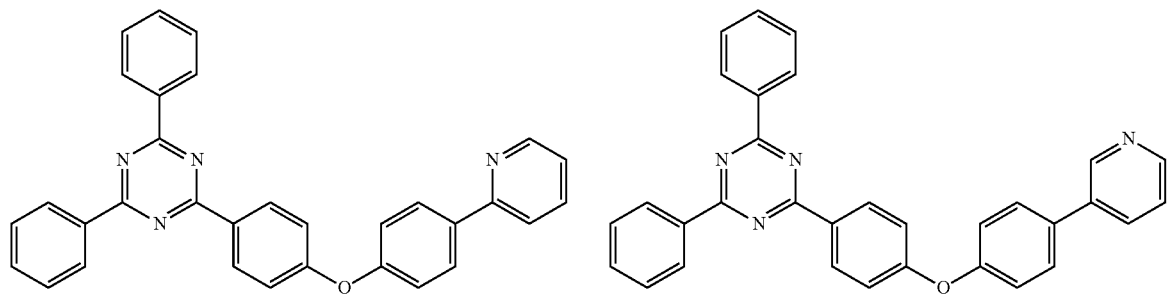
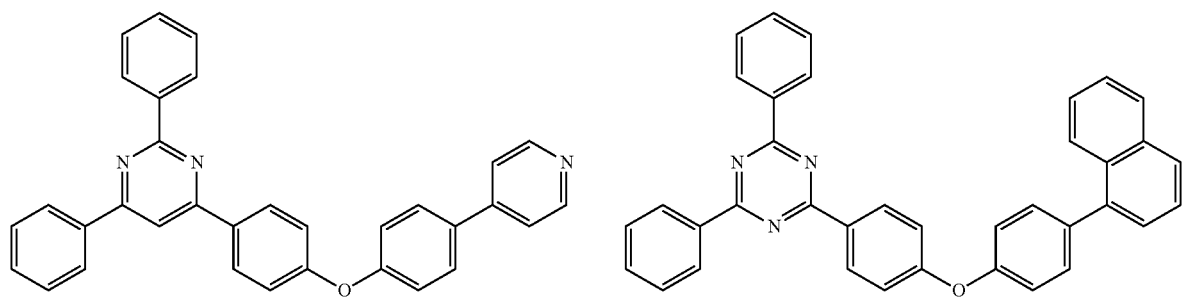
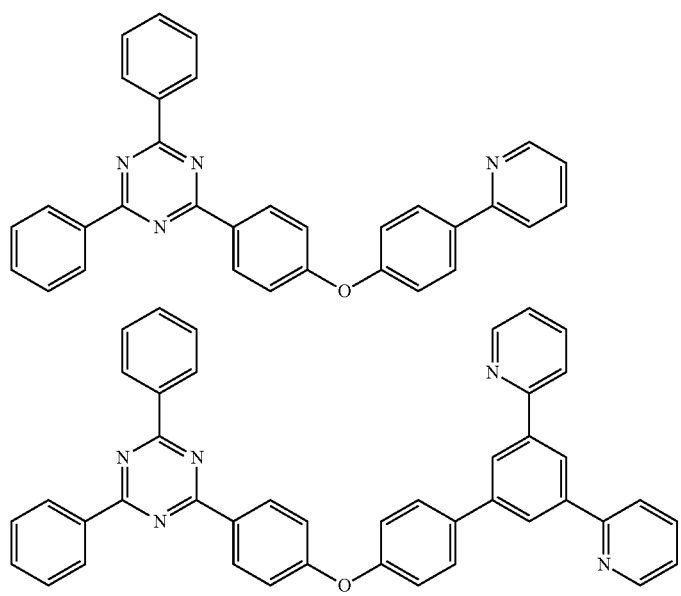

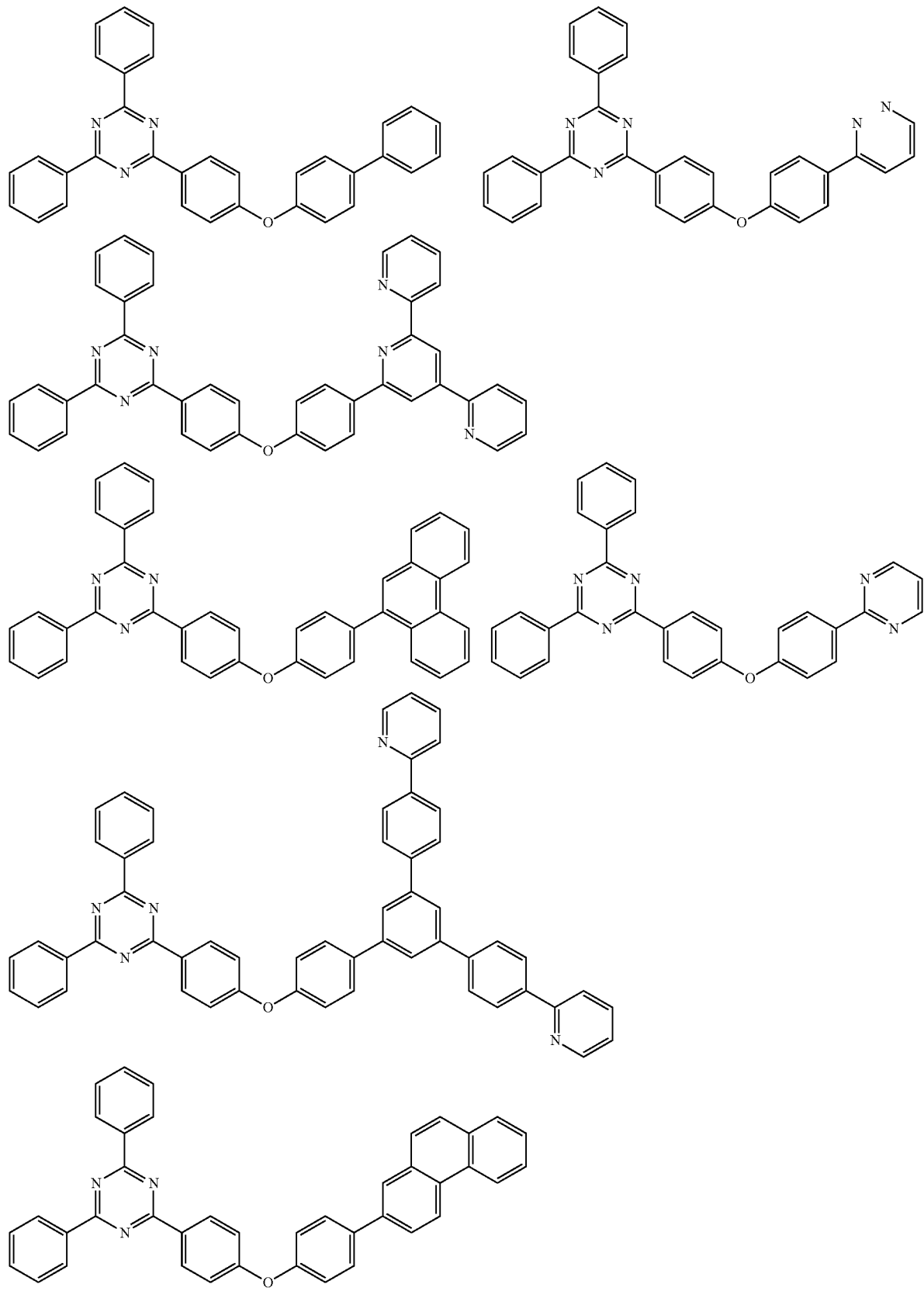

-continued
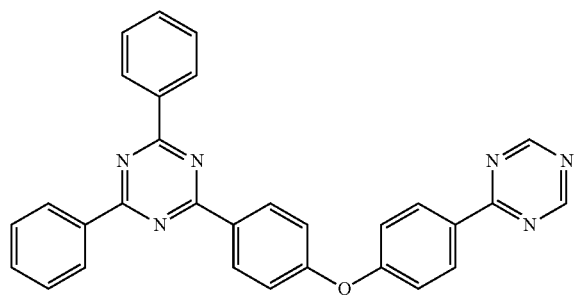
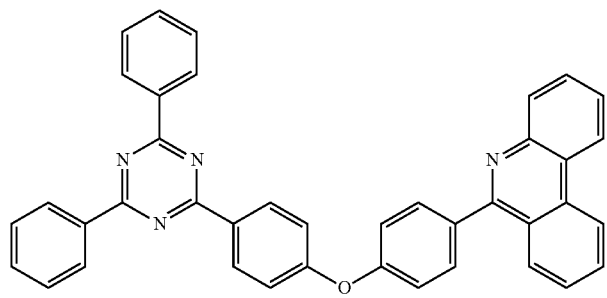
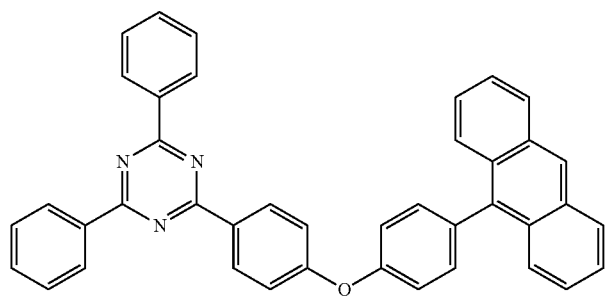
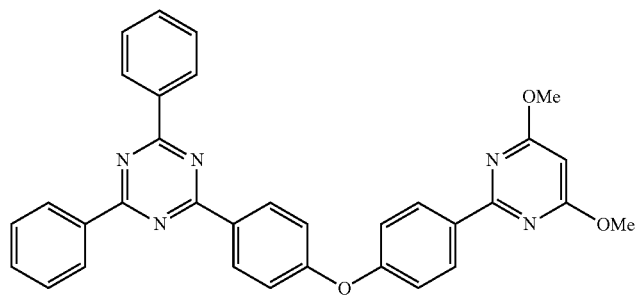
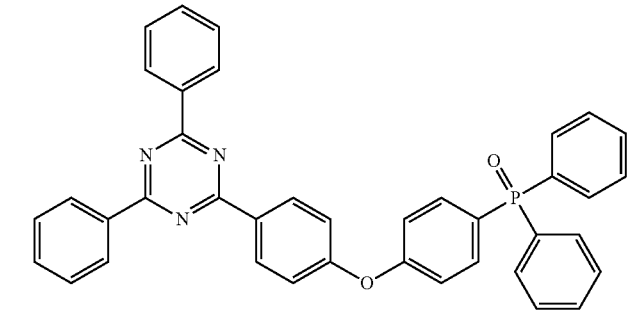

-continued
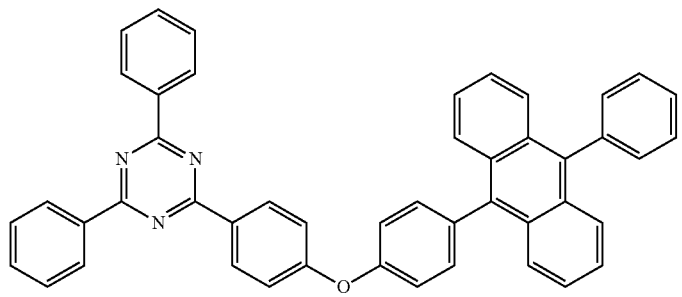
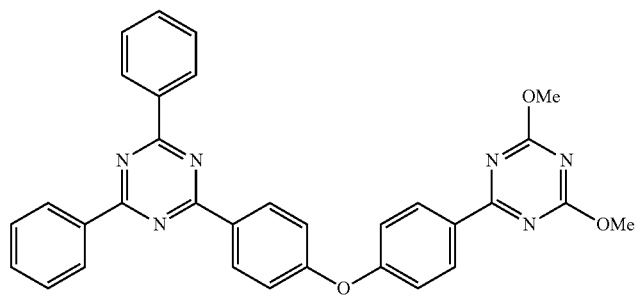
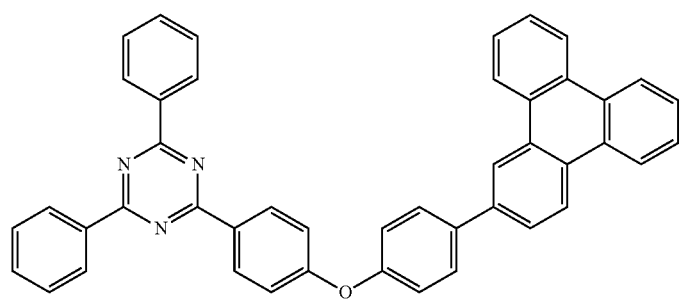
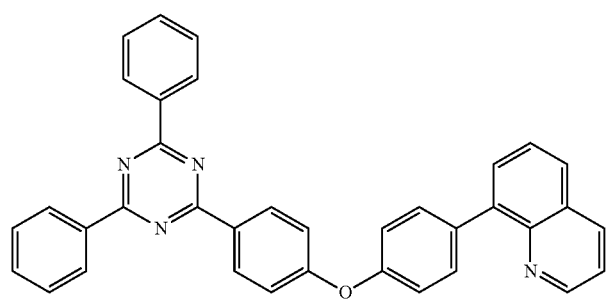
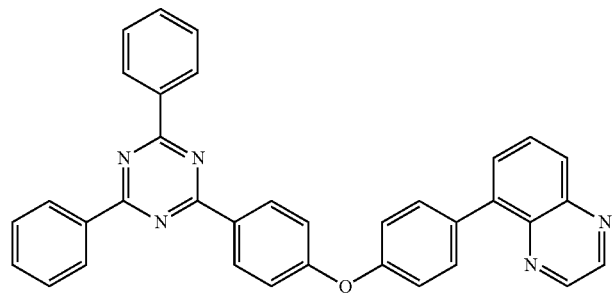

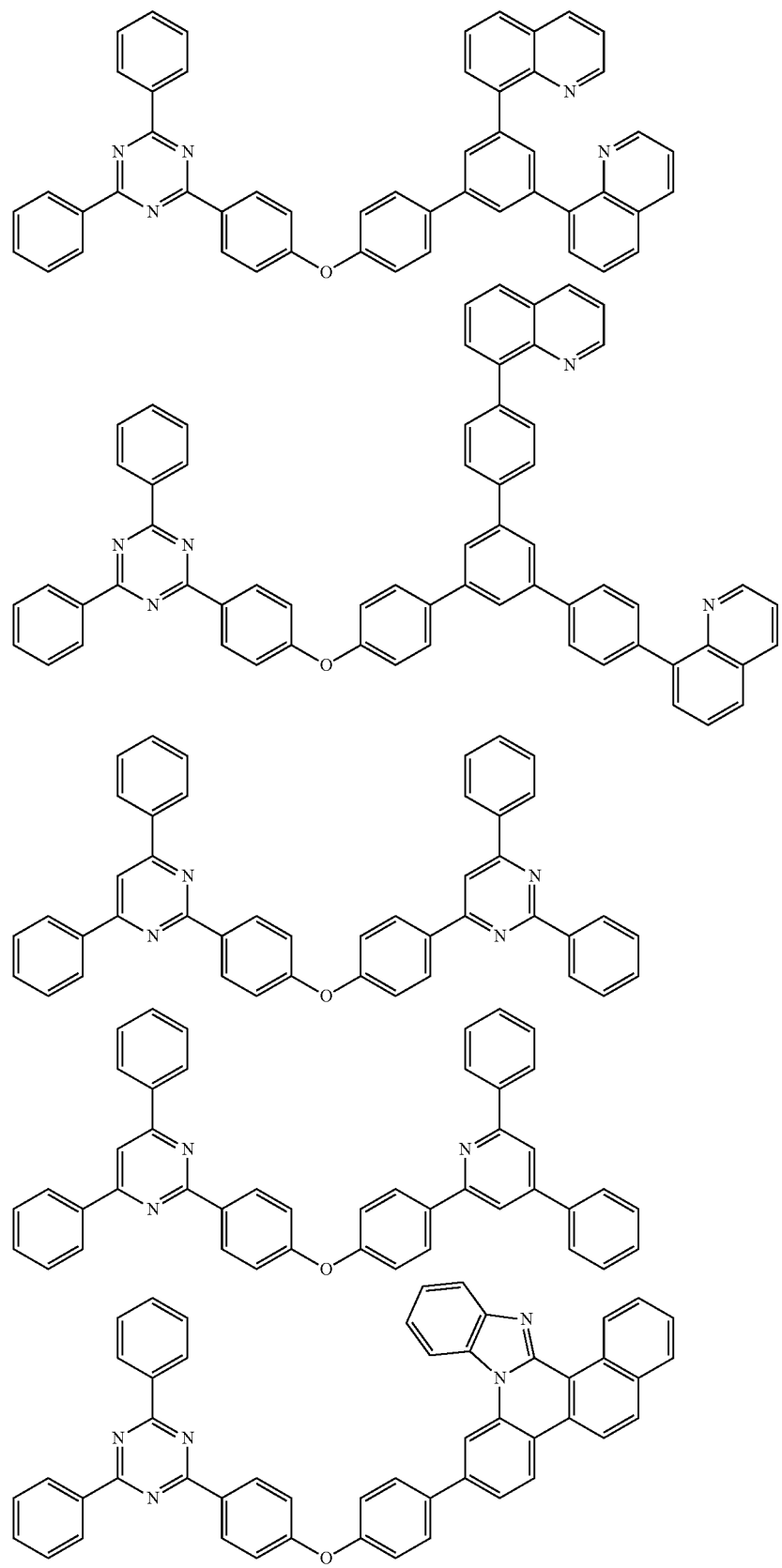

-continued
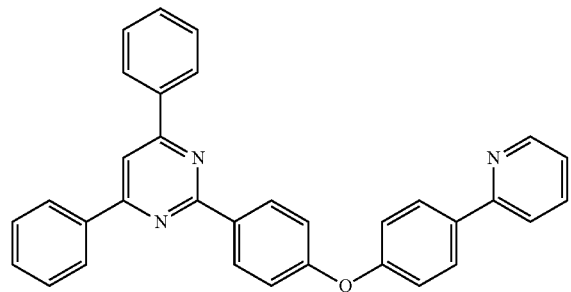
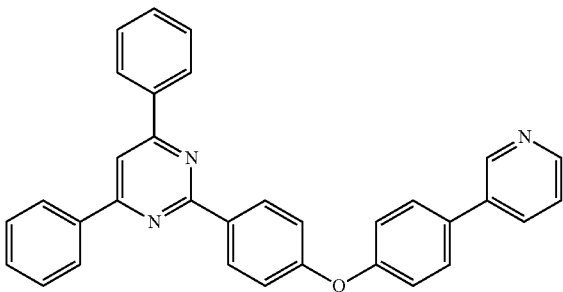
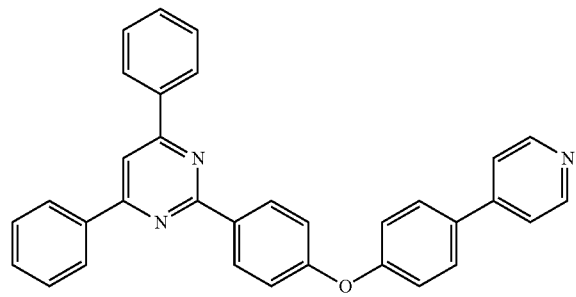
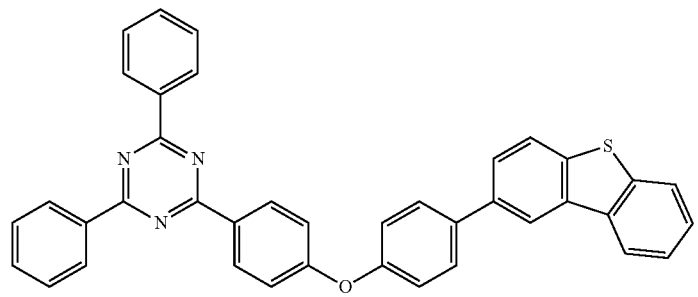
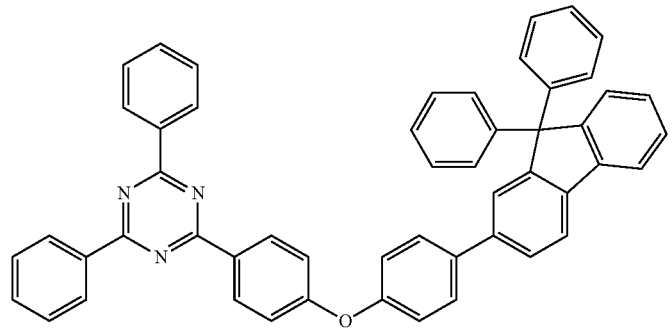
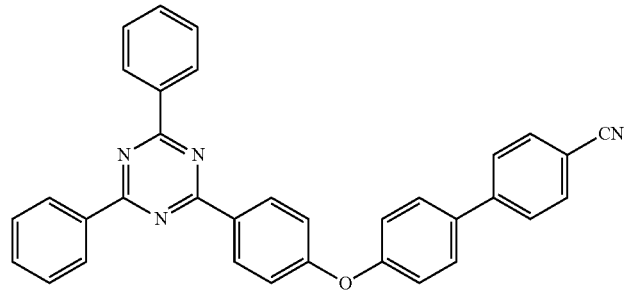

-continued
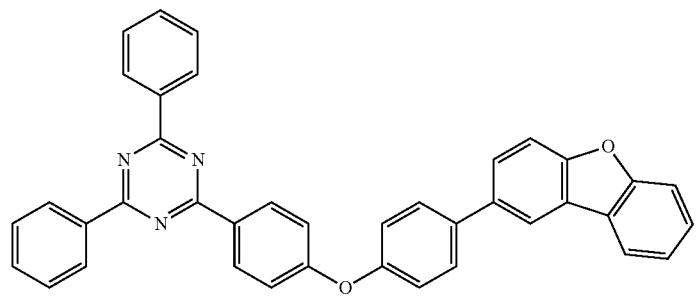
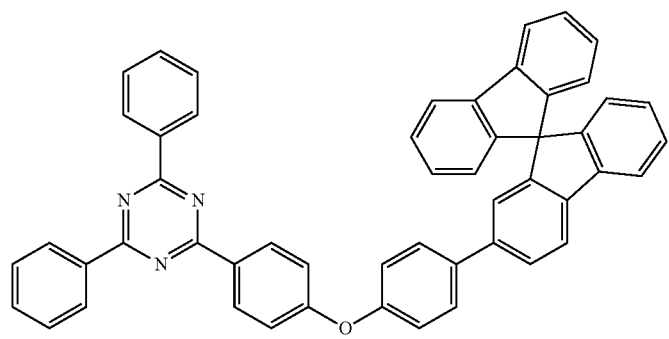
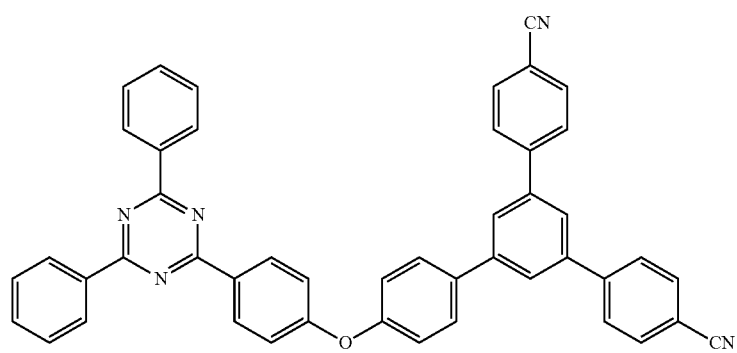
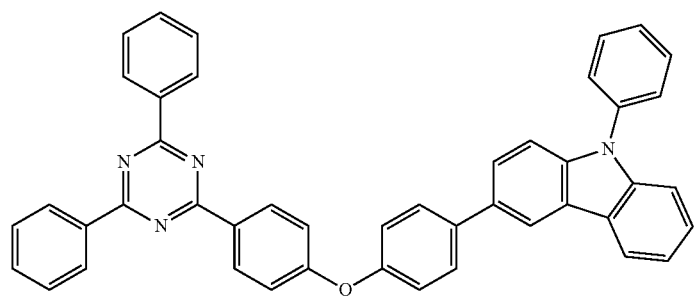
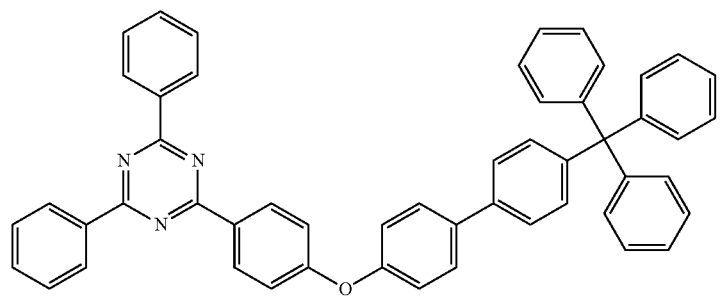

-continued
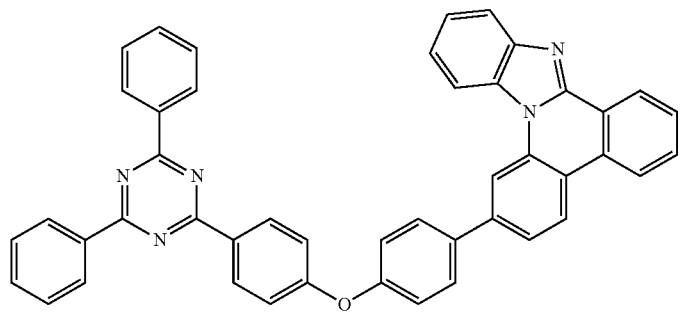
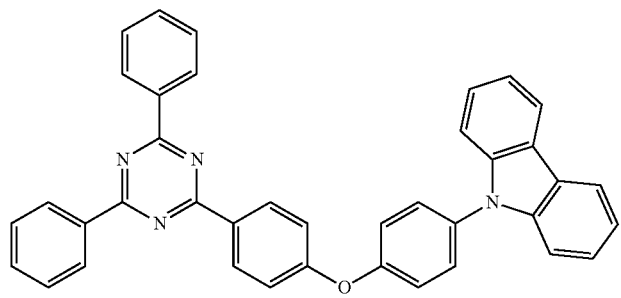
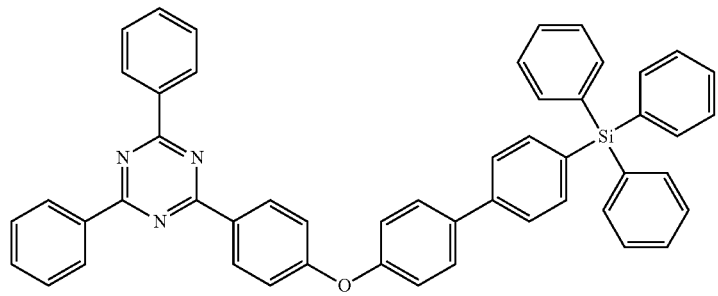
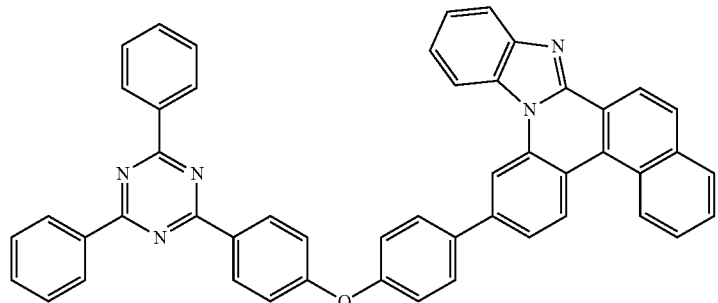
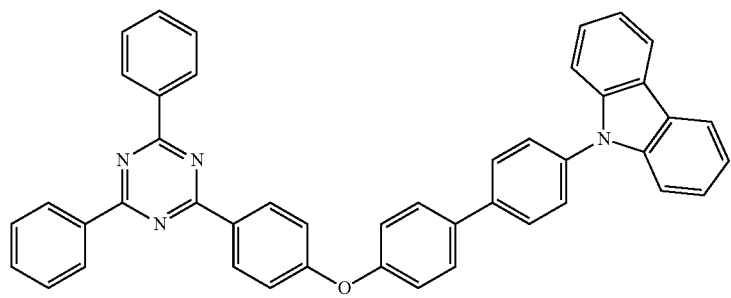

-continued
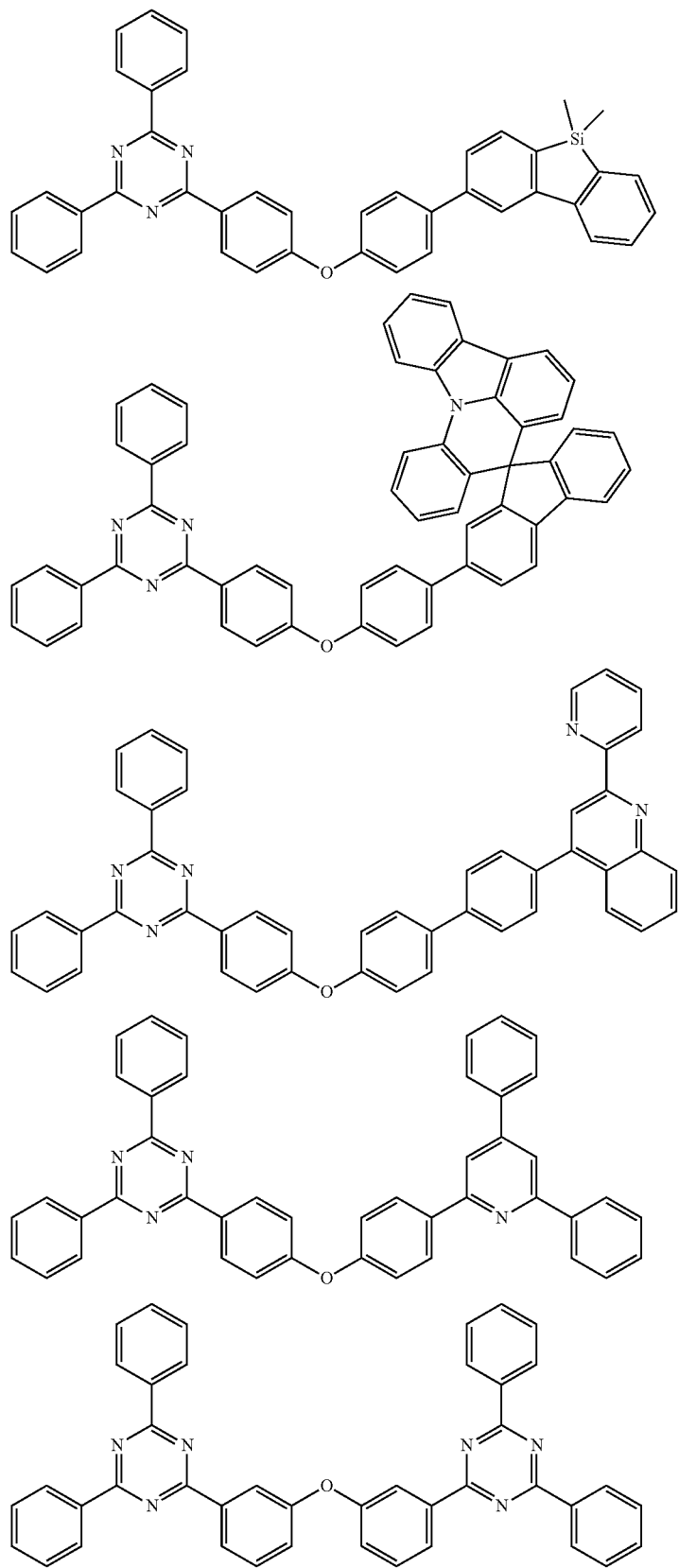

-continued
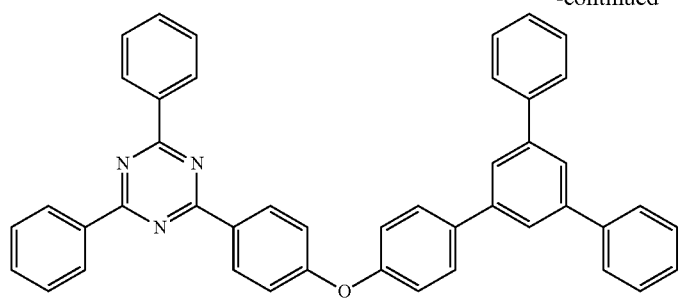
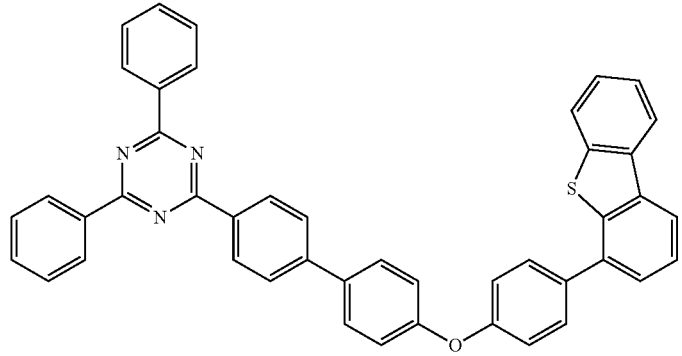
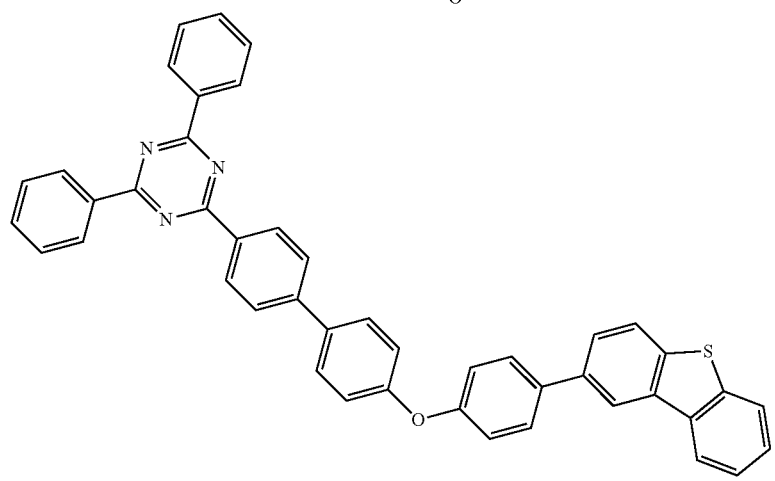
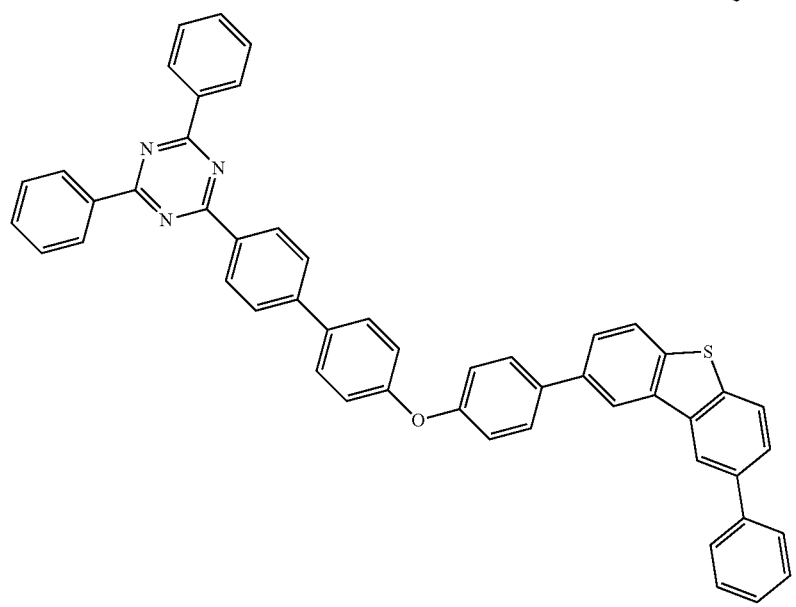

-continued
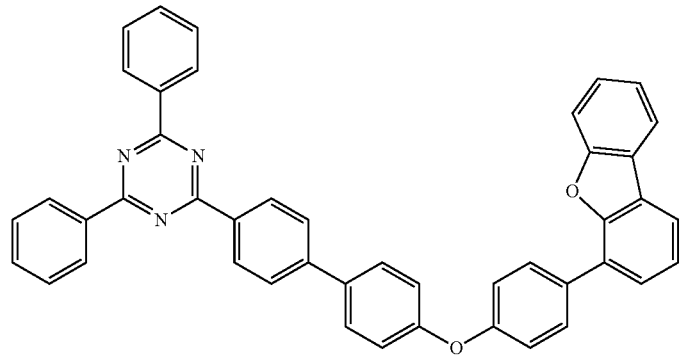
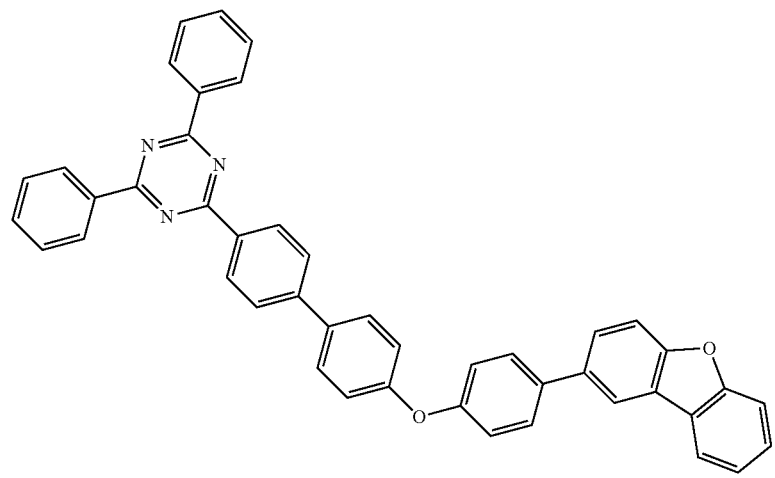
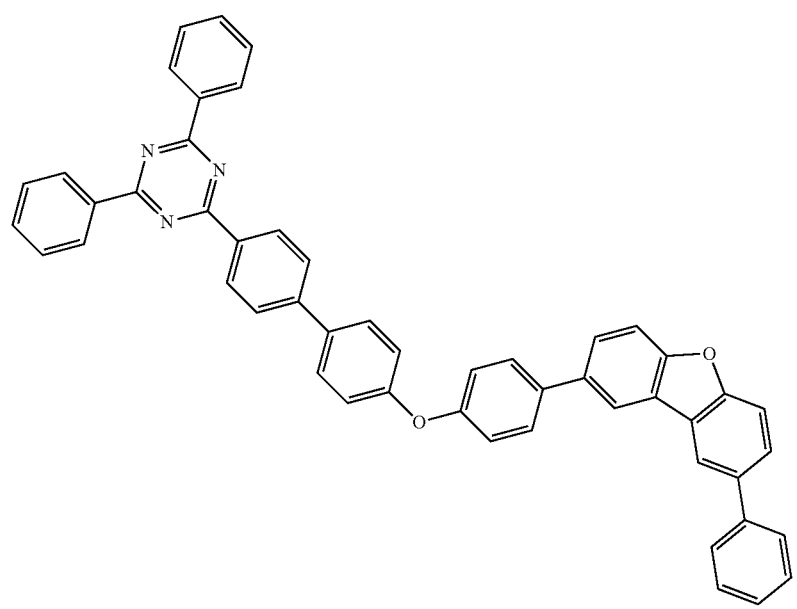

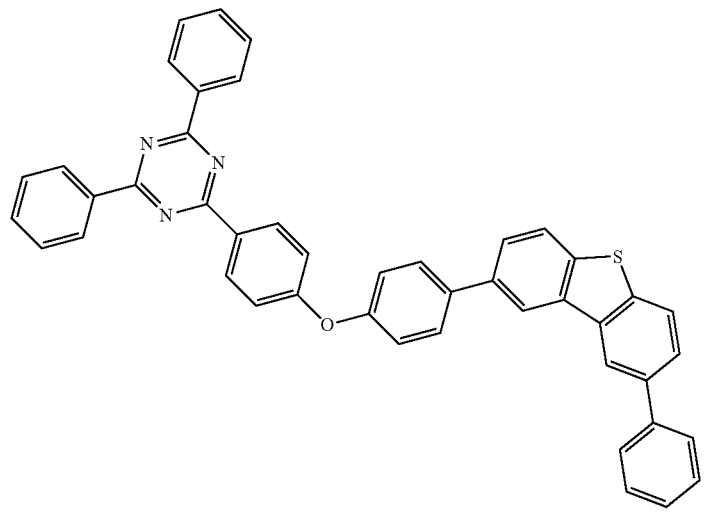
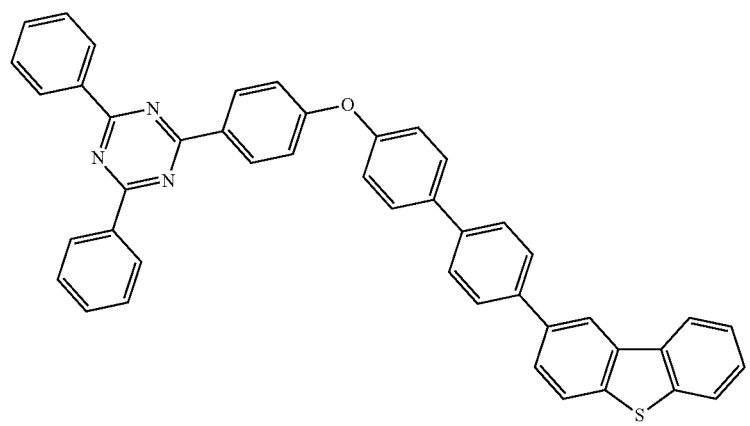
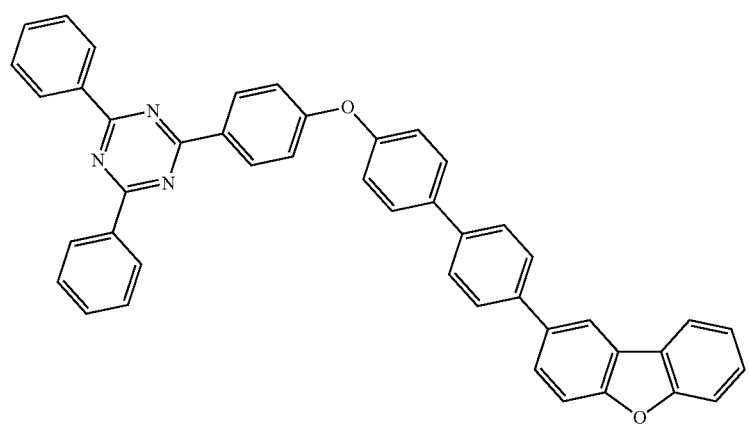

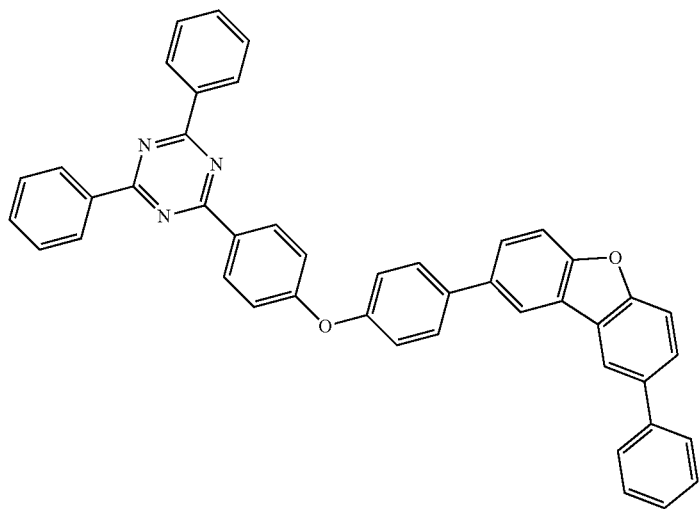
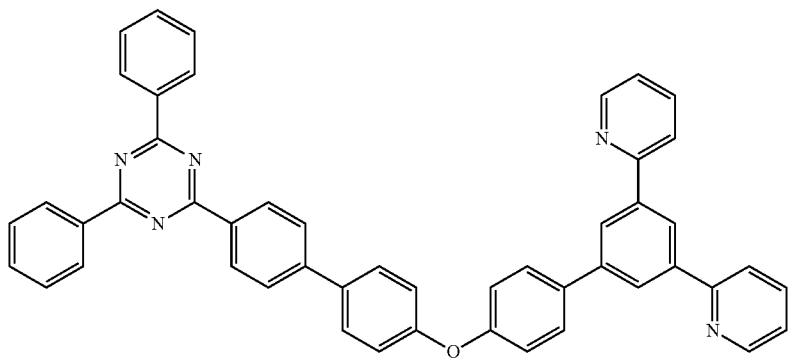
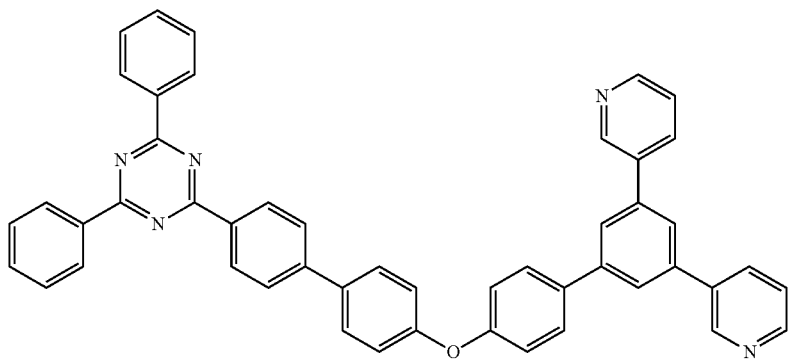
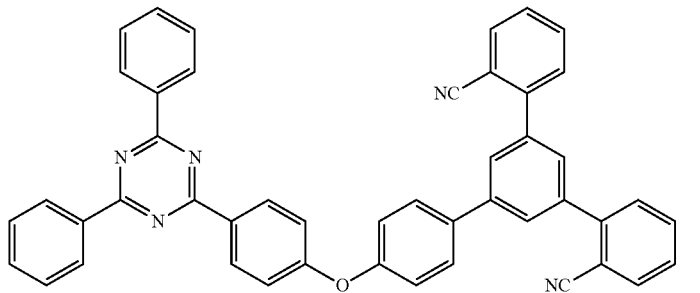

-continued
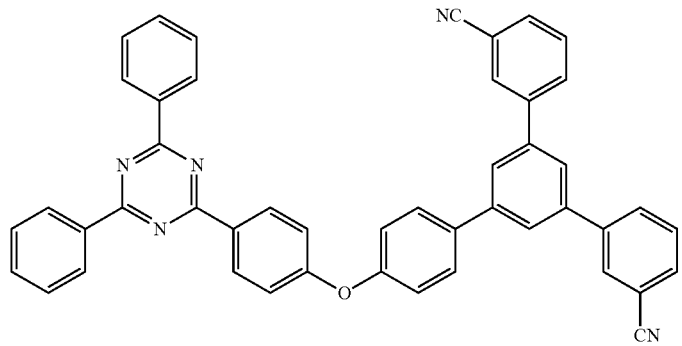
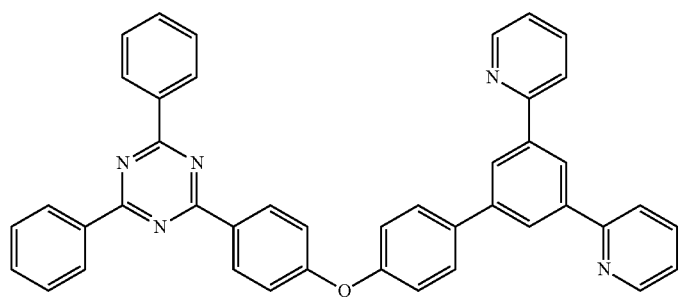
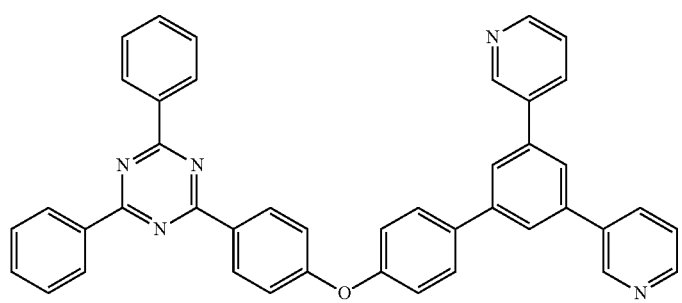
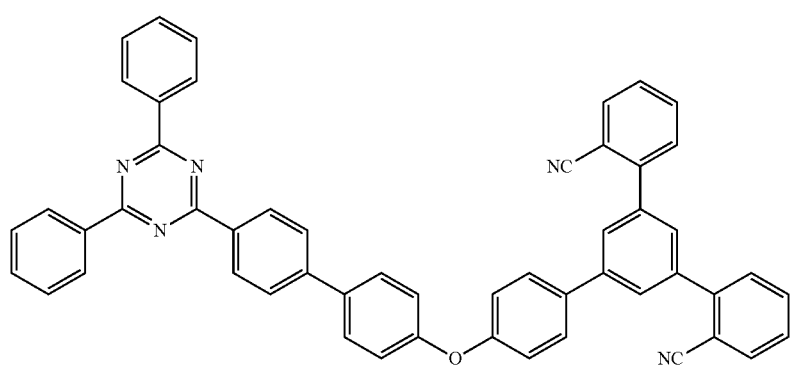
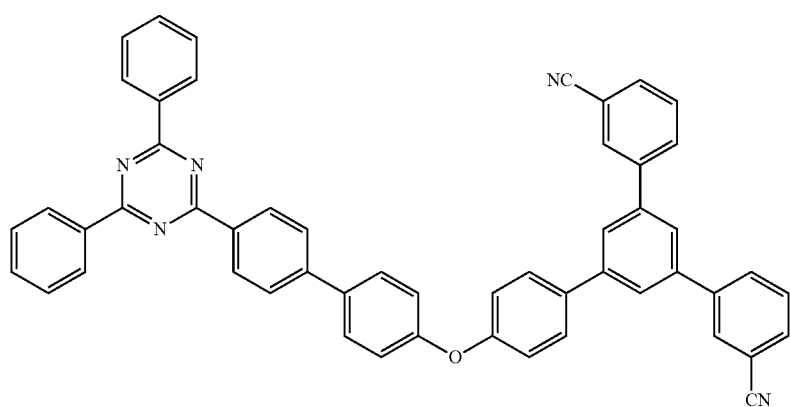

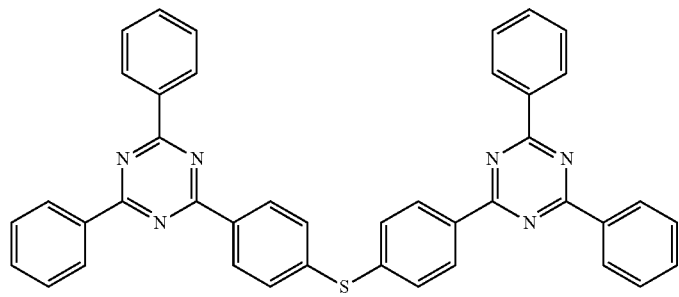
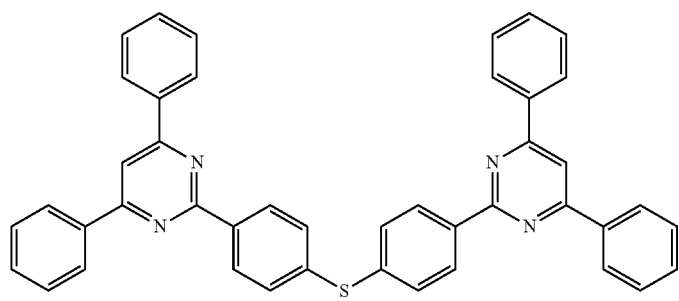
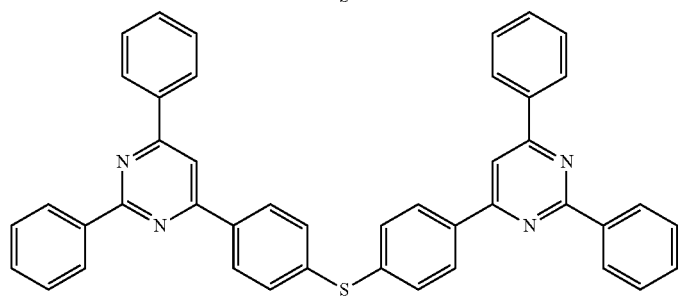
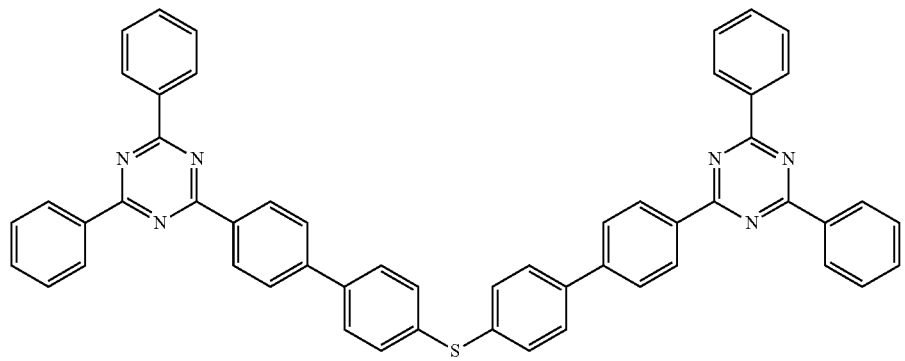
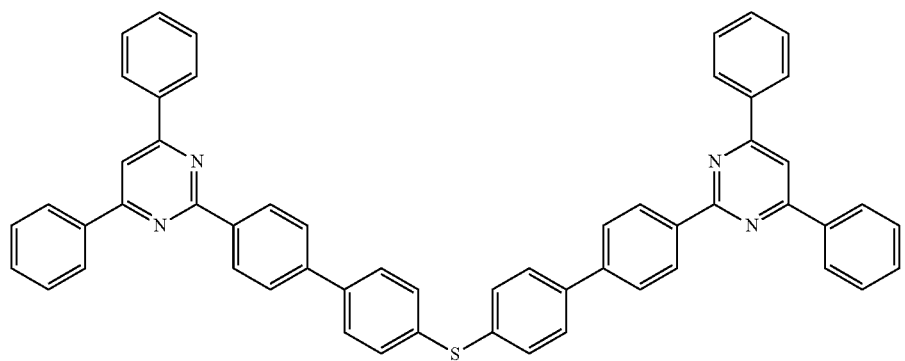

-continued
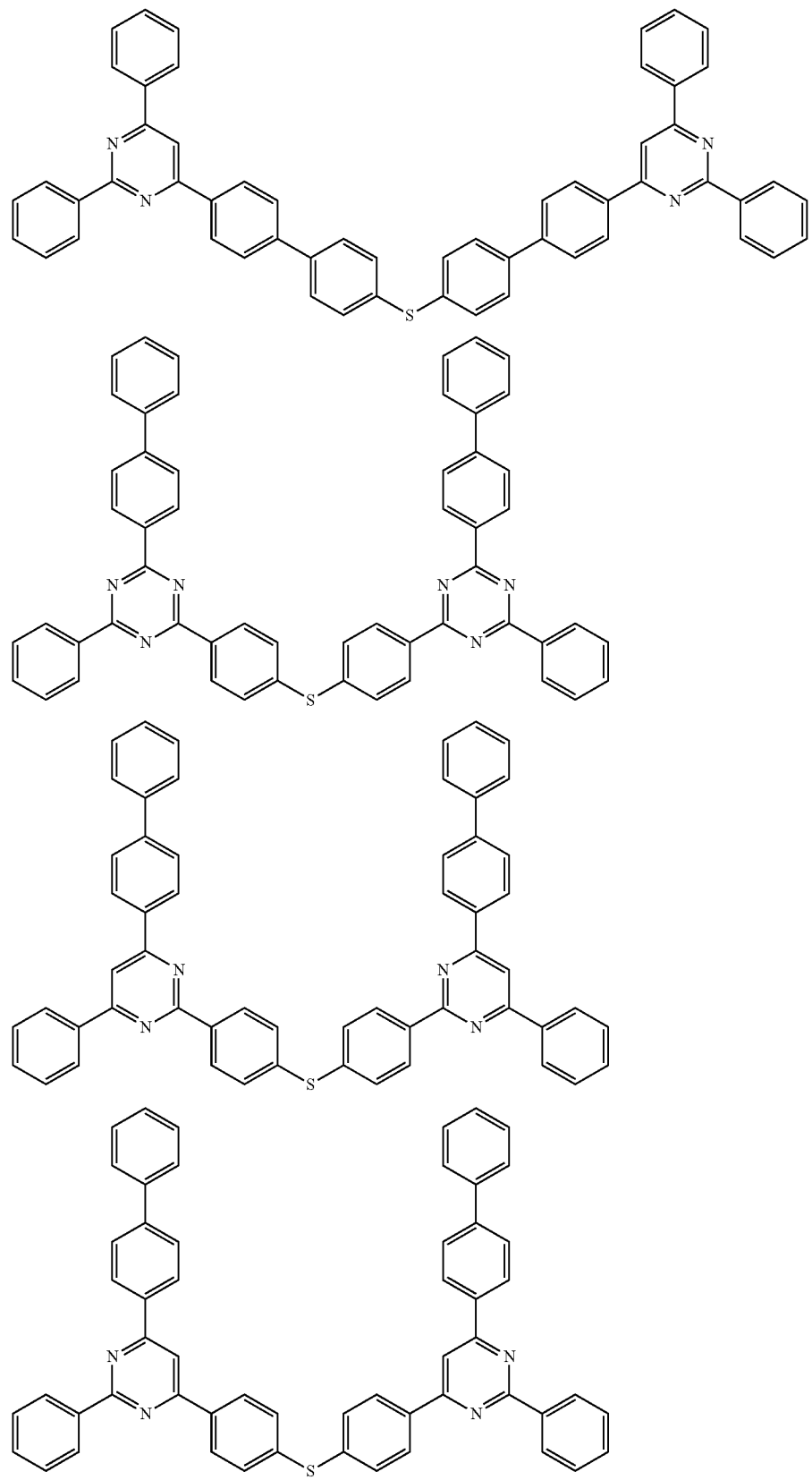

-continued
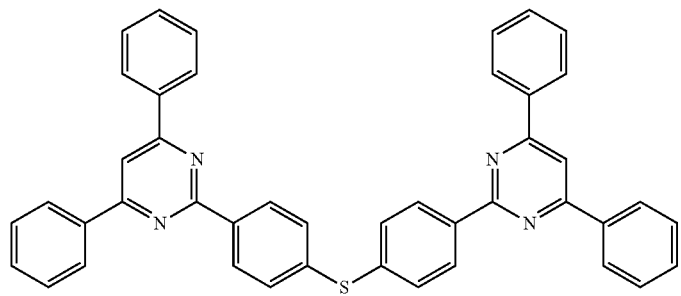
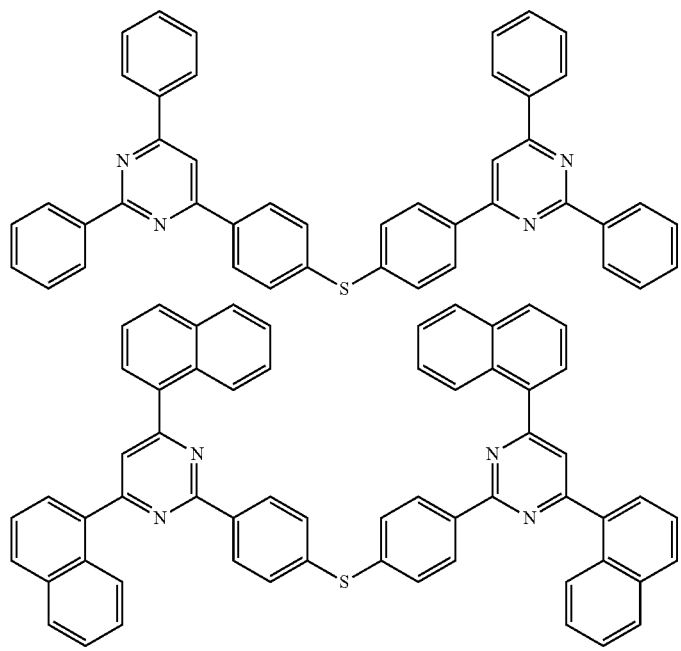
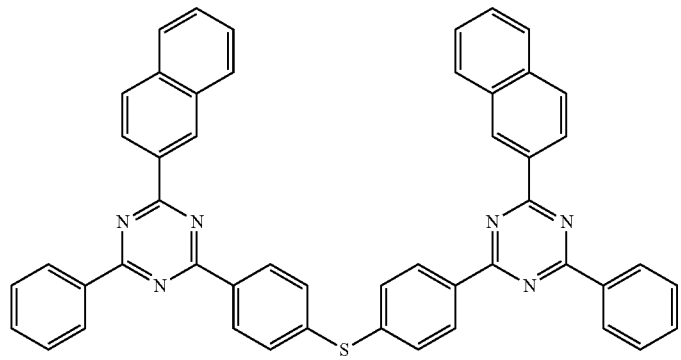
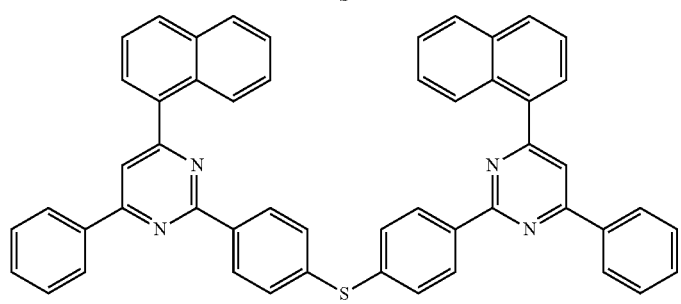

-continued
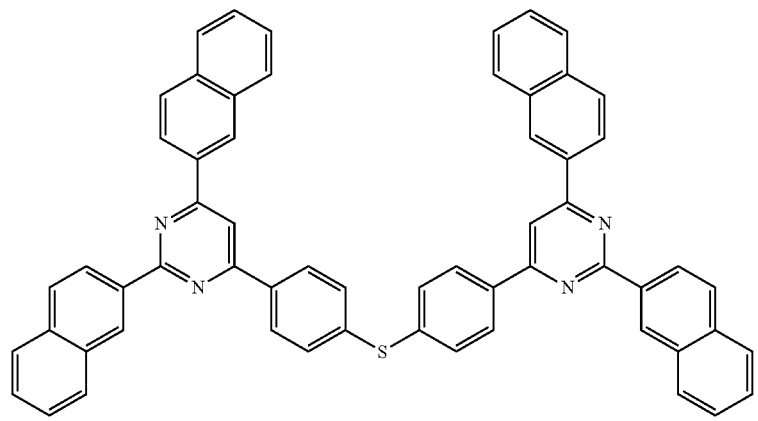
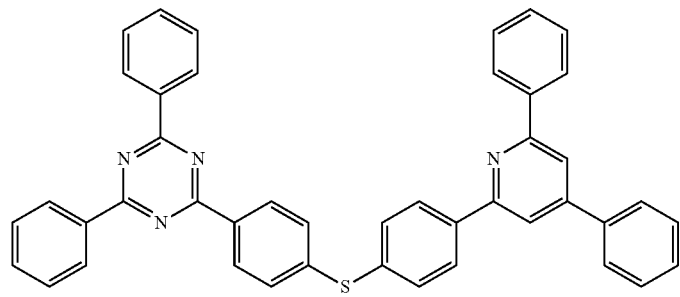
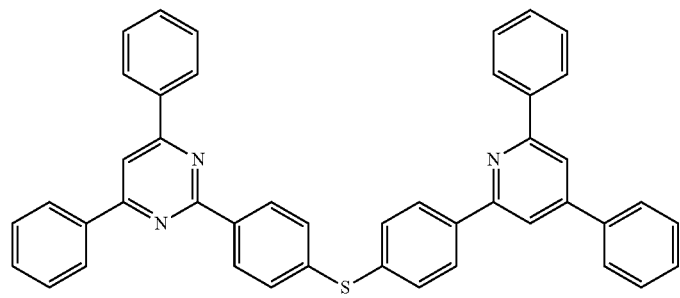
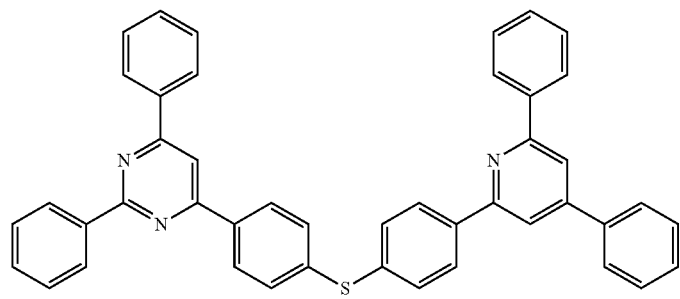
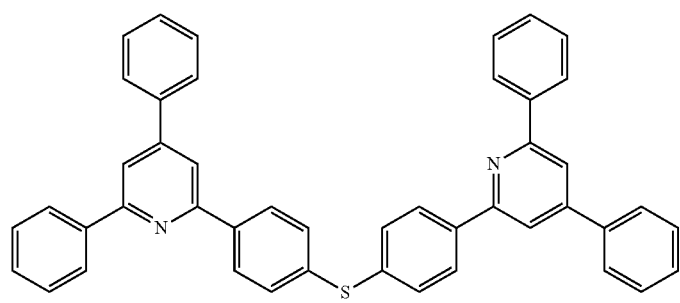

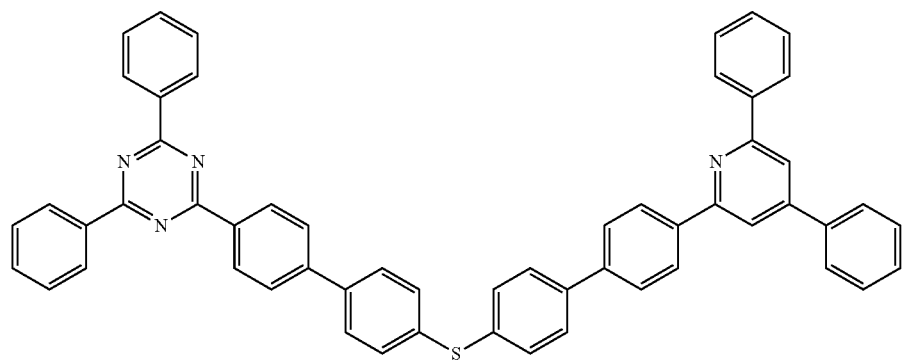
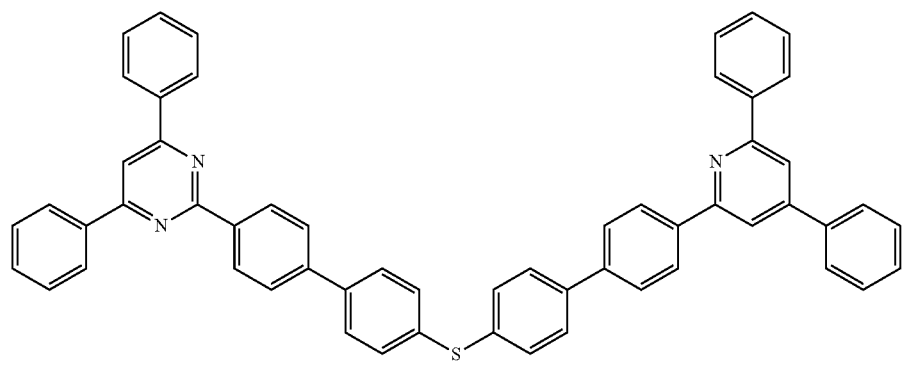
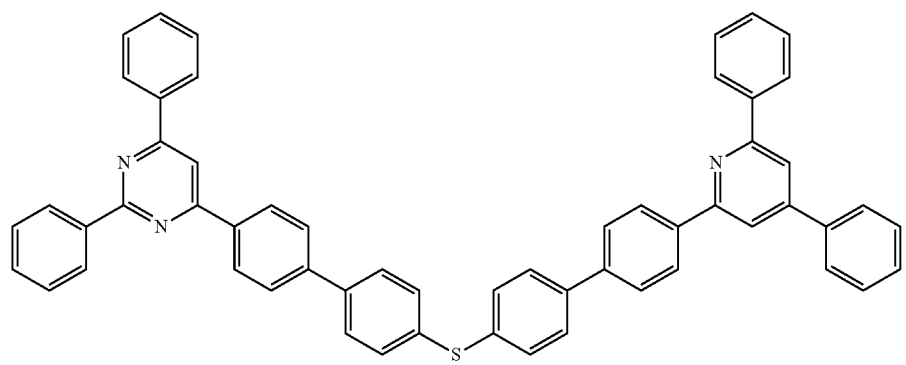
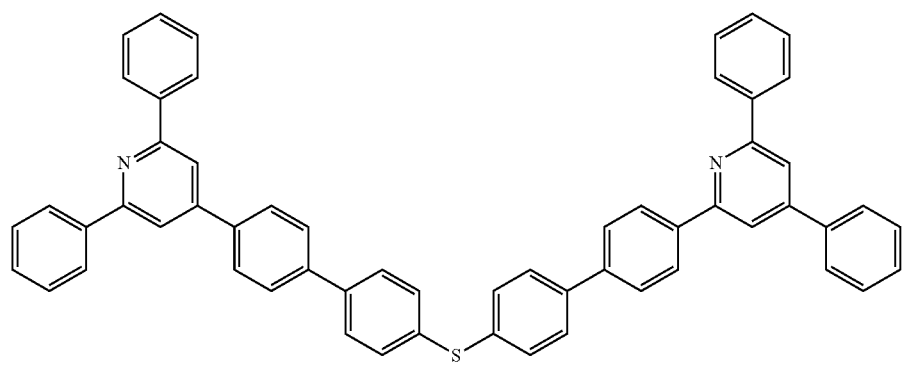

-continued
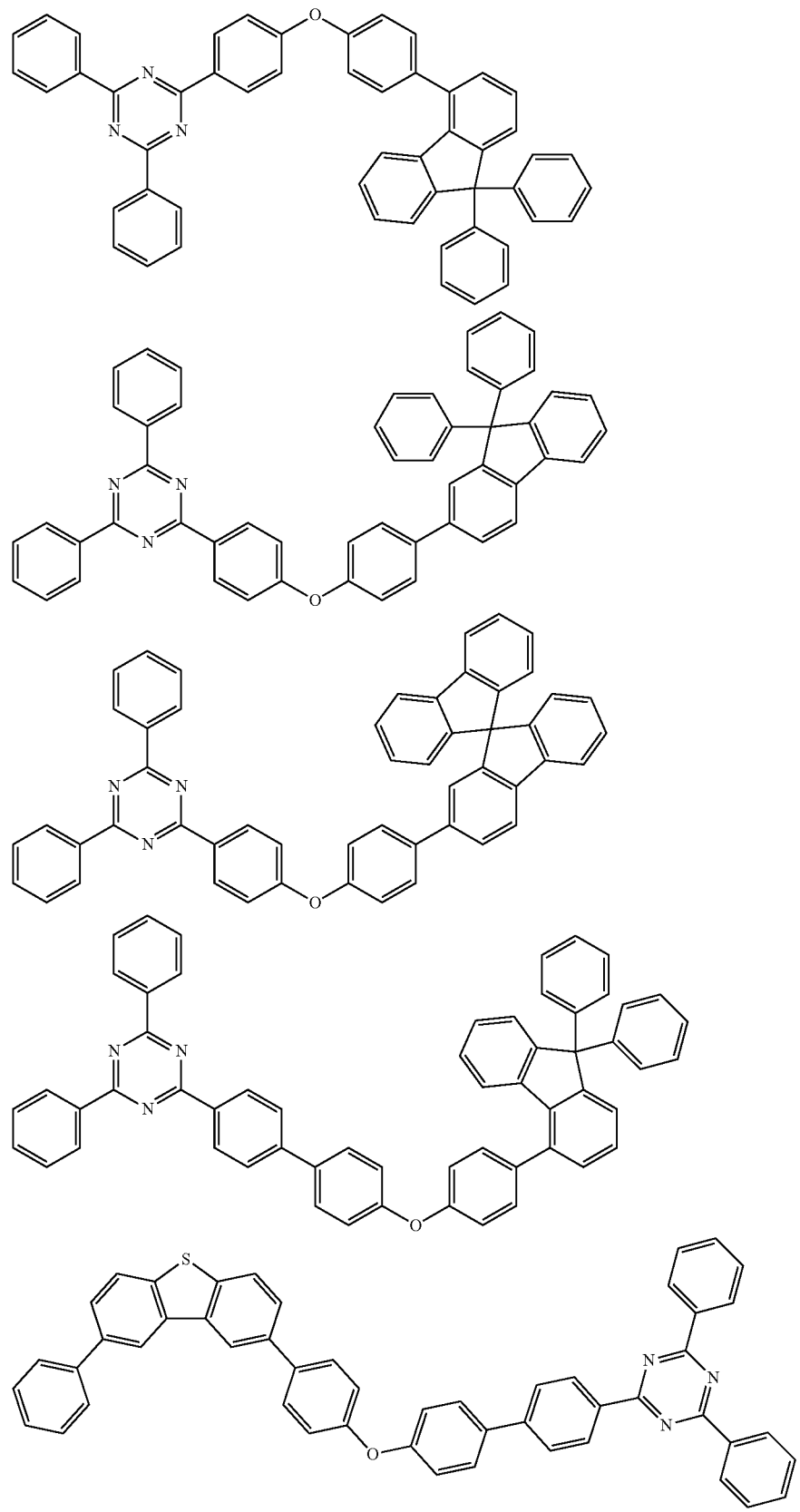

-continued
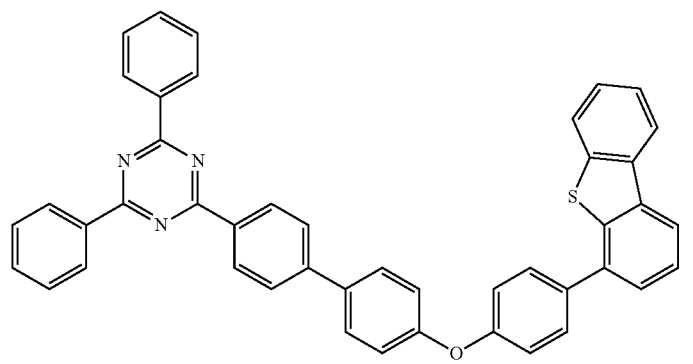
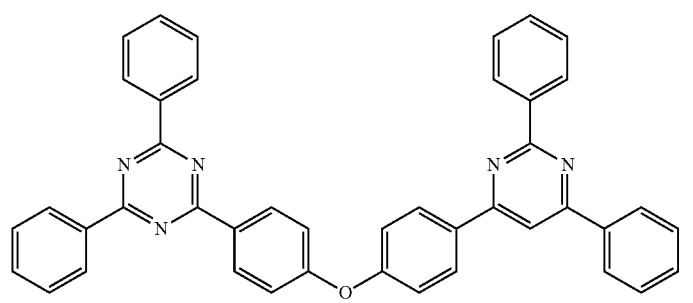
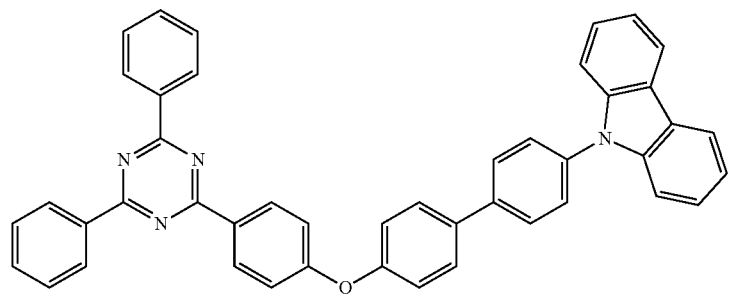
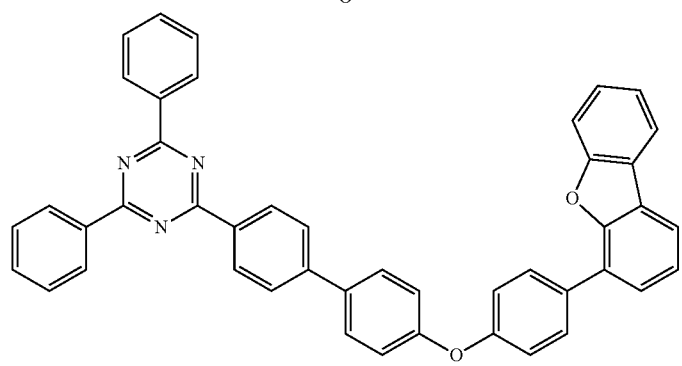
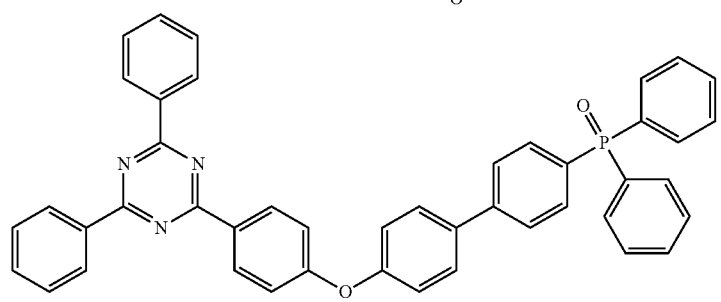

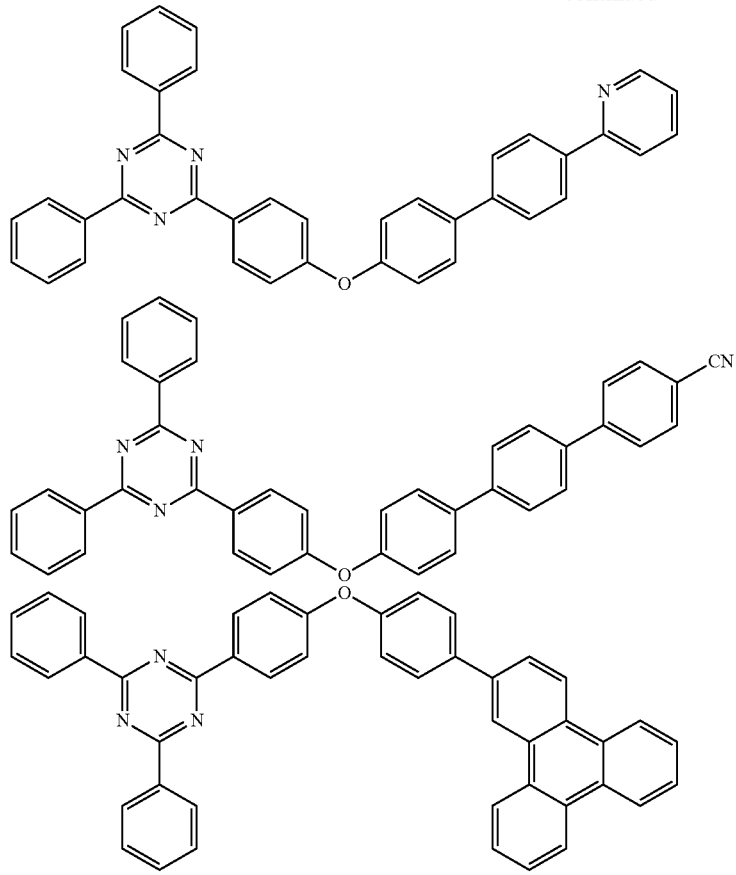

The compound represented by Chemical Formula 1 may be prepared based on the Preparation Examples to be described below.

An exemplary embodiment of the present specification provides an organic electronic device comprising: a first electrode; a second electrode provided to face the first electrode; and one or more organic material layers provided between the first electrode and the second electrode, in which one or more layers of the organic material layers comprise the compound.

When one member is disposed "on" another member in the present specification, this includes not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further included.

The organic material layer of the organic electronic device of the present specification may also be composed of a single-layered structure, but may be composed of a multi-layered structure in which two or more organic material layers are stacked. For example, as a representative example of the organic electronic device of the present specification, an organic light emitting device may have a structure comprising a hole injection layer, a hole transport layer, a light emitting layer, an electron transport layer, an electron injection layer, and the like as organic material layers. However, the structure of the organic electronic device is not limited thereto, and may comprise a fewer number of organic layers.

According to an exemplary embodiment of the present specification, the organic electronic device may be selected from the group consisting of an organic light emitting device, an organic phosphorescent device, an organic solar cell, an organic photoconductor (OPC), and an organic transistor.

Hereinafter, an organic light emitting device will be exemplified.

According to an exemplary embodiment of the present specification, the organic material layer comprises a light emitting layer, and the light emitting layer comprises the compound.

According to an exemplary embodiment of the present specification, the organic material layer comprises a hole injection layer or a hole transport layer, and the hole injection layer or the hole transport layer comprises the compound.

In another exemplary embodiment, the organic material layer comprises a light emitting layer, and the light emitting layer includes the compound.

According to an exemplary embodiment of the present specification, the organic material layer comprises an electron transport layer or an electron injection layer, and the electron transport layer or the electron injection layer comprises the compound.

According to an exemplary embodiment of the present specification, the organic material layer comprises an electron blocking layer or a hole blocking layer, and the electron blocking layer or the hole blocking layer comprises the compound.

According to an exemplary embodiment of the present specification, the organic light emitting device further comprises one or two or more layers selected from the group consisting of a hole injection layer, a hole transport layer, an electron transport layer, an electron injection layer, an electron blocking layer, and a hole blocking layer.

When the organic material layer comprising the compound of Chemical Formula 1 is an electron transport layer, the electron transport layer may further comprise an n-type dopant.

As the n-type dopant, those known in the art may be used, and for example, a metal or a metal complex may be used. According to an example, the electron transport layer comprising the compound of Chemical Formula 1 may further comprise LiQ.

According to an exemplary embodiment of the present specification, the organic light emitting device comprises: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers comprises the compound. In an exemplary embodiment of the present application, as the two or more organic material layers, two or more may be selected from the group consisting of an electron transport layer, an electron injection layer, a layer which transports and injects electrons simultaneously, and a hole blocking layer.

According to an exemplary embodiment of the present specification, the organic material layer comprises two or more electron transport layers, and at least one of the two or more electron transport layers comprises the compound. Specifically, according to an exemplary embodiment of the present specification, the compound may also be comprised in one layer of the two or more electron transport layers, and may be comprised in each of the two or more electron transport layers.

In addition, according to an exemplary embodiment of the present specification, when the compound is comprised in each of the two or more electron transport layers, the other materials except for the compound may be the same as or different from each other.

In an exemplary embodiment of the present specification, the organic material layer comprises a light emitting layer, and the light emitting layer comprises a compound represented by the following Chemical Formula A.

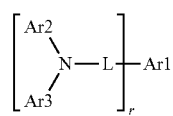

[Chemical Formula A]

In Chemical Formula A,

Ar1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L is a direct bond; a substituted or unsubstituted arylene group; or a substituted or unsubstituted heteroarylene group, Ar2 and Ar3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or may combine with each other to form a substituted or unsubstituted ring, r is an integer of 1 or more, and when r is 2 or more, the substituents in the parenthesis are the same as or different from each other.

According to an exemplary embodiment of the present specification, the organic material layer includes a light emitting layer, and the light emitting layer includes the compound represented by Chemical Formula A as a dopant of the light emitting layer.

In an exemplary embodiment of the present specification, L is a direct bond.

According to an exemplary embodiment of the present specification, r is 2.

In an exemplary embodiment of the present specification, Ar1 is a substituted or unsubstituted divalent pyrene group.

In another exemplary embodiment, Ar1 is a divalent pyrene group which is unsubstituted or substituted with a methyl group, an ethyl group, a t-butyl group or an isopropyl group.

In still another exemplary embodiment, Ar1 is a divalent pyrene group.

In an exemplary embodiment of the present specification, Ar2 and Ar3 are the same as or different from each other, and are each independently a substituted or unsubstituted aryl group having 6 to 30 carbon atoms; a substituted or unsubstituted alkyl group having 1 to 30 carbon atoms; or a substituted or unsubstituted heteroaryl group having 2 to 30 carbon atoms.

According to an exemplary embodiment of the present specification, Ar2 and Ar3 are the same as or different from each other, and are each independently a substituted or unsubstituted aryl group having 6 to 30 carbon atoms. According to an exemplary embodiment of the present specification, Ar2 and Ar3 are the same as or different from each other, and are each independently an aryl group having 6 to 30 carbon atoms, which is unsubstituted or substituted with a silyl group substituted with an alkyl group.

In an exemplary embodiment of the present specification, Ar2 and Ar3 are is a phenyl group which is unsubstituted or substituted with a trimethylsilyl group.

According to an exemplary embodiment of the present specification, Chemical Formula A may be represented by the following compound.

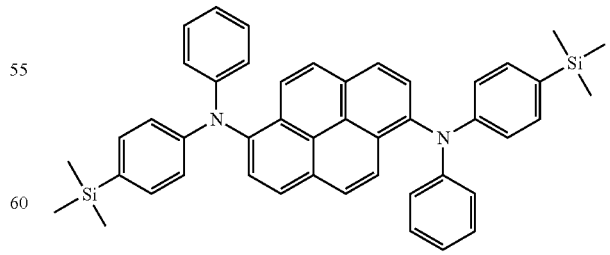

In an exemplary embodiment, the organic material layer comprises a light emitting layer, and the light emitting layer comprises a compound represented by the following Chemical Formula B.

[Chemical Formula B]

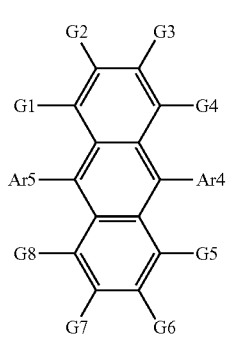

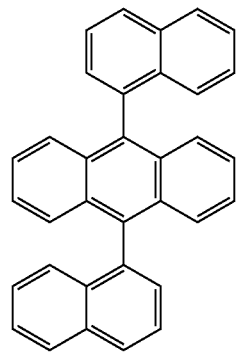 [SMILES: c1ccc2c(-c3c4ccccc4c(-c4cccc5ccccc45)c4ccccc34)cccc2c1]

In Chemical Formula B,

Ar4 and Ar5 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

In an exemplary embodiment, the organic material layer includes a light emitting layer, and the light emitting layer includes the compound represented by Chemical Formula B as a host of the light emitting layer.

In an exemplary embodiment of the present invention, Ar4 and Ar5 are the same as or different from each other, and are each independently a substituted or unsubstituted polycyclic aryl group.

In an exemplary embodiment, Ar4 and Ar5 are the same as or different from each other, and are each independently a substituted or unsubstituted naphthyl group.

In an exemplary embodiment of the present invention, Ar4 and Ar5 are the same as or different from each other, and are each independently a substituted or unsubstituted 2-naphthyl group.

According to an exemplary embodiment, Ar4 and Ar5 are a 2-naphthyl group.

In an exemplary embodiment, G1 to G8 are the same as or different from each other, and are each independently hydrogen; or a substituted or unsubstituted polycyclic aryl group.

According to an exemplary embodiment, G1 to G8 are the same as or different from each other, and are each independently hydrogen; or a substituted or unsubstituted polycyclic aryl group having 6 to 30 carbon atoms.

In an exemplary embodiment of the present invention, G1 to G8 are the same as or different from each other, and are each independently hydrogen; or a substituted or unsubstituted naphthyl group.

In an exemplary embodiment, G1 to G8 are the same as or different from each other, and are each independently hydrogen; or a naphthyl group unsubstituted or substituted with an aryl group.

In an exemplary embodiment, G1 to G8 are the same as or different from each other, and are each independently hydrogen; or a naphthyl group substituted with a 9-phenylanthracenyl group.

In an exemplary embodiment of the present invention, Chemical Formula B is selected from the following compound.

In an exemplary embodiment, the organic material layer includes a light emitting layer, and the light emitting layer comprises the compound represented by Chemical Formula A as a dopant of the light emitting layer, and comprises the compound represented by Chemical Formula B as a host of the light emitting layer.

According to an exemplary embodiment of the present specification, the organic material layer further comprises a hole injection layer or a hole transport layer, which includes a compound including an arylamino group, a carbazolyl group, or a benzocarbazolyl group, in addition to the organic material layer comprising the compound.

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is exemplified in FIGS. 1 and 2.

FIG. 1 exemplifies a structure of an organic electronic device in which a substrate (1), a positive electrode (2), a light emitting layer (3), and a negative electrode (4) are sequentially stacked. In the structure as described above, the compound may be comprised in the light emitting layer (3).

FIG. 2 exemplifies a structure of an organic electronic device composed of a substrate (1), a positive electrode (2), a hole injection layer (5), a hole transport layer (6), a light emitting layer (7), an electron transport layer (8), and a negative electrode (4).

In the structure as described above, the compound may be comprised in one or more layers of the hole injection layer, the hole transport layer, the light emitting layer, the electron transport layer, and the electron injection layer.

The organic light emitting device of the present specification may be manufactured by the materials and methods known in the art, except that one or more layers of the organic material layers comprise the compound of the present application, that is, the compound.

When the organic light emitting device comprises a plurality of organic material layers, the organic material layers may be formed of the same material or different materials.

The organic light emitting device of the present specification may be manufactured by the materials and methods known in the art, except that one or more layers of the organic material layers comprise the compound, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer comprising a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate. However, the manufacturing method is not limited thereto.

According to an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present specification include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer, and has a large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic electronic device according to the present specification may be a top emission type, a bottom emission type, or a dual emission type according to the material to be used.

According to an exemplary embodiment of the present specification, the compound may be included in an organic solar cell or an organic transistor in addition to the organic electronic device.

The compound according to the present specification may act by a principle similar to that applied to the organic light emitting device even in an organic electronic device including an organic phosphorescent device, an organic solar cell, an organic photoconductor, an organic transistor, and the like.

Hereinafter, the present specification will be described in detail with reference to Examples in order to specifically explain the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

PREPARATION EXAMPLES

<Synthesis Example 1>—Preparation of Compound 1

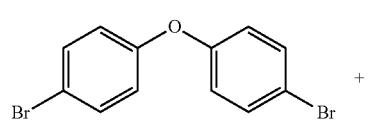

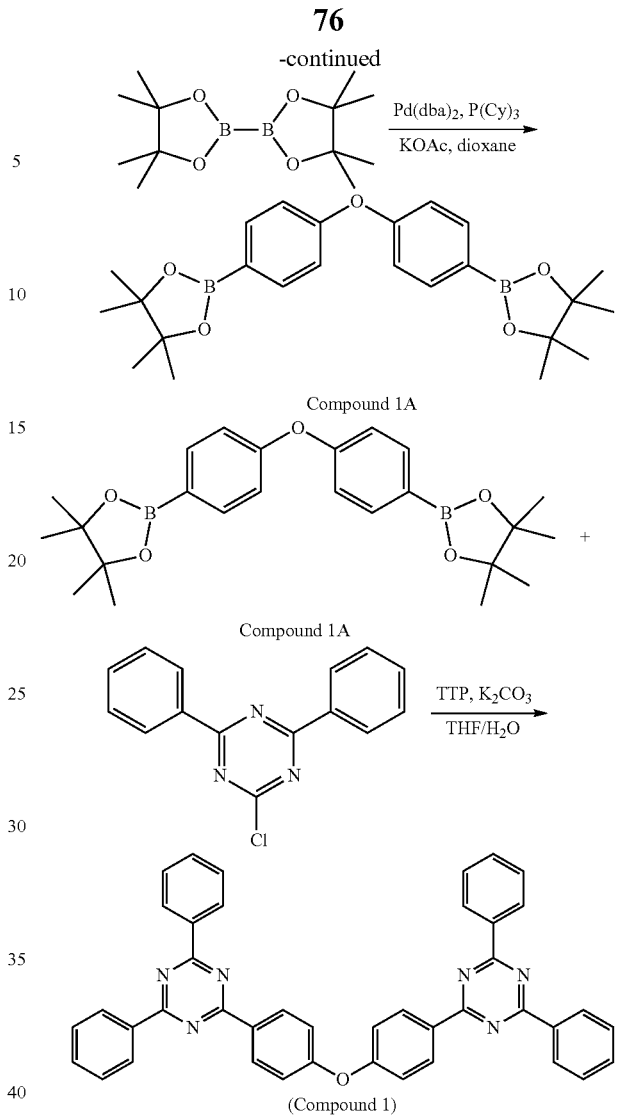

(1) Preparation of Compound 1A 4,4'-oxy(bromobenzene) (20.0 g, 60.98 mmol), bis(pinacolato)diboron (37.2 g, 146.34 mmol), and potassium acetate (35.9 g, 365.85 mmol) were mixed under a nitrogen atmosphere, and the resulting mixture was added to 200 ml of dioxane, and heated while being stirred. Bis(dibenzylideneacetone)palladium (2.1 g, 3.66 mmol) and tricyclohexylphosphine (2.1 mg, 7.32 mmol) were put into the mixture under reflux, and the resulting mixture was heated and stirred for 4 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 1A (23.8 g, 93%). The 4,4'-oxy(bromobenzene) was purchased from TCI, Co., Ltd.

(2) Preparation of Compound 1

Compound 1A (23.8 g, 56.58 mmol) and 2-chloro-4,6-diphenyl-1,3,5-triazine (30.2 g, 112.76 mmol) were put into 300 ml of tetrahydrofuran under a nitrogen atmosphere, and the resulting mixture was stirred and refluxed. Thereafter, potassium carbonate (46.8 g, 338.28 mmol) was dissolved in 150 ml of water, the resulting solution was introduced thereinto, the resulting mixture was sufficiently stirred, and then tetrakistriphenyl-phosphinopalladium (3.9 g, 3.38 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 1 (23.5 g, 66%). The 2-chloro-4,6-diphenyl-1,3,5-triazine was purchased from Alfa Aesar.

MS: [M+H]+=633

<Synthesis Example 2>—Preparation of Compound 2

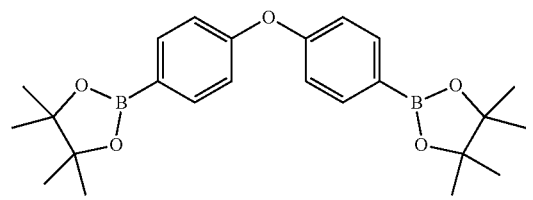

Molecular Weight: 422.13
Compound 1A

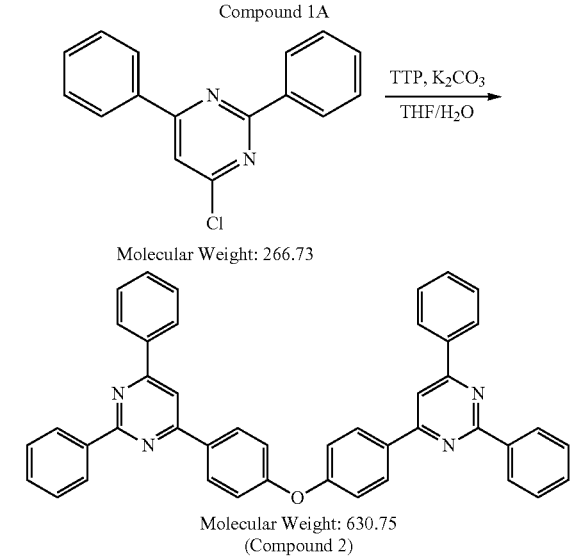

Molecular Weight: 266.73

Molecular Weight: 630.75
(Compound 2)

Compound 1A (30.0 g, 71.07 mmol) in Synthesis Example 1 and 4-chloro-2,6-diphenylpyrimidine (37.9 g, 142.14 mmol) were put into 400 ml of dioxane under a nitrogen atmosphere, and the resulting mixture was stirred and refluxed. Thereafter, potassium phosphate (90.5 g, 426.41 mmol) was dissolved in 150 ml of water, the resulting solution was introduced thereinto, the resulting mixture was sufficiently stirred, and then bis(dibenzylideneacetone)palladium (2.5 g, 4.26 mmol) and tricyclohexylphosphine (2.4 g, 8.52 mmol) were dissolved in dioxane, and the resulting solution was introduced thereinto. After the reaction for 24 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 2 (34.5 g, 77%). The 4-chloro-2,6-diphenylpyrimidine was purchased from Alfa Aesar. The following FIG. 3 is a view illustrating MS data values of Compound 2.

MS: [M+H]+=631

<Synthesis Example 3>—Preparation of Compound 3

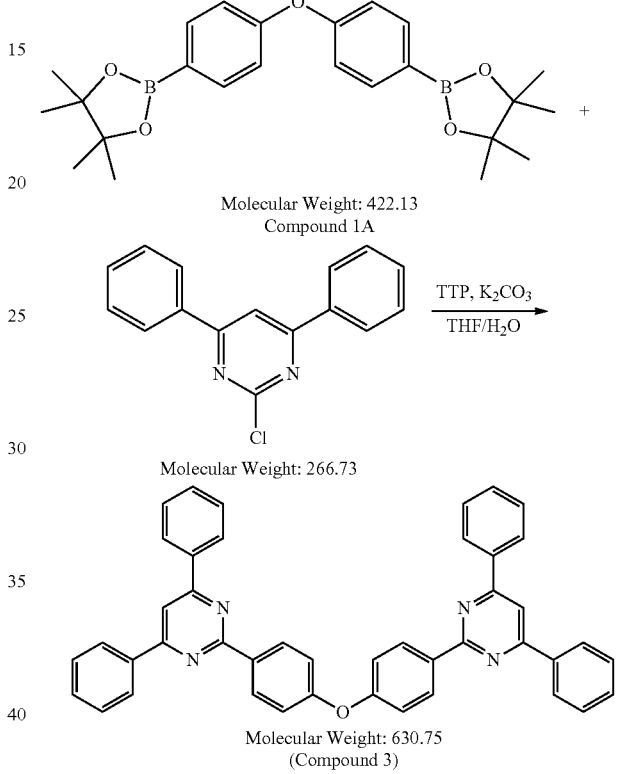

Molecular Weight: 422.13
Compound 1A

Molecular Weight: 266.73

Molecular Weight: 630.75
(Compound 3)

Compound 3 (26.0 g, yield 58%) was prepared in the same manner as in the preparation of Compound 2 in Synthesis Example 2, except that 2-chloro-2,6-diphenylpyrimidine was used instead of 4-chloro-2,6-diphenylpyrimidine. The following FIG. 4 is a view illustrating MS data values of Compound 3.

MS: [M+H]+=631

<Synthesis Example 4>—Preparation of Compound 4

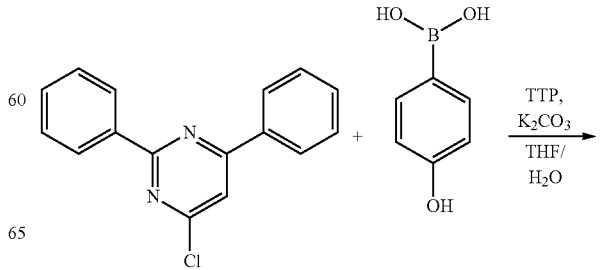

-continued

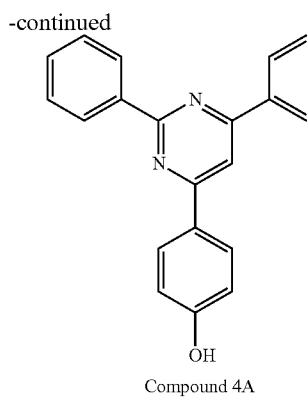
Compound 4A

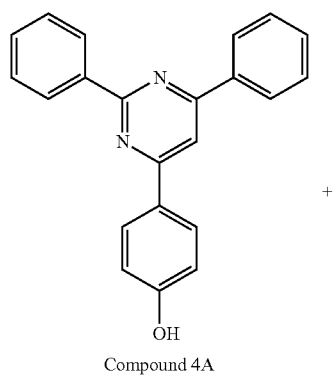
Compound 4A

+

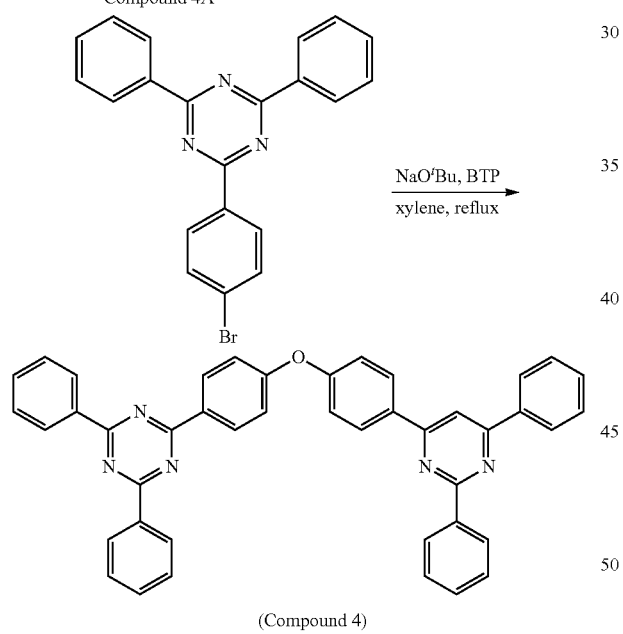
(Compound 4)

(1) Preparation of Compound 4A 4-chloro-2,6-diphenylpyrimidine (50.0 g, 187.46 mmol) and (4-hydroxyphenyl)boronic acid (31.0 g, 224.95 mmol) were put into 500 ml of tetrahydrofuran under a nitrogen atmosphere, and the resulting mixture was stirred and refluxed. Thereafter, potassium carbonate (31.1 g, 224.95 mmol) was dissolved in 100 ml of water, the resulting solution was introduced thereinto, the resulting mixture was sufficiently stirred, and then tetrakistriphenyl-phosphinopalladium (6.5 g, 5.62 mmol) was introduced thereinto. After the reaction for 8 hours, the temperature of the mixture was lowered to normal temperature, the organic layer and the aqueous layer were separated, and then the organic layer was distilled under reduced pressure. The organic layer was extracted with chloroform and water, and then the organic layer was dried by using magnesium sulfate. Thereafter, the organic layer was distilled under reduced pressure, and then recrystallized by using ethanol. The produced solid was filtered and then dried to prepare Compound 4A (29.2 g, 48%).

(2) Preparation of Compound 4

Compound 4A (29.2 g, 90.02 mmol), 2-(4-bromophenyl)-4,6-diphenyl-1,3,5-triazine (35.0 g, 90.02 mmol), and sodium t-butoxide (10.4 g, 108.02 mmol) were put into 300 ml of toluene under a nitrogen atmosphere, and the resulting mixture was stirred and refluxed. Thereafter, bis(tri-tert butylphosphine) palladium (1.4 g, 2.70 mmol) was introduced thereinto. After the reaction for 8 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 4 (23.3 g, 41%).

MS: [M+H]+=632

<Synthesis Example 5>—Preparation of Compound 5

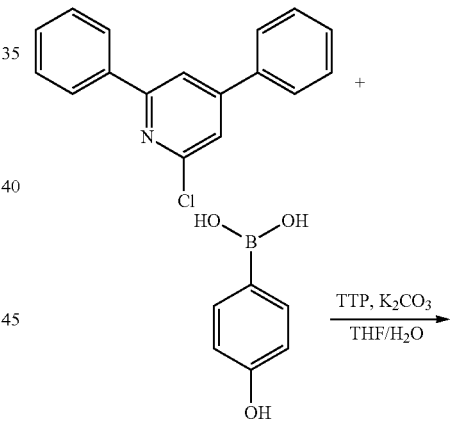

+

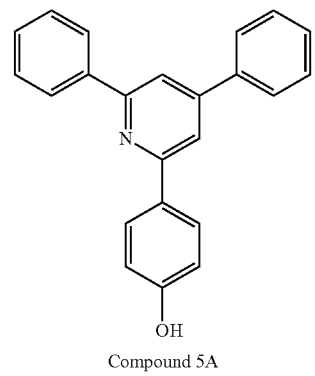
Compound 5A

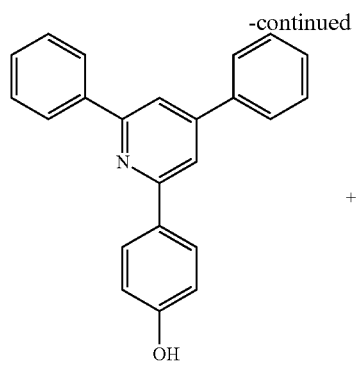

Compound 5A

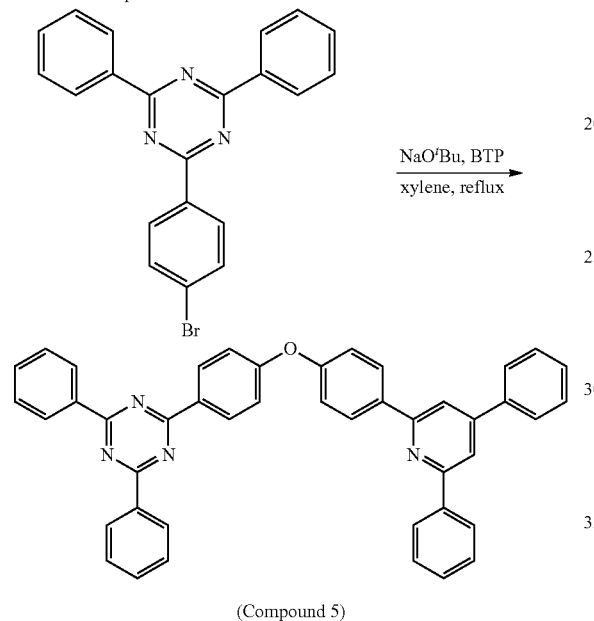

(Compound 5)

(1) Preparation of Compound 5A 2-chloro-4,6-diphenylpyridine (30.0 g, 112.89 mmol) and (4-hydroxyphenyl)boronic acid (18.7 g, 135.47 mmol) were put into 300 ml of tetrahydrofuran under a nitrogen atmosphere, and the resulting mixture was stirred and refluxed. Thereafter, potassium carbonate (18.7 g, 135.47 mmol) was dissolved in 80 ml of water, the resulting solution was introduced thereinto, the resulting mixture was sufficiently stirred, and then tetrakistriphenyl-phosphinopalladium (3.9 g, 3.39 mmol) was introduced thereinto. After the reaction for 12 hours, the temperature of the mixture was lowered to normal temperature, the organic layer and the aqueous layer were separated, and then the organic layer was distilled under reduced pressure. The organic layer was extracted with chloroform and water, and then the organic layer was dried by using magnesium sulfate. Thereafter, the organic layer was distilled under reduced pressure, and then recrystallized by using ethanol. The produced solid was filtered and then dried to prepare Compound 5A (23.3 g, 64%).

(2) Preparation of Compound 5

Compound 5A (23.3 g, 72.05 mmol), 2-(4-bromophenyl)-4,6-diphenyl-1,3,5-triazine (28.0 g, 72.05 mmol), and sodium t-butoxide (8.3 g, 86.46 mmol) were put into 300 ml of toluene under a nitrogen atmosphere, and the resulting mixture was stirred and refluxed. Thereafter, bis(tri-tert butylphosphine) palladium (1.1 g, 2.16 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 5 (23.3 g, 41%).

MS: [M+H]+=631

<Synthesis Example 6>—Preparation of Compound 6

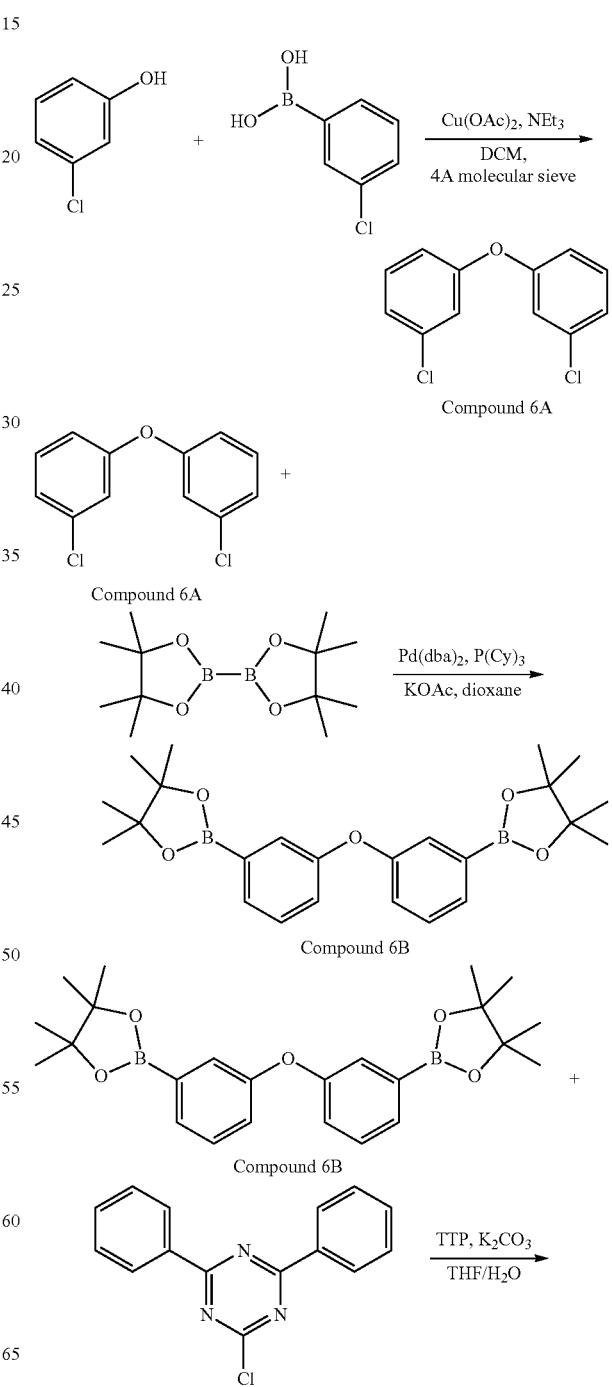

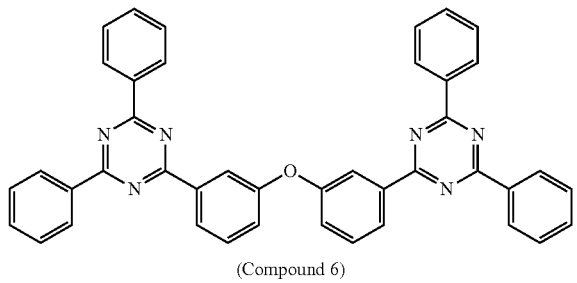

(Compound 6)

(1) Preparation of Compound 6A 3-chlorophenol (50.0 g, 388.92 mmol), (3-chlorophenyl)boronic acid (66.9 g, 408.37 mmol), and triethylamine (198.2 g, 1,944.62 mmol) were put into 500 ml of dichloromethane activated by a molecular sieve under a nitrogen atmosphere, and the resulting mixture was stirred. Thereafter, copper acetate (70.6 g, 388.92 mmol) was introduced thereinto. After the reaction for 12 hours, the mixture was filtered. The filtrate was extracted with ammonia water, and then the organic layer was dried by using magnesium sulfate. Thereafter, the organic layer was distilled under reduced pressure to prepare Compound 6A (84.6 g, 91%).

(2) Preparation of Compound 6B

Compound 6A (50.0 g, 209.12 mmol), bis(pinacolato)diboron (127.4 g, 501.88 mmol), and potassium acetate (123.1 g, 1,254.71 mmol) were mixed under a nitrogen atmosphere, and the resulting mixture was added to 600 ml of dioxane, and heated while being stirred. Bis(dibenzylideneacetone)palladium (7.2 g, 12.55 mmol) and tricyclohexylphosphine (7.0 mg, 25.09 mmol) were put into the mixture under reflux, and the resulting mixture was heated and stirred for 12 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 6B (76.8 g, 87%).

(3) Preparation of Compound 6

Compound 6B (20.0 g, 47.38 mmol) and 2-chloro-4,6-diphenyl-1,3,5-triazine (25.4 g, 96.76 mmol) were put into 200 ml of tetrahydrofuran under a nitrogen atmosphere, and the resulting mixture was stirred and refluxed. Thereafter, potassium carbonate (39.3 g, 284.27 mmol) was dissolved in 100 ml of water, the resulting solution was introduced thereinto, the resulting mixture was sufficiently stirred, and then tetrakistriphenyl-phosphinopalladium (3.3 g, 2.84 mmol) was introduced thereinto. After the reaction for 6 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 6 (22.2 g, 74%).

MS: [M+H]+=633

<Synthesis Example 7>—Preparation of Compound 7

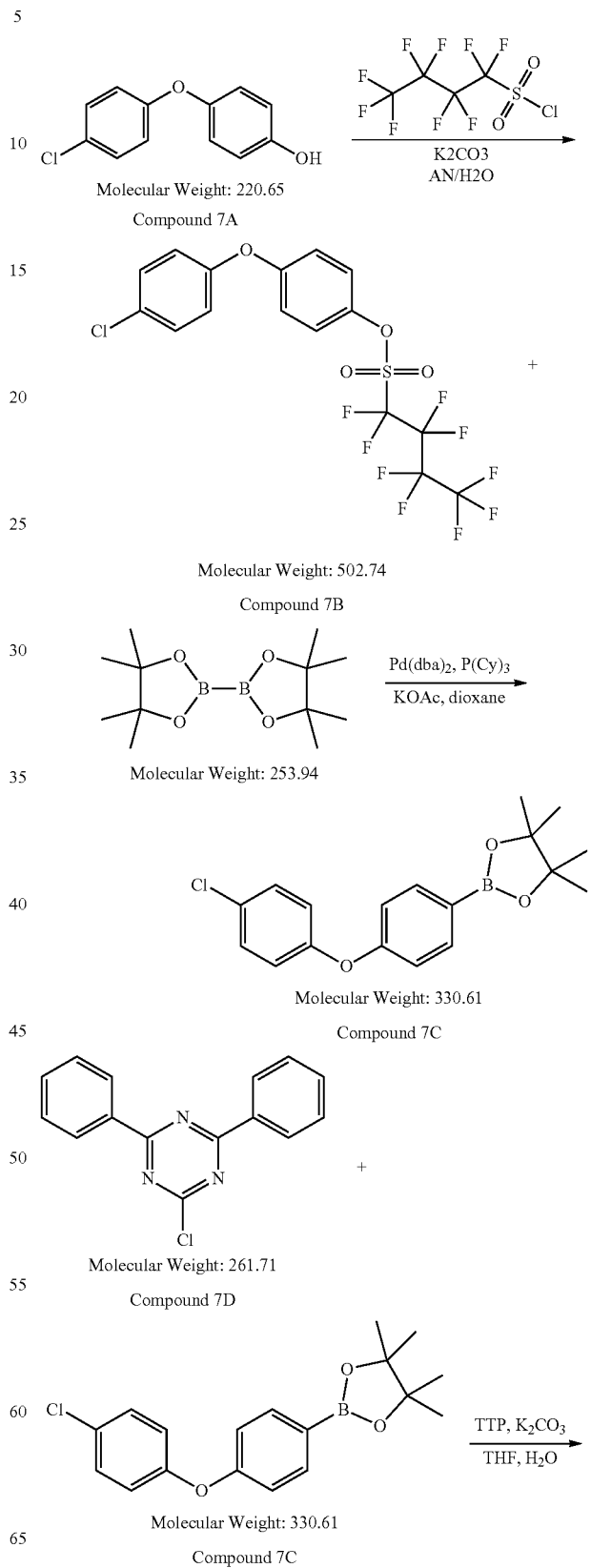

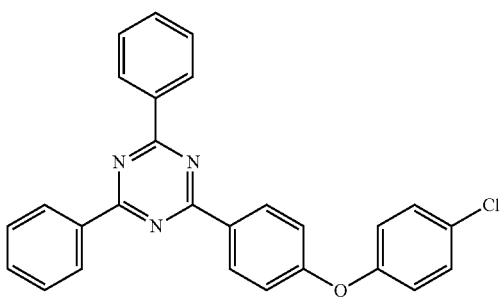

Molecular Weight: 435.90
Compound 7E

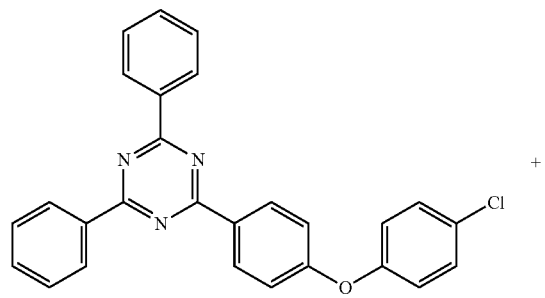

Molecular Weight: 435.90
Compound 7E

+

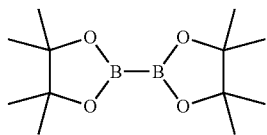

Molecular Weight: 253.94

Pd(dba)₂, P(Cy)₃
KOAc, dioxane
→

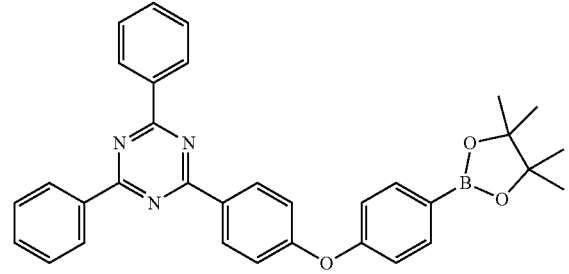

Molecular Weight: 527.42
Compound 7F

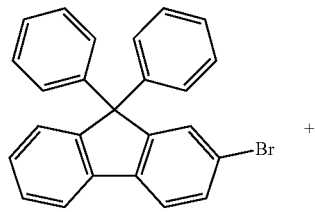

Molecular Weight: 397.32
Compound 7G

+

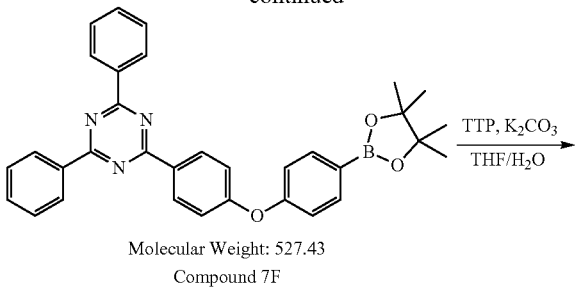

Molecular Weight: 527.43
Compound 7F

TTP, K₂CO₃
THF/H₂O
→

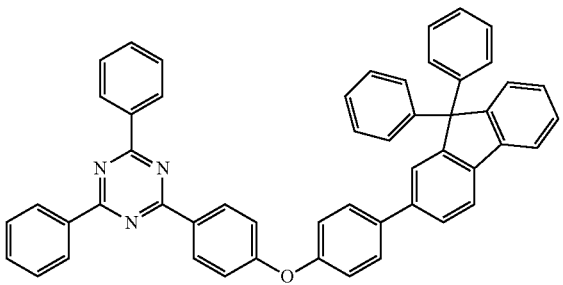

Molecular Weight: 717.87
(Compound 7)

(1) Preparation of Compound 7B 4-(4-chlorophenoxy)phenol (50.0 g, 226.60 mmol), 1,1,2,2,3,3,4,4,4-nonafluorobutane-1-sulfonyl chloride (102.7 g, 339.90 mmol), and potassium carbonate (62.6 g, 453.21 mmol) were put into 1,000 ml of acetonitrile and 300 ml of water, and the resulting mixture was stirred. After the reaction for 1 hour, the layers were separated, and then the organic layer was dried by using magnesium sulfate. Thereafter, the organic layer was distilled under reduced pressure to prepare Compound 7B (108.2 g, 95%).

(2) Preparation of Compound 7C

Compound 7A (113.9 g, 448.53 mmol), bis(pinacolato)diboron (125.3 g, 494.38 mmol), and potassium acetate (132.1 g, 1,346 mmol) were mixed under a nitrogen atmosphere, and the resulting mixture was added to 1,000 ml of tetrahydrofuran, and heated while being stirred. Bis(dibenzylideneacetone)palladium (7.2 g, 12.55 mmol) and tricyclohexylphosphine (7.0 mg, 25.09 mmol) were put into the mixture under reflux, and the resulting mixture was heated and stirred for 12 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 7C (95.1 g, 64%).

(3) Preparation of Compound 7E

Compound 7C (95.1 g, 288 mmol) and 2-chloro-4,6-diphenyl-1,3,5-triazine (7D, 70 g, 261 mmol) were put into 1,000 ml of tetrahydrofuran under a nitrogen atmosphere, and the resulting mixture was stirred and refluxed. Thereafter, potassium carbonate (108.4 g, 784 mmol) was dissolved in 500 ml of water, the resulting solution was introduced thereinto, the resulting mixture was sufficiently stirred, and then tetrakistriphenyl-phosphinopalladium (9.7 g, 8 mmol) was introduced thereinto. After the reaction for 6 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 7E (87.8 g, 77%).

(4) Preparation of Compound 7F

Compound 7E (87.8 g, 201 mmol), bis(pinacolato)diboron (56.3 g, 222 mmol), and potassium acetate (59.3 g, 604 mmol) were mixed under a nitrogen atmosphere, and the resulting mixture was added to 600 ml of tetrahydrofuran, and heated while being stirred. Bis(dibenzylideneacetone) palladium (3.5 g, 6 mmol) and tricyclohexylphosphine (3.4 mg, 12 mmol) were put into the mixture under reflux, and the resulting mixture was heated and stirred for 12 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 7F (93.5 g, 88%).

(5) Preparation of Compound 7

Compound 7G (7 g, 18 mmol) and Compound 7F (10.2 g, 19 mmol) were put into 100 ml of tetrahydrofuran under a nitrogen atmosphere, and the resulting mixture was stirred and refluxed. Thereafter, potassium carbonate (7.3 g, 58 mmol) was dissolved in 30 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 7 (7.7 g, 61%).

<Synthesis Example 8>—Preparation of Compound 8

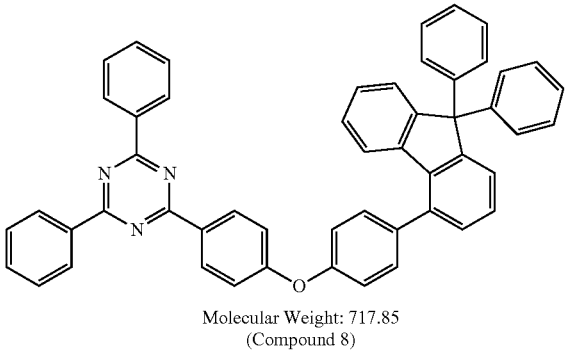

Molecular Weight: 717.85
(Compound 8)

(1) Preparation of Compound 8

Compound 8A (7 g, 18 mmol) and Compound 7F (10.2 g, 19 mmol) were put into 100 ml of tetrahydrofuran under a nitrogen atmosphere, and the resulting mixture was stirred and refluxed. Thereafter, potassium carbonate (7.3 g, 58 mmol) was dissolved in 30 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 8 (7.5 g, 59%).

<Synthesis Example 9>—Preparation of Compound 9

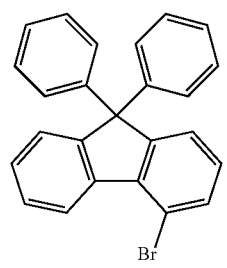

Molecular Weight: 397.31
Compound 8A

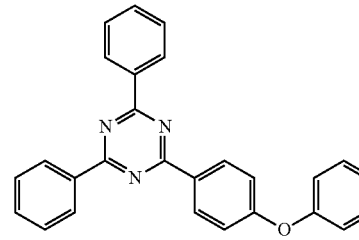

Molecular Weight: 527.42
Compound 7F

TTP, K$_2$CO$_3$
THF/H$_2$O

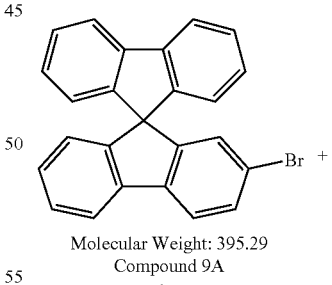

Molecular Weight: 395.29
Compound 9A

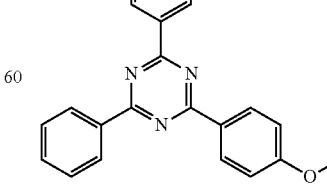

Molecular Weight: 527.42
Compound 7F

TTP, K$_2$CO$_3$
THF/H$_2$O

-continued

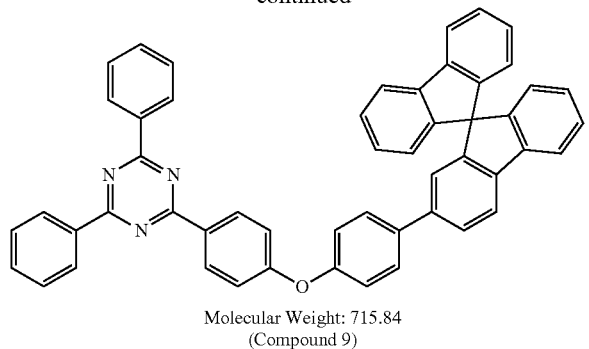

Molecular Weight: 715.84
(Compound 9)

(1) Preparation of Compound 9

Compound 9A (7 g, 19 mmol) and Compound 7F (10.3 g, 19 mmol) were put into 100 ml of tetrahydrofuran under a nitrogen atmosphere, and the resulting mixture was stirred and refluxed. Thereafter, potassium carbonate (7.3 g, 53 mmol) was dissolved in 30 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 9 (7.2 g, 57%).

<Synthesis Example 10>—Preparation of Compound 10

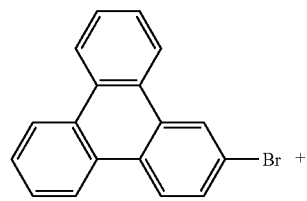

Molecular Weight: 307.18
Compound 10A

-continued

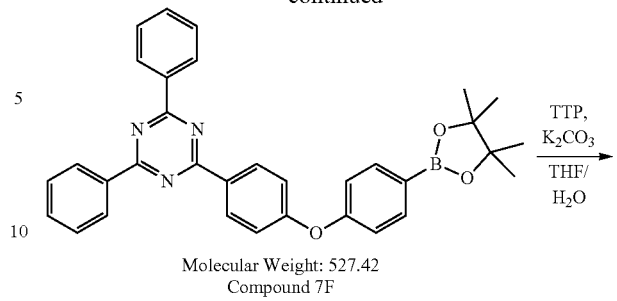

Molecular Weight: 527.42
Compound 7F

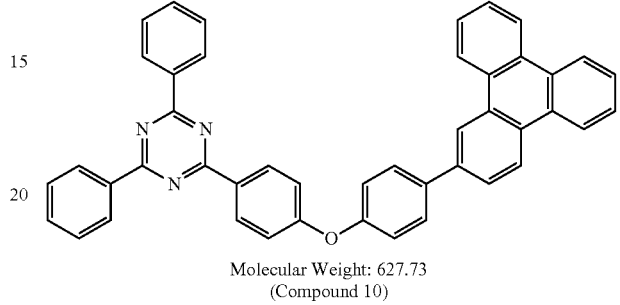

Molecular Weight: 627.73
(Compound 10)

(1) Preparation of Compound 10

Compound 10A (7 g, 23 mmol) and Compound 7F (13.2 g, 26 mmol) were put into 100 ml of tetrahydrofuran under a nitrogen atmosphere, and the resulting mixture was stirred and refluxed. Thereafter, potassium carbonate (9.4 g, 68 mmol) was dissolved in 30 ml of water, the resulting solution was introduced thereinto, the resulting mixture was sufficiently stirred, and then tetrakistriphenyl-phosphinopalladium (0.5 g, 0.5 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 10 (11.6 g, 81%).

<Synthesis Example 11>—Preparation of Compound 11

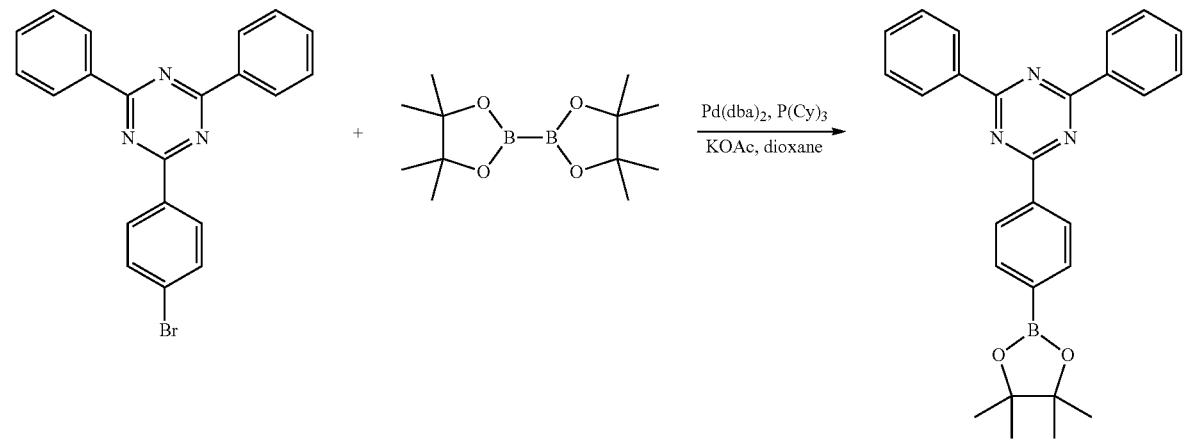

Compound 11A

-continued
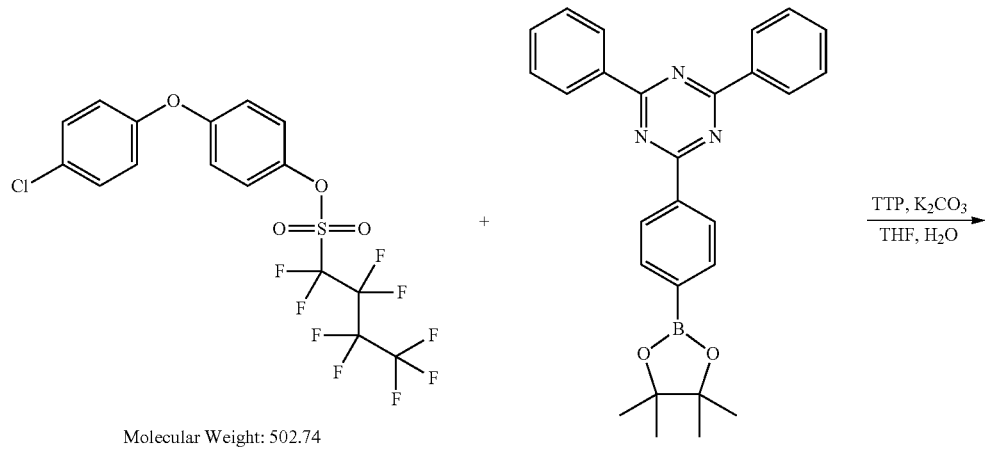
Molecular Weight: 502.74
Compound 7B
Molecular Weight: 435.33
Compound 11A
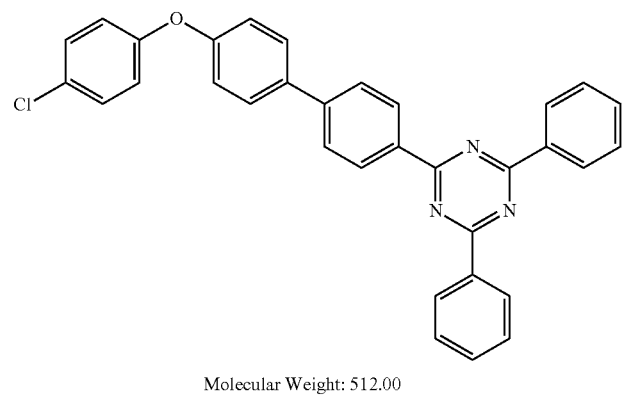
Molecular Weight: 512.00
Compound 11B
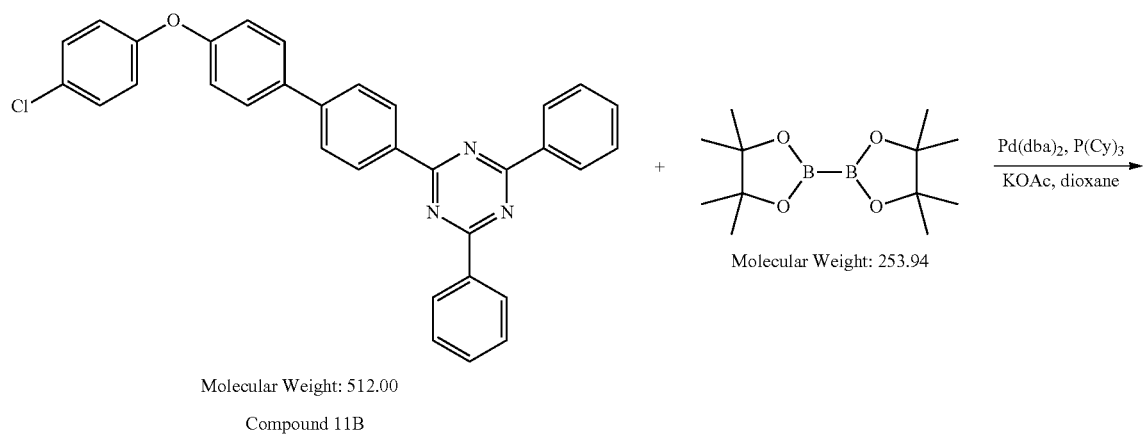
Molecular Weight: 512.00
Compound 11B
Molecular Weight: 253.94

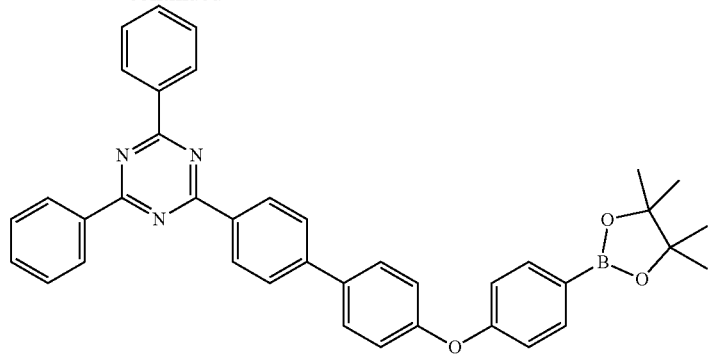

Molecular Weight: 603.52

Compound 11C

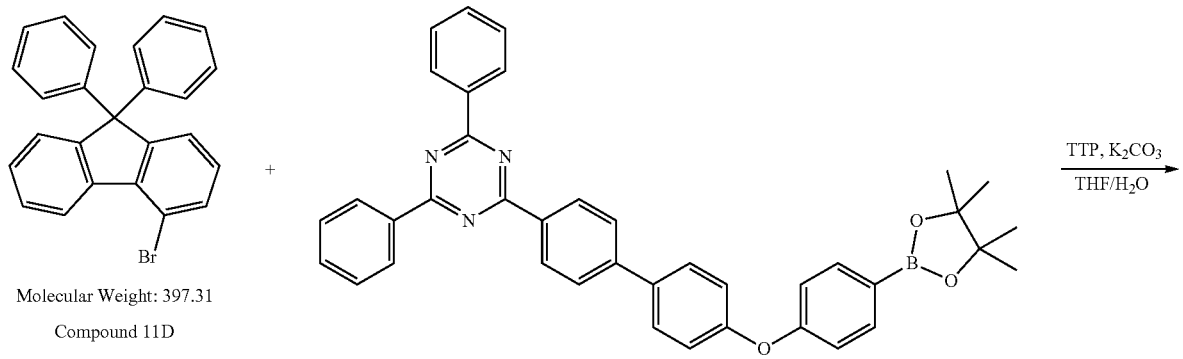

Molecular Weight: 397.31

Compound 11D

Molecular Weight: 603.52

Compound 11C

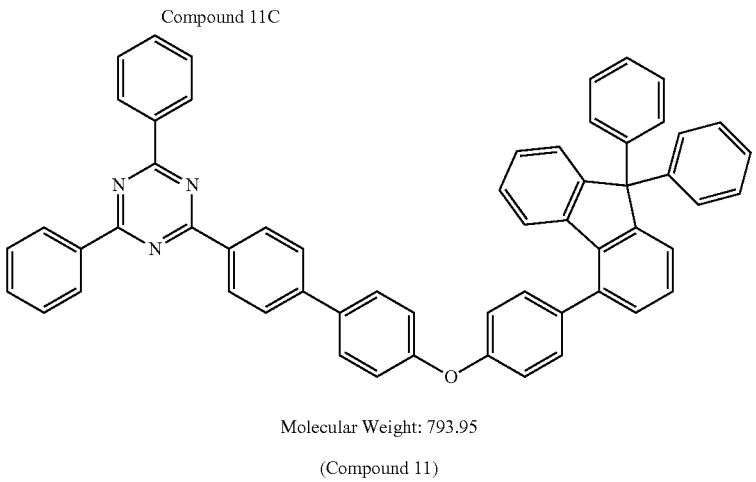

Molecular Weight: 793.95

(Compound 11)

(1) Preparation of Compound 11A 2-(4-bromophenyl)-4,6-diphenyl-1,3,5-triazine (20.0 g, 51.51 mmol), bis(pinacolato)diboron (14.4 g, 56.66 mmol), and potassium acetate (15.2 g, 154.53 mmol) were mixed under a nitrogen atmosphere, and the resulting mixture was added to 300 ml of dioxane, and heated while being stirred. Bis(dibenzylideneacetone)palladium (0.9 g, 1.55 mmol) and tricyclohexylphosphine (0.9 g, 1.55 mmol) were put into the mixture under reflux, and the resulting mixture was heated and stirred for 4 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 11A (20.0 g, 90%).

(2) Preparation of Compound 11B

Compound 7B (21 g, 42 mmol) and Compound 11A (20 g, 46 mmol) were put into 300 ml of tetrahydrofuran under a nitrogen atmosphere, and the resulting mixture was stirred and refluxed. Thereafter, potassium carbonate (17.3 g, 125 mmol) was dissolved in 100 ml of water, the resulting solution was introduced thereinto, the resulting mixture was sufficiently stirred, and then tetrakistriphenyl-phosphinopalladium (1.4 g, 1 mmol) was introduced thereinto. After the reaction for 9 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 11B (19.4 g, 77%).

(3) Preparation of Compound 11C

Compound 11B (19.4 g, 38 mmol), bis(pinacolato)diboron (10.6 g, 42 mmol), and potassium acetate (11.2 g, 114 mmol) were mixed under a nitrogen atmosphere, and the resulting mixture was added to 200 ml of tetrahydrofuran, and heated while being stirred. Bis(dibenzylideneacetone)palladium (0.7 g, 1 mmol) and tricyclohexylphosphine (0.7 mg, 2 mmol) were put into the mixture under reflux, and the resulting mixture was heated and stirred for 12 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 11C (20.8 g, 91%).

(4) Preparation of Compound 11

Compound 11D (7 g, 18 mmol) and Compound 11C (10.2 g, 19 mmol) were put into 200 ml of tetrahydrofuran under a nitrogen atmosphere, and the resulting mixture was stirred and refluxed. Thereafter, potassium carbonate (7.3 g, 53 mmol) was dissolved in 100 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 5 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 11 (6.9 g, 49%).

<Synthesis Example 12>—Preparation of Compound 12

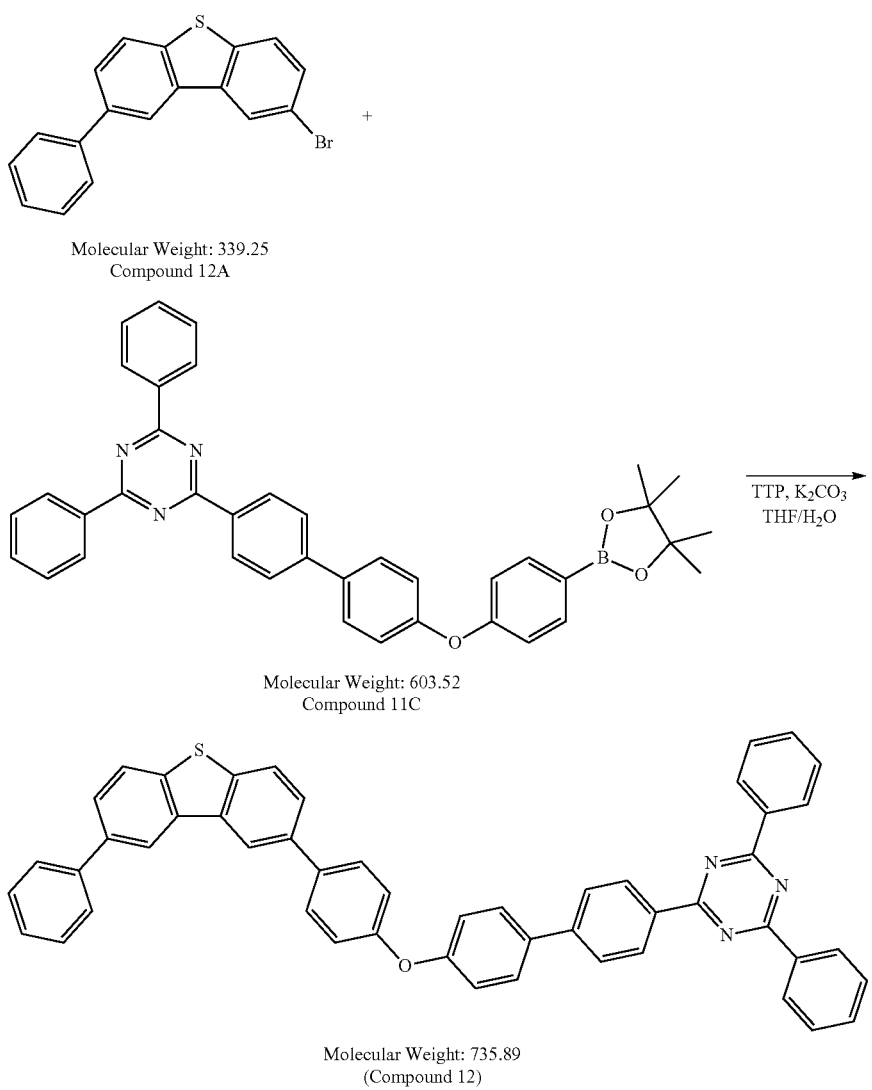

(1) Preparation of Compound 12

Compound 12A (10 g, 29 mmol) and Compound 11C (19.6 g, 32 mmol) were put into 200 ml of tetrahydrofuran under a nitrogen atmosphere, and the resulting mixture was stirred and refluxed. Thereafter, potassium carbonate (12.2 g, 88 mmol) was dissolved in 60 ml of water, the resulting solution was introduced thereinto, the resulting mixture was sufficiently stirred, and then tetrakistriphenyl-phosphinopalladium (1 g, 0.9 mmol) was introduced thereinto. After the reaction for 7 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 12 (7.3 g, 37%).

<Synthesis Example 13>—Preparation of Compound 13

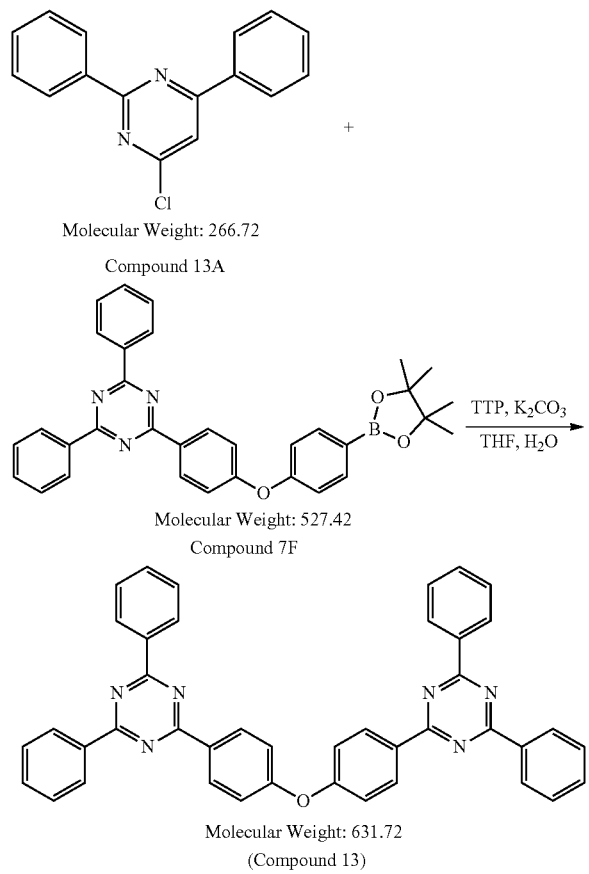 [SMILES: Clc1cc(-c2ccccc2)nc(-c2ccccc2)n1 ; CC1(C)OB(c2ccc(Oc3ccc(-c4nc(-c5ccccc5)nc(-c5ccccc5)n4)cc3)cc2)OC1(C)C ; c1ccc(-c2nc(-c3ccccc3)nc(-c3ccc(Oc4ccc(-c5nc(-c6ccccc6)nc(-c6ccccc6)n5)cc4)cc3)n2)cc1]

(1) Preparation of Compound 13

Compound 13A (7 g, 20 mmol) and Compound 7F (10.3 g, 20 mmol) were put into 100 ml of tetrahydrofuran under a nitrogen atmosphere, and the resulting mixture was stirred and refluxed. Thereafter, potassium carbonate (8.1 g, 59 mmol) was dissolved in 30 ml of water, the resulting solution was introduced thereinto, the resulting mixture was sufficiently stirred, and then tetrakistriphenyl-phosphinopalladium (0.7 g, 0.6 mmol) was introduced thereinto. After the reaction for 19 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 13 (9.4 g, 71%).

<Synthesis Example 14>—Preparation of Compound 14

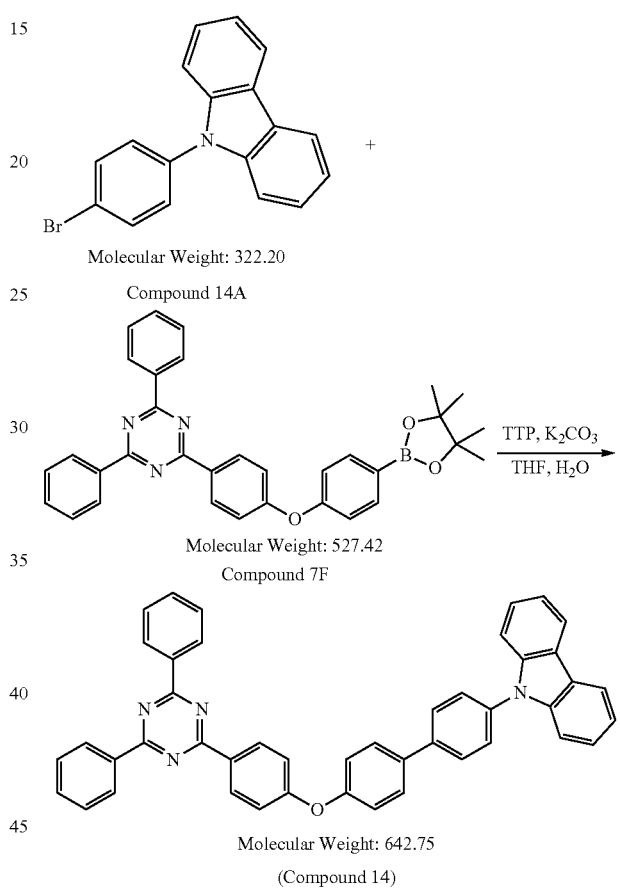

(1) Preparation of Compound 14

Compound 14A (7 g, 27 mmol) and Compound 7F (15 g, 28 mmol) were put into 100 ml of tetrahydrofuran under a nitrogen atmosphere, and the resulting mixture was stirred and refluxed. Thereafter, potassium carbonate (11.2 g, 81 mmol) was dissolved in 30 ml of water, the resulting solution was introduced thereinto, the resulting mixture was sufficiently stirred, and then tetrakistriphenyl-phosphinopalladium (0.9 g, 0.8 mmol) was introduced thereinto. After the reaction for 9 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 14 (8.5 g, 54%).

<Synthesis Example 15>—Preparation of Compound 15

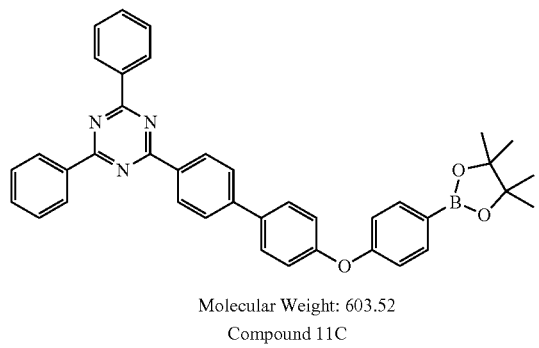

Molecular Weight: 603.52
Compound 11C

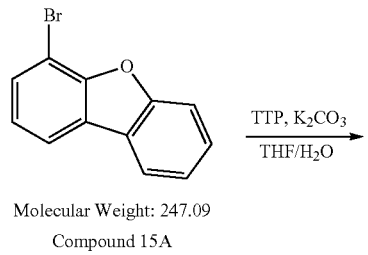

Molecular Weight: 247.09
Compound 15A

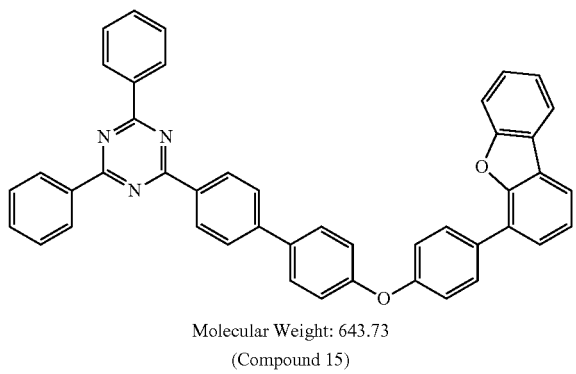

Molecular Weight: 643.73
(Compound 15)

(1) Preparation of Compound 15

Compound 15A (4.1 g, 17 mmol) and Compound 11C (10 g, 17 mmol) were put into 100 ml of tetrahydrofuran under a nitrogen atmosphere, and the resulting mixture was stirred and refluxed. Thereafter, potassium carbonate (6.9 g, 50 mmol) was dissolved in 30 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 11 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 15 (5.0 g, 47%).

<Synthesis Example 16>—Preparation of Compound 16

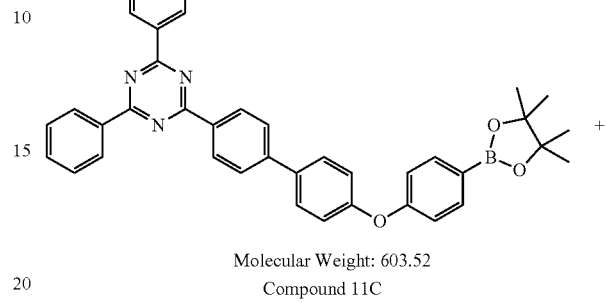

Molecular Weight: 603.52
Compound 11C

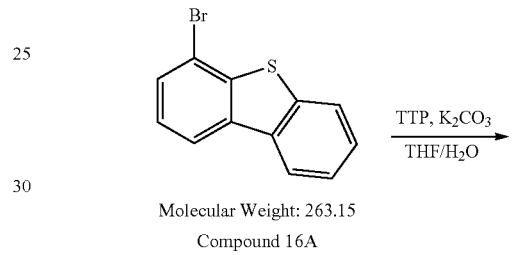

Molecular Weight: 263.15
Compound 16A

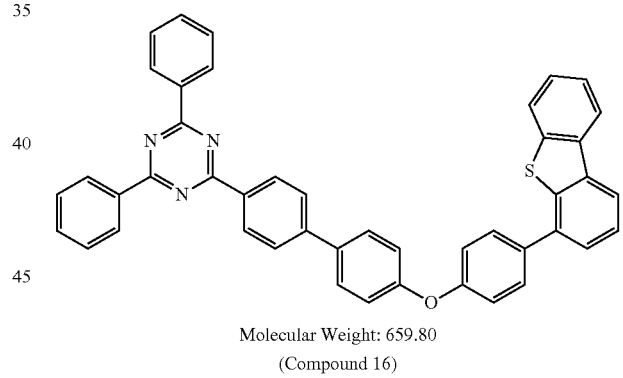

Molecular Weight: 659.80
(Compound 16)

(1) Preparation of Compound 16

Compound 16A (4.4 g, 17 mmol) and Compound 11C (10 g, 17 mmol) were put into 100 ml of tetrahydrofuran under a nitrogen atmosphere, and the resulting mixture was stirred and refluxed. Thereafter, potassium carbonate (6.9 g, 50 mmol) was dissolved in 30 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 11 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 16 (4.3 g, 39%).

<Synthesis Example 17>—Preparation of Compound 17

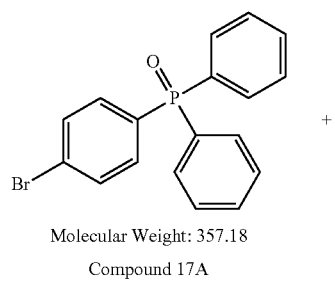

Molecular Weight: 357.18
Compound 17A

+

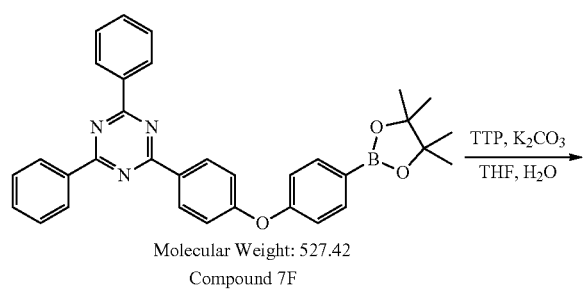

Molecular Weight: 527.42
Compound 7F

TTP, K₂CO₃
THF, H₂O

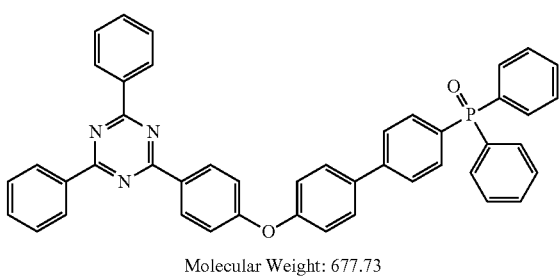

Molecular Weight: 677.73
(Compound 17)

(1) Preparation of Compound 17

Compound 17A (5.4 g, 15 mmol) and Compound 7F (8 g, 15 mmol) were put into 100 ml of tetrahydrofuran under a nitrogen atmosphere, and the resulting mixture was stirred and refluxed. Thereafter, potassium carbonate (6.3 g, 45 mmol) was dissolved in 20 ml of water, the resulting solution was introduced thereinto, the resulting mixture was sufficiently stirred, and then tetrakistriphenyl-phosphinopalladium (0.5 g, 0.5 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 17 (6.3 g, 61%).

<Synthesis Example 18>—Preparation of Compound 18

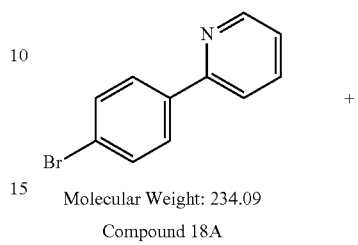

Molecular Weight: 234.09
Compound 18A

+

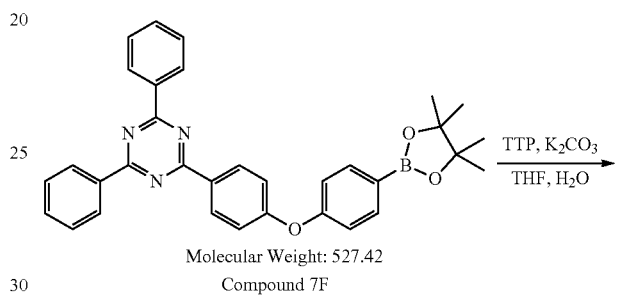

Molecular Weight: 527.42
Compound 7F

TTP, K₂CO₃
THF, H₂O

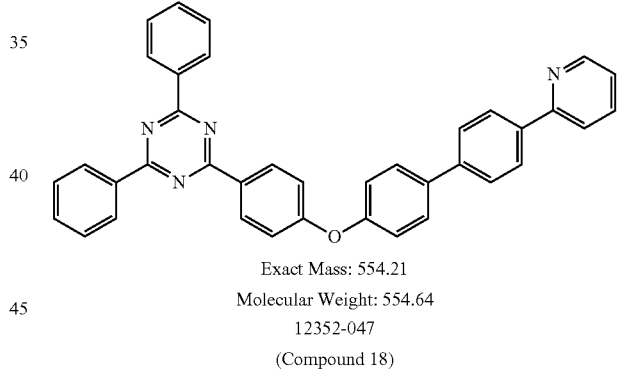

Exact Mass: 554.21
Molecular Weight: 554.64
12352-047
(Compound 18)

(1) Preparation of Compound 18

Compound 18A (6.0 g, 26 mmol) and Compound 7F (14.2 g, 27 mmol) were put into 200 ml of tetrahydrofuran under a nitrogen atmosphere, and the resulting mixture was stirred and refluxed. Thereafter, potassium carbonate (10.6 g, 77 mmol) was dissolved in 50 ml of water, the resulting solution was introduced thereinto, the resulting mixture was sufficiently stirred, and then tetrakistriphenyl-phosphinopalladium (0.9 g, 0.8 mmol) was introduced thereinto. After the reaction for 18 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 18 (9.4 g, 66%).

<Synthesis Example 19>—Preparation of Compound 19

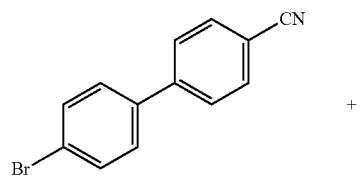

Molecular Weight: 258.11
Compound 19A

+

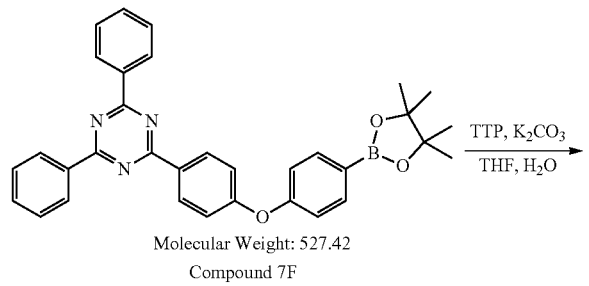

Molecular Weight: 527.42
Compound 7F

→ TTP, K₂CO₃ / THF, H₂O

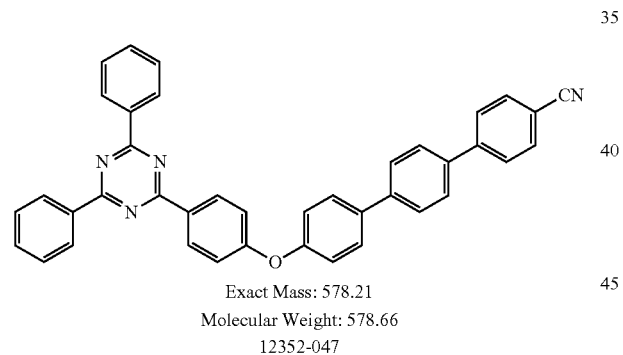

Exact Mass: 578.21
Molecular Weight: 578.66
12352-047
(Compound 19)

(1) Preparation of Compound 19

Compound 19A (7.0 g, 27 mmol) and Compound 7F (15 g, 28 mmol) were put into 200 ml of tetrahydrofuran under a nitrogen atmosphere, and the resulting mixture was stirred and refluxed. Thereafter, potassium carbonate (11.2 g, 82 mmol) was dissolved in 50 ml of water, the resulting solution was introduced thereinto, the resulting mixture was sufficiently stirred, and then tetrakistriphenyl-phosphinopalladium (0.9 g, 0.8 mmol) was introduced thereinto. After the reaction for 18 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 19 (8.0 g, 51%).

<Synthesis Example 20>—Preparation of Compound Represented by Comparative Example 1

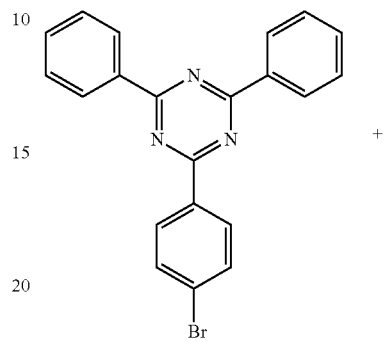

+

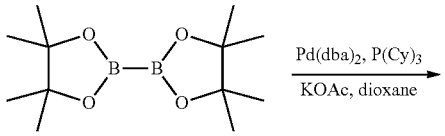

Pd(dba)₂, P(Cy)₃ / KOAc, dioxane

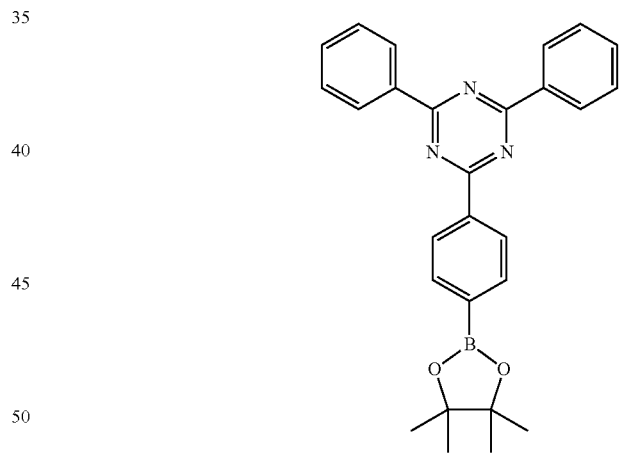

Compound 20A

+

-continued

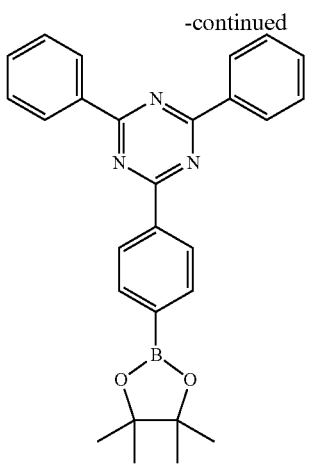

Compound 20A

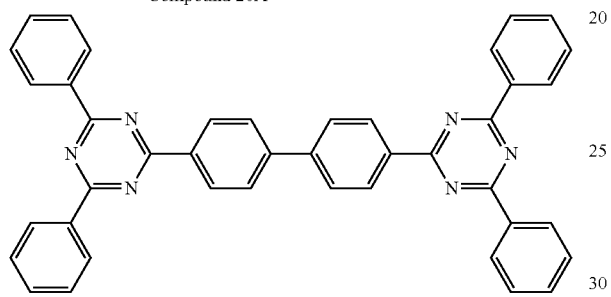

(Comparative Example 1)

(1) Preparation of Compound 20A 2-(4-bromophenyl)-4,6-diphenyl-1,3,5-triazine (20.0 g, 51.51 mmol), bis(pinacolato)diboron (14.4 g, 56.66 mmol), and potassium acetate (15.2 g, 154.53 mmol) were mixed under a nitrogen atmosphere, and the resulting mixture was added to 300 ml of dioxane, and heated while being stirred. Bis(dibenzylideneacetone)palladium (0.9 g, 1.55 mmol) and tricyclohexylphosphine (0.9 g, 1.55 mmol) were put into the mixture under reflux, and the resulting mixture was heated and stirred for 4 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 20A (20.0 g, 90%).

(2) Preparation of Compound Represented by Comparative Example 1

Compound 20A (20.0 g, 47.38 mmol) and 2-(4-bromophenyl)-4,6-diphenyl-1,3,5-triazine (17.8 g, 45.84 mmol) were put into 300 ml of tetrahydrofuran under a nitrogen atmosphere, and the resulting mixture was stirred and refluxed. Thereafter, potassium carbonate (38.0 g, 275.07 mmol) was dissolved in 100 ml of water, the resulting solution was introduced thereinto, the resulting mixture was sufficiently stirred, and then tetrakistriphenyl-phosphinopalladium (3.2 g, 2.75 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered, and then dried to prepare a compound represented by Comparative Example 1 (15.6 g, 55%).

MS: [M+H]+=616

<Synthesis Example 21>—Preparation of Compound Represented by Comparative Example 2

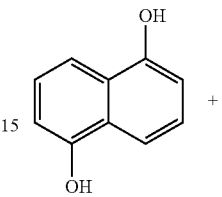

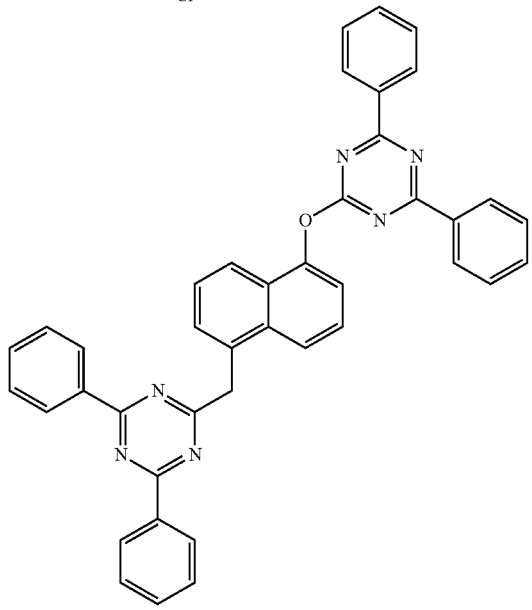

(Comparative Example 2)

Naphthalene-1,5-diol (5.0 g, 31.22 mmol) and 2-chloro-4,6-diphenyl-1,3,5-triazine (18.3 g, 68.68 mmol) were put into 100 ml of tetrahydrofuran under a nitrogen atmosphere, and the resulting mixture was stirred and refluxed. Thereafter, potassium carbonate (18.4 g, 187.30 mmol) was dissolved in 50 ml of water, and then the resulting solution was introduced thereinto, the resulting mixture was sufficiently stirred, and after the reaction for 4 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered, and then dried to prepare a compound represented by Comparative Example 2 (11.9 g, 61%).

MS: [M+H]+=621

<Synthesis Example 22>—Preparation of Compound Represented by Compound 3

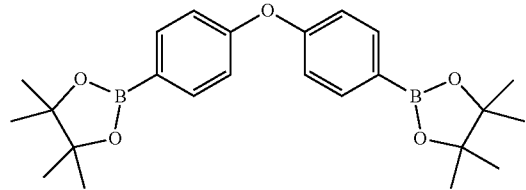

Compound 1A

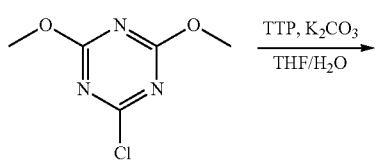

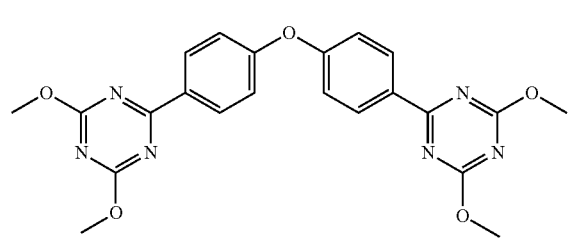

(Comparative Example 3)

A compound (17.0 g, yield 74%) represented by Comparative Example 3 was prepared in the same manner as in the preparation of Compound 1 in Synthesis Example 1, except that 2-chloro-4,6-dimethoxy-1,3,5-triazine was used instead of 2-chloro-4,6-diphenyl-1,3,5-triazine.

MS: [M+H]+=484

<Synthesis Example 23>—Preparation of Compound Represented by Comparative Example 4

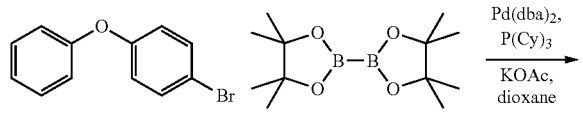

Molecular Weight: 249.10
Compound 16A

Molecular Weight: 253.94

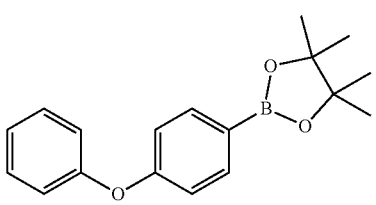

Molecular Weight: 296.17
Compound 16B

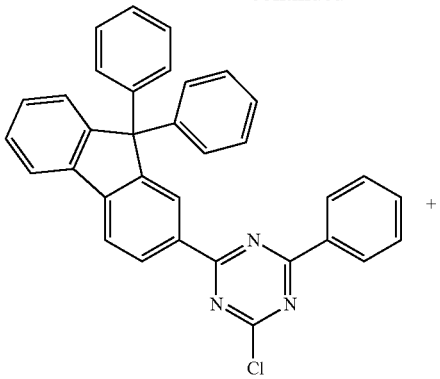

Molecular Weight: 508.01
Compound 16C

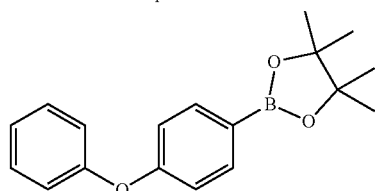

Molecular Weight: 296.17
Compound 16B

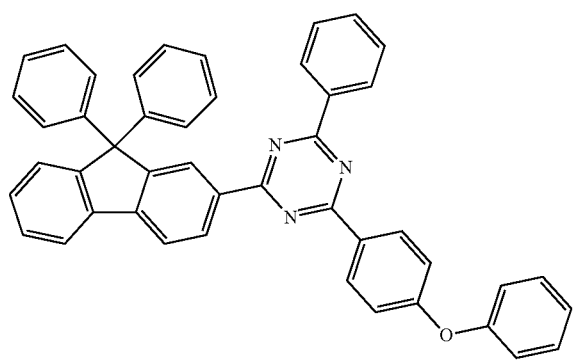

Molecular Weight: 641.76
(Comparative Example 4)

(1) Preparation of Compound 16B 1-bromo-4-phenoxybenzene (10.0 g, 40 mmol), bis(pinacolato)diboron (11.2 g, 44 mmol), and potassium acetate (11.8 g, 120 mmol) were mixed under a nitrogen atmosphere, and the resulting mixture was added to 100 ml of dioxane, and heated while being stirred. Bis(dibenzylideneacetone)palladium (0.7 g, 1 mmol) and tricyclohexylphosphine (0.7 g, 2 mmol) were put into the mixture under reflux, and the resulting mixture was heated and stirred for 12 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 16B (5.8 g, 49%).

(2) Preparation of Comparative Example 4 Compound 16C (9 g, 18 mmol) and Compound 16B (5.8 g, 19 mmol)

were put into 100 ml of tetrahydrofuran under a nitrogen atmosphere, and the resulting mixture was stirred and refluxed. Thereafter, potassium carbonate (7.3 g, 53 mmol) was dissolved in 30 ml of water, the resulting solution was introduced thereinto, the resulting mixture was sufficiently stirred, and then tetrakistriphenyl-phosphinopalladium (0.6 g, 0.5 mmol) was introduced thereinto. After the reaction for 7 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Comparative Example 4 (9.6 g, 84%).

<Synthesis Example 24>—Preparation of Compound Represented by Comparative Example 5

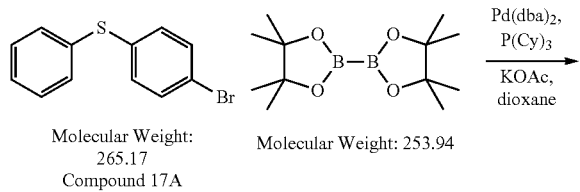

Molecular Weight: 265.17
Compound 17A

Molecular Weight: 253.94

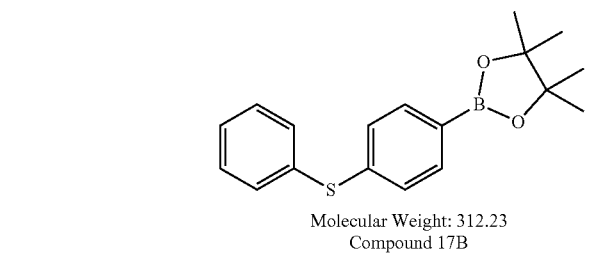

Molecular Weight: 312.23
Compound 17B

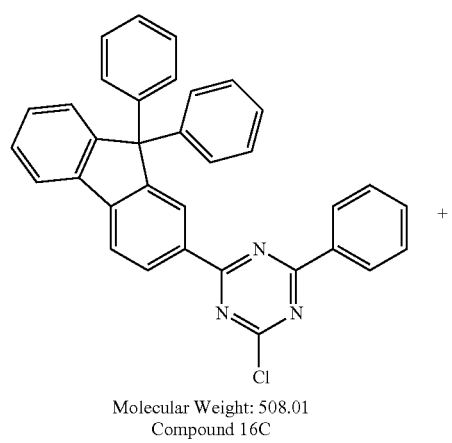

Molecular Weight: 508.01
Compound 16C

+

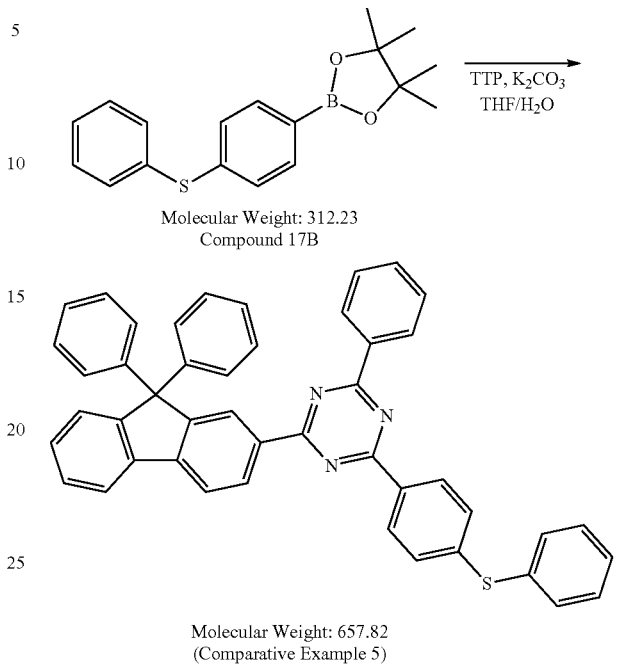

Molecular Weight: 312.23
Compound 17B

Molecular Weight: 657.82
(Comparative Example 5)

(1) Preparation of Compound 17B (4-bromophenyl) (phenyl)sulfine (10.0 g, 37 mmol), bis(pinacolato)diboron (10.5 g, 42 mmol), and potassium acetate (11.1 g, 113 mmol) were mixed under a nitrogen atmosphere, and the resulting mixture was added to 100 ml of dioxane, and heated while being stirred. Bis(dibenzylideneacetone)palladium (0.7 g, 1 mmol) and tricyclohexylphosphine (0.7 g, 2 mmol) were put into the mixture under reflux, and the resulting mixture was heated and stirred for 12 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 17B (6.5 g, 55%).

(2) Preparation of Comparative Example 5

Compound 16C (12.5 g, 25 mmol) and Compound 17B (8.5 g, 27 mmol) were put into 150 ml of tetrahydrofuran under a nitrogen atmosphere, and the resulting mixture was stirred and refluxed. Thereafter, potassium carbonate (10.2 g, 74 mmol) was dissolved in 50 ml of water, the resulting solution was introduced thereinto, the resulting mixture was sufficiently stirred, and then tetrakistriphenyl-phosphinopalladium (0.9 g, 0.7 mmol) was introduced thereinto. After the reaction for 11 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Comparative Example 5 (11.2 g, 71%).

<Synthesis Example 25>—Preparation of Compound Represented by Comparative Example 6

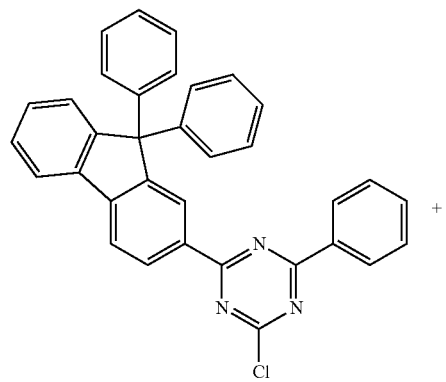

Molecular Weight: 508.01
Compound 16C

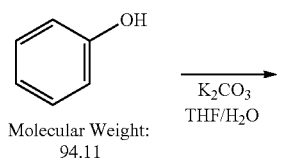

Molecular Weight: 94.11

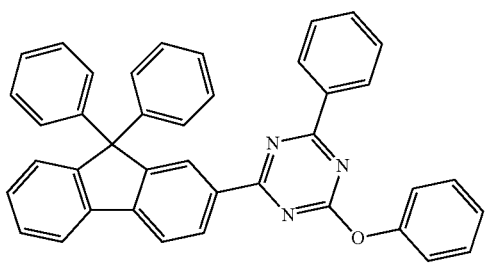

Molecular Weight: 565.66
Comparative Example 6

Compound 16C (15 g, 30 mmol) and bromophenol (4.2 g, 44 mmol) were put into 150 ml of tetrahydrofuran under a nitrogen atmosphere, and the resulting mixture was stirred and refluxed. Thereafter, potassium carbonate (12.2 g, 59 mmol) was dissolved in 60 ml of water, and then the resulting solution was introduced thereinto, the resulting mixture was sufficiently stirred, and after the reaction for 11 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Comparative Example 6 (12.8 g, 77%).

<Synthesis Example 26>—Preparation of Compound Represented by Comparative Example 7

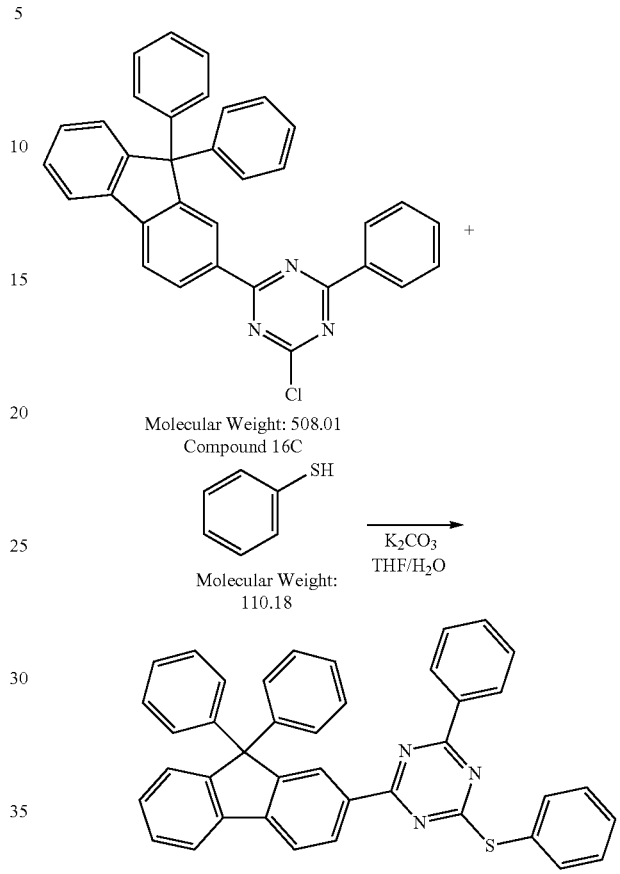

Compound 16C (15 g, 30 mmol) and thiol (4.9 g, 44 mmol) were put into 150 ml of tetrahydrofuran under a nitrogen atmosphere, and the resulting mixture was stirred and refluxed. Thereafter, potassium carbonate (12.2 g, 59 mmol) was dissolved in 60 ml of water, and then the resulting solution was introduced thereinto, and after the reaction for 11 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Comparative Example 7 (10.3 g, 60%).

EXAMPLES

Example 1

A glass substrate (Corning 7059 glass) thinly coated with ITO (indium tin oxide) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode, which was thus prepared, thereby forming a hole injection layer. HT1 (400 Å), which is a material transporting holes, was vacuum deposited thereon, and then compounds of a host H1 and a dopant D1 were vacuum deposited as a light emitting layer to have a thickness of 300 Å. Compound 1 prepared in Preparation Example 1 and LiQ (lithium quinolate) were vacuum deposited at a weight ratio of 1:1 on the light emitting layer, thereby forming an electron injection and transport layer having a thickness of 350 Å. Lithium fluoride (LiF) and aluminum were sequentially deposited to have a thickness of 12 Å and 2,000 Å, respectively, on the electron injection and transport layer, thereby forming a negative electrode. An organic light emitting device was manufactured.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

The structure of each of hexanitrile hexaazatriphenylene, LiQ, HT1, and D1 is as follows.

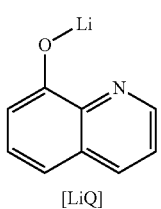

[Hexanitrile hexaazatriphenylene]   [LiQ]

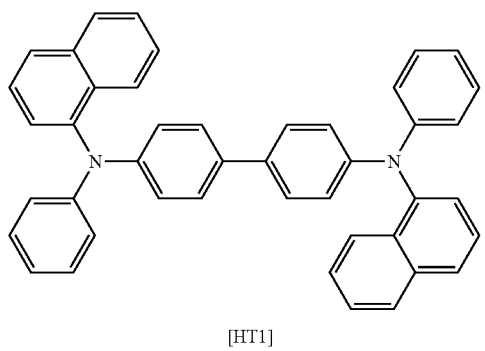

[HT1]

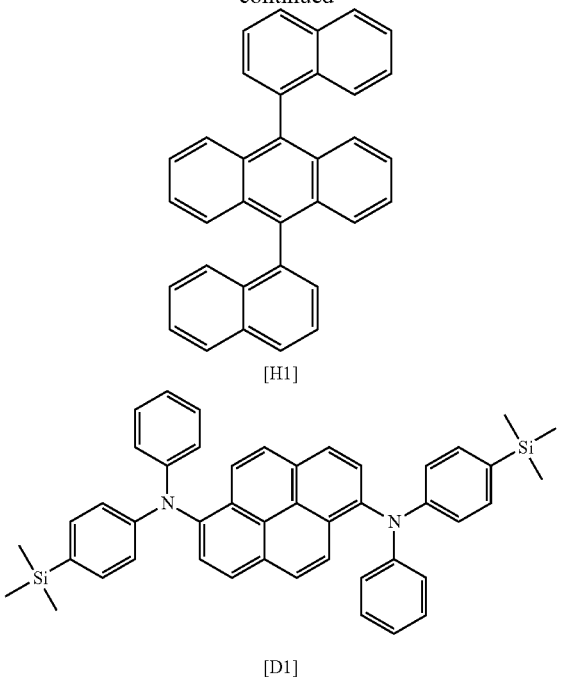

[H1]

[D1]

Example 2

An experiment was performed in the same manner as in Example 1, except that as the electron transport layer, Compound 2 was used instead of Compound 1.

Example 3

An experiment was performed in the same manner as in Example 1, except that as the electron transport layer, Compound 3 was used instead of Compound 1.

Example 4

An experiment was performed in the same manner as in Example 1, except that as the electron transport layer, Compound 4 was used instead of Compound 1.

Example 5

An experiment was performed in the same manner as in Example 1, except that as the electron transport layer, Compound 5 was used instead of Compound 1.

Example 6

An experiment was performed in the same manner as in Example 1, except that as the electron transport layer, Compound 6 was used instead of Compound 1.

Example 7

An experiment was performed in the same manner as in Example 1, except that as the electron transport layer, Compound 7 was used instead of Compound 1.

Example 8

An experiment was performed in the same manner as in Example 1, except that as the electron transport layer, Compound 8 was used instead of Compound 1.

Example 9

An experiment was performed in the same manner as in Example 1, except that as the electron transport layer, Compound 9 was used instead of Compound 1.

Example 10

An experiment was performed in the same manner as in Example 1, except that as the electron transport layer, Compound 10 was used instead of Compound 1.

Example 11

An experiment was performed in the same manner as in Example 1, except that as the electron transport layer, Compound 11 was used instead of Compound 1.

Example 12

An experiment was performed in the same manner as in Example 1, except that as the electron transport layer, Compound 12 was used instead of Compound 1.

Example 13

An experiment was performed in the same manner as in Example 1, except that as the electron transport layer, Compound 13 was used instead of Compound 1.

Example 14

An experiment was performed in the same manner as in Example 1, except that as the electron transport layer, Compound 14 was used instead of Compound 1.

Example 15

An experiment was performed in the same manner as in Example 1, except that as the electron transport layer, Compound 15 was used instead of Compound 1.

Example 16

An experiment was performed in the same manner as in Example 1, except that as the electron transport layer, Compound 16 was used instead of Compound 1.

Example 17

An experiment was performed in the same manner as in Example 1, except that as the electron transport layer, Compound 17 was used instead of Compound 1.

Example 18

An experiment was performed in the same manner as in Example 1, except that as the electron transport layer, Compound 18 was used instead of Compound 1.

Example 19

An experiment was performed in the same manner as in Example 1, except that as the electron transport layer, Compound 19 was used instead of Compound 1.

Comparative Example 1

An organic light emitting device was manufactured in the same manner as in Experimental Example 1, except that the compound in Comparative Example 1 was used instead of Compound 1 in Experimental Example 1.

Comparative Example 2

An organic light emitting device was manufactured in the same manner as in Experimental Example 1, except that the compound in Comparative Example 2 was used instead of Compound 1 in Experimental Example 1.

Comparative Example 3

An organic light emitting device was manufactured in the same manner as in Experimental Example 1, except that the compound in Comparative Example 3 was used instead of Compound 1 in Experimental Example 1.

Comparative Example 4

An organic light emitting device was manufactured in the same manner as in Experimental Example 1, except that the compound in Comparative Example 4 was used instead of Compound 1 in Experimental Example 1.

Comparative Example 5

An organic light emitting device was manufactured in the same manner as in Experimental Example 1, except that the compound in Comparative Example 5 was used instead of Compound 1 in Experimental Example 1.

Comparative Example 6

An organic light emitting device was manufactured in the same manner as in Experimental Example 1, except that the compound in Comparative Example 6 was used instead of Compound 1 in Experimental Example 1.

Comparative Example 7

An organic light emitting device was manufactured in the same manner as in Experimental Example 1, except that the compound in Comparative Example 7 was used instead of Compound 1 in Experimental Example 1.

Comparative Example 8

An organic light emitting device was manufactured in the same manner as in Experimental Example 1, except that a compound of the following ET1 was used instead of Compound 1 in Experimental Example 1.

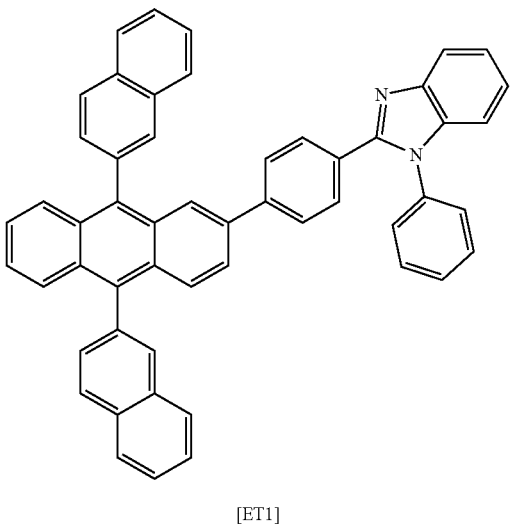 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

[ET1]

For the organic light emitting devices manufactured by using each compound as the electron transport layer material as in Examples 1 to 19 and Comparative Examples 1 to 8, the driving voltage and the light emitting efficiency were measured at a current density of 10 mA/cm², and a time (LT98) for reaching a 98% value compared to the initial luminance was measured at a current density of 20 mA/cm². The results are shown in the following Table 1.

TABLE 1

| Classification | Compound (Electron transport layer) | Voltage (V) | Current efficiency (cd/A) | Color coordinate (x, y) | Life Time 98 at 20 mA/cm² |
|---|---|---|---|---|---|
| Example 1 | Compound 1 | 3.50 | 6.88 | (0.133, 0.135) | 111 |
| Example 2 | Compound 2 | 3.61 | 6.51 | (0.133, 0.137) | 120 |
| Example 3 | Compound 3 | 3.66 | 6.48 | (0.134, 0.133) | 125 |
| Example 4 | Compound 4 | 3.55 | 7.08 | (0.132, 0.133) | 115 |
| Example 5 | Compound 5 | 3.66 | 6.38 | (0.135, 0.128) | 133 |
| Example 6 | Compound 6 | 3.42 | 7.05 | (0.133, 0.135) | 100 |
| Example 7 | Compound 7 | 4.71 | 6.30 | (0.133, 0.133) | 70 |
| Example 8 | Compound 8 | 4.37 | 6.68 | (0.133, 0.133) | 130 |
| Example 9 | Compound 9 | 4.63 | 6.57 | (0.133, 0.133) | 110 |
| Example 10 | Compound 10 | 4.35 | 6.50 | (0.133, 0.133) | 130 |
| Example 11 | Compound 11 | 4.37 | 6.28 | (0.133, 0.133) | 140 |
| Example 12 | Compound 12 | 4.35 | 6.10 | (0.133, 0.133) | 220 |
| Example 13 | Compound 13 | 3.60 | 7.46 | (0.133, 0.133) | 110 |
| Example 14 | Compound 14 | 4.10 | 7.16 | (0.133, 0.133) | 150 |
| Example 15 | Compound 15 | 4.07 | 6.96 | (0.133, 0.133) | 130 |
| Example 16 | Compound 16 | 3.97 | 7.05 | (0.133, 0.133) | 170 |
| Example 17 | Compound 17 | 4.88 | 5.27 | (0.133, 0.133) | 260 |
| Example 18 | Compound 18 | 4.32 | 7.1 | (0.133, 0.133) | 155 |
| Example 19 | Compound 19 | 4.34 | 5.86 | (0.133, 0.133) | 190 |
| Comparative Example 1 | Comparative Example 1 | 4.01 | 4.99 | (0.134, 0.133) | 85 |
| Comparative Example 2 | Comparative Example 2 | 3.60 | 7.08 | (0.137, 0.126) | 12 |
| Comparative Example 3 | Comparative Example 3 | 3.61 | 7.00 | (0.137, 0.128) | 5 |
| Comparative Example 4 | Comparative Example 4 | 4.12 | 5.11 | (0.135, 0.129) | 3 |
| Comparative Example 5 | Comparative Example 5 | 4.18 | 5.03 | (0.138, 0.131) | 2 |
| Comparative Example 6 | Comparative Example 6 | 4.99 | 1.21 | (0.135, 0.133) | 7 |
| Comparative Example 7 | Comparative Example 7 | 5.08 | 2.88 | (0.138, 0.134) | 10 |
| Comparative Example 8 | ET1 | 3.98 | 5.77 | (0.136, 0.126) | 80 |

As can be seen from Table 1, it can be seen that when an organic light emitting device manufactured by using the compound of the present specification as an electron transport layer material is compared with the Comparative Examples, excellent characteristics are exhibited in terms of efficiency and stability.

The invention claimed is:

1. A compound represented by the following Chemical Formula 1:

[Chemical Formula 1]

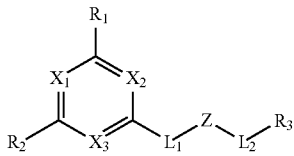

in Chemical Formula 1,
at least one of $X_1$ to $X_3$ is N, and the others are the same as or different from each other, and are each independently N or CR,
R is hydrogen; deuterium; a halogen group; a cyano group; a nitro group; a substituted or unsubstituted aryl group, or a substituted or unsubstituted heteroaryl group comprising one or more of N, O, and S atoms,
Z is O, S, Se, or Te,
$L_1$ is an unsubstituted arylene group; or a substituted or unsubstituted heteroarylene group comprising one or more of N, O, and S atoms,
$L_2$ is a substituted or unsubstituted arylene group; or a substituted or unsubstituted heteroarylene group comprising one or more of N, O, and S atoms,
$R_1$ and $R_2$ are the same as or different from each other, and are each independently a phenyl group unsubstituted or substituted with a halogen group, a cyano group, a nitro group, an alkyl group, an alkenyl group, an alkoxy group, a cycloalkyl group, an aryl group, or a heteroaryl group comprising one or more of N, O, or S atoms; a substituted or unsubstituted biphenyl group; a substituted or unsubstituted terphenyl group; a substituted or unsubstituted naphthyl group; a substituted or unsubstituted anthracenyl group; or a substituted or unsubstituted fluorenyl group, and
$R_3$ is a cyano group; a substituted or unsubstituted silyl group; a substituted or unsubstituted boron group; an unsubstituted alkyl group; an unsubstituted cycloalkyl group; a substituted or unsubstituted alkylaryl group; a substituted or unsubstituted arylphosphine group; a substituted or unsubstituted phosphine oxide group; a substituted amine group, wherein the substitution of the amine group is not an aryl group; a substituted or unsubstituted alkylamine group; a substituted or unsubstituted pyridyl group; a substituted or unsubstituted pyrimidyl group; a substituted or unsubstituted triazinyl group; a substituted or unsubstituted quinolinyl group; a substituted or unsubstituted quinazolyl group; a substituted or unsubstituted thiophene group; a substituted or unsubstituted furan group; a substituted or unsubstituted benzocarbazole group; a substituted or unsubstituted benzothiophene group; a substituted or unsubstituted benzofuran group; a substituted or unsubstituted dibenzocarbazole group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthryl group; a substituted or unsubstituted triphenyl group; a substituted or unsubstituted pyrenyl group; a substituted or unsubstituted chrysenyl group, or

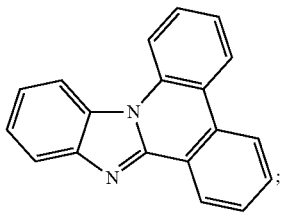

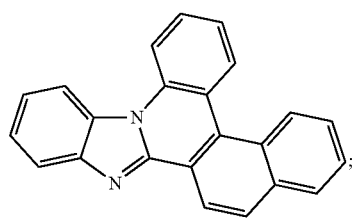

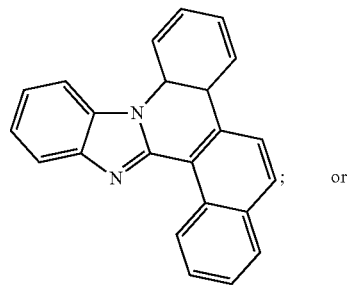
; or

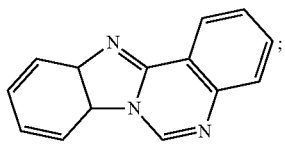
;

wherein the substitution in $R_3$ does not make a fused structure, and provided that when $R_3$ is a pyrimidyl group substituted with a phenyl group, the phenyl group is unsubstituted.

2. The compound of claim 1, wherein $L_1$ is an unsubstituted phenylene group, an unsubstituted biphenylene group, an unsubstituted terphenyl group, an unsubstituted naphthylene group, an unsubstituted anthracenyl group, or an unsubstituted fluorenylene group.

3. The compound of claim 1, wherein $L_2$ is a substituted or unsubstituted phenylene group, a substituted or unsubstituted biphenylene group, a substituted or unsubstituted terphenyl group, a substituted or unsubstituted naphthylene group, a substituted or unsubstituted anthracenyl group, or a substituted or unsubstituted fluorenylene group.

4. The compound of claim 1, wherein $R_3$ is a substituted or unsubstituted pyridyl group, a substituted or unsubstituted pyrimidyl group, a substituted or unsubstituted triazinyl group, a substituted or unsubstituted quinolinyl group, or a substituted or unsubstituted quinazolyl group.

5. The compound of claim 1, wherein $R_3$ is a substituted or unsubstituted thiophene group, a substituted or unsubstituted furan group, a substituted or unsubstituted benzocarbazole group, a substituted or unsubstituted benzothiophene group, a substituted or unsubstituted benzofuran group, or a substituted or unsubstituted dibenzocarbazole group.

6. The compound of claim 1, wherein $R_3$ is a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted triphenyl group, a substituted or unsubstituted pyrenyl group, or a substituted or unsubstituted chrysenyl group.

7. The compound of claim 1, wherein the compound represented by Chemical Formula 1 is any one selected from the following structural formulae:

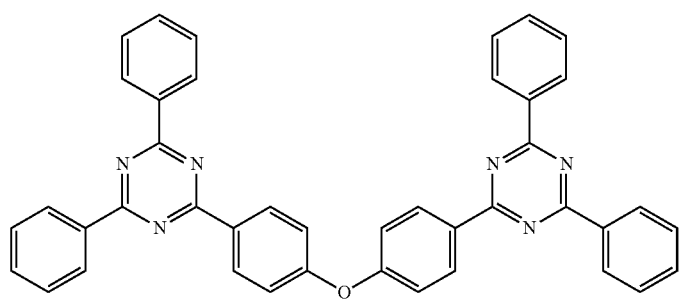

-continued
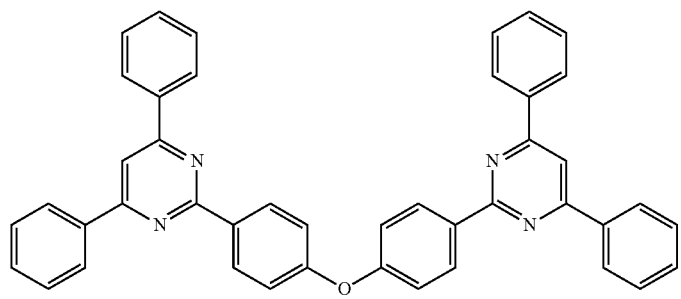
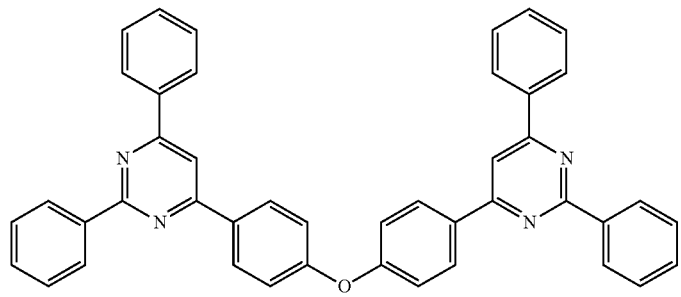
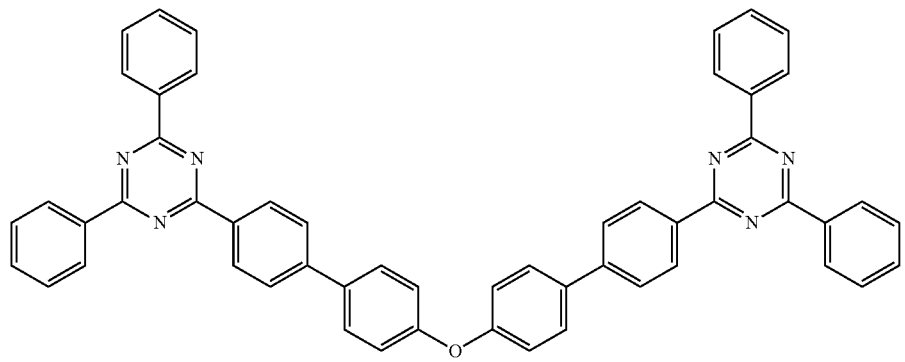
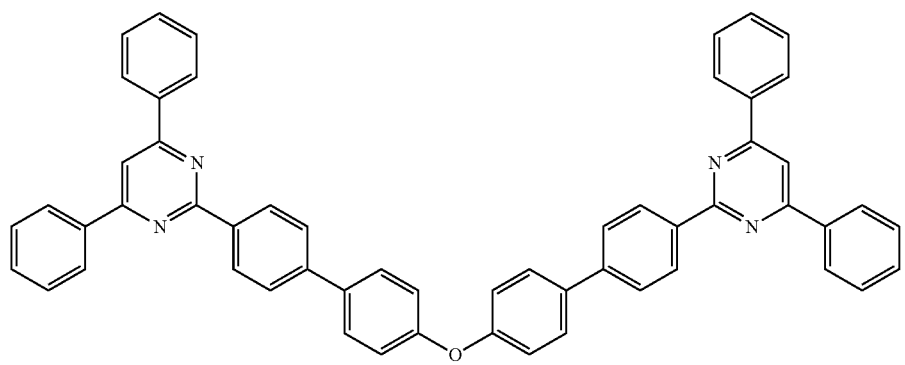
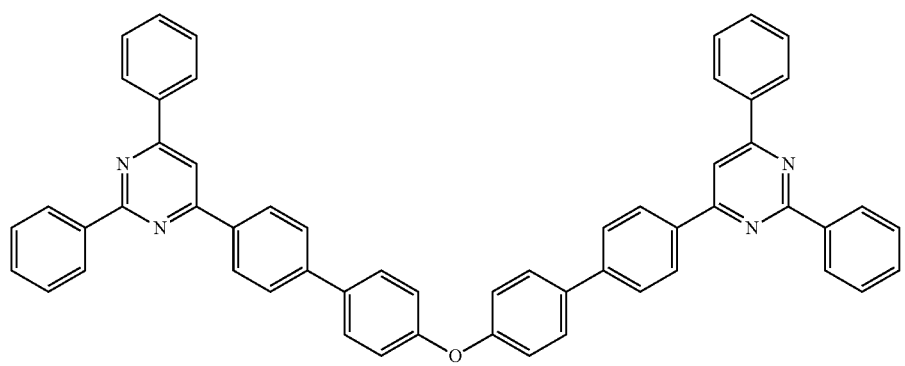

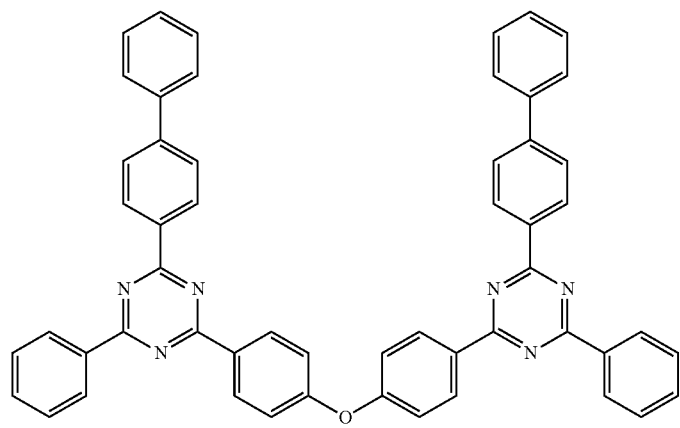
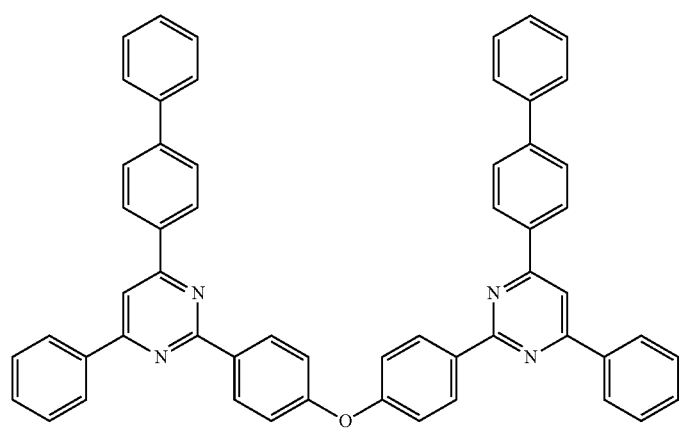
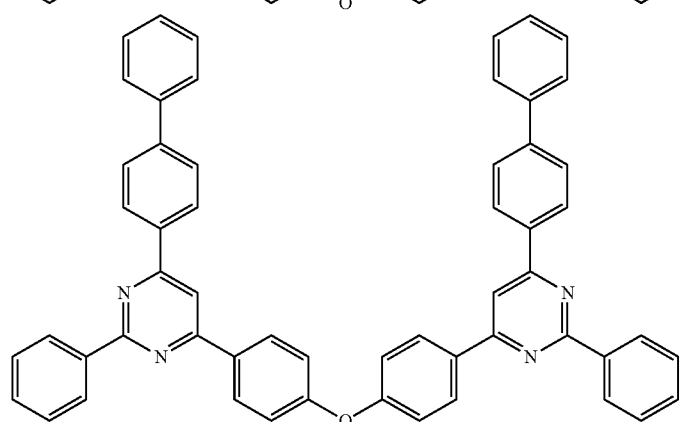
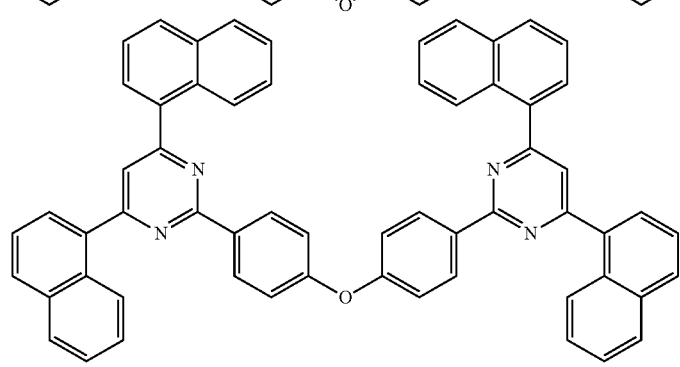

-continued
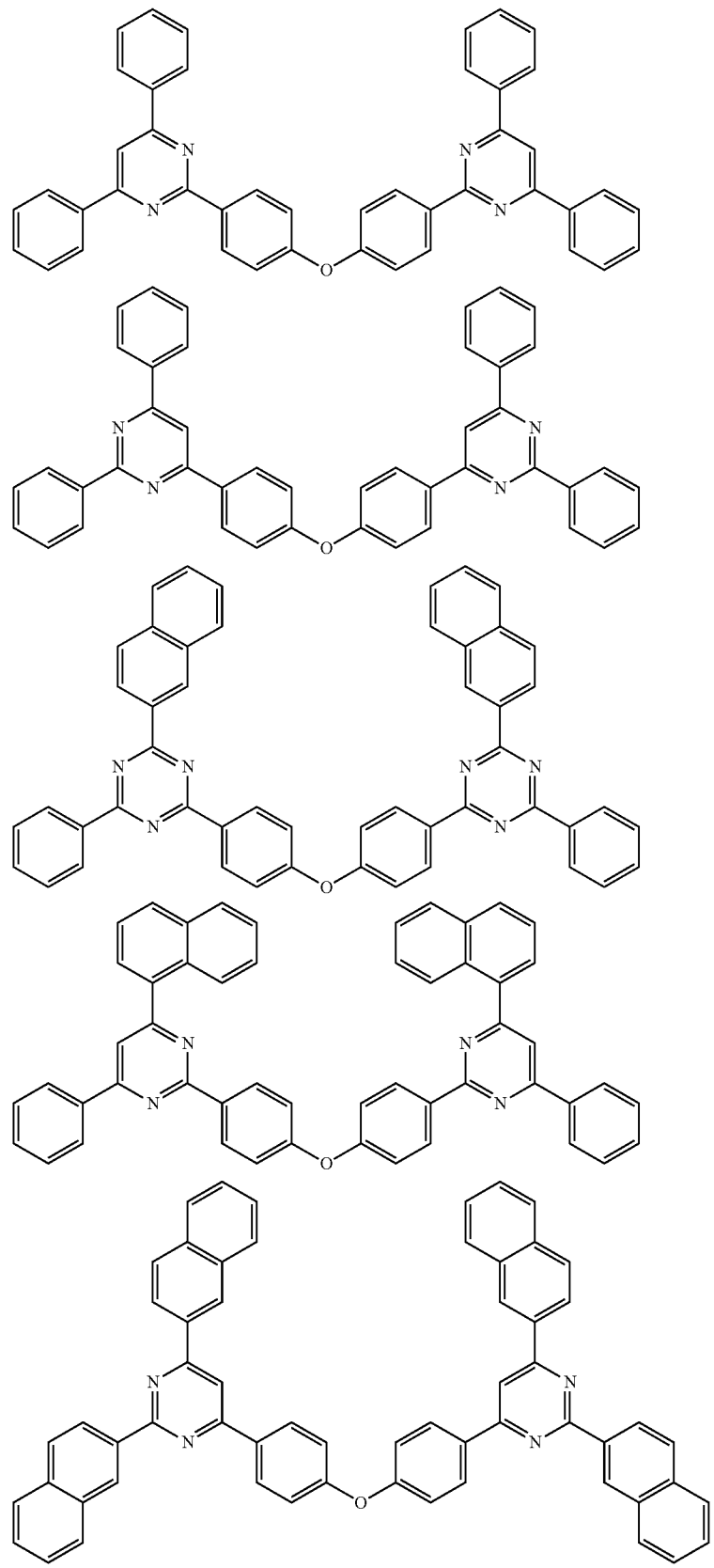

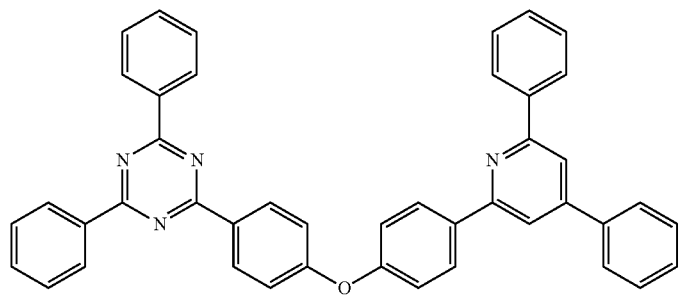
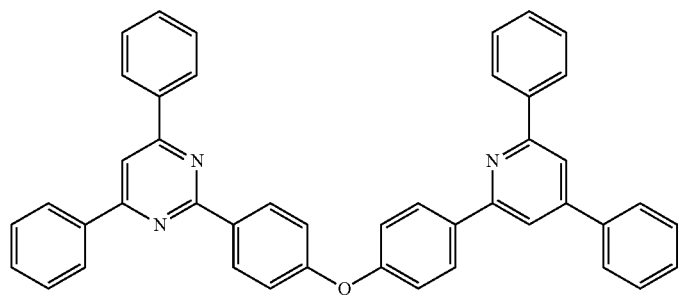
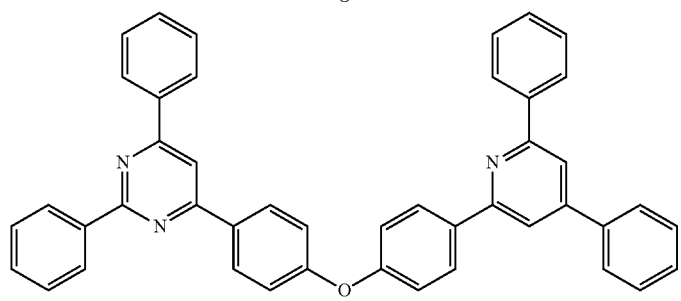
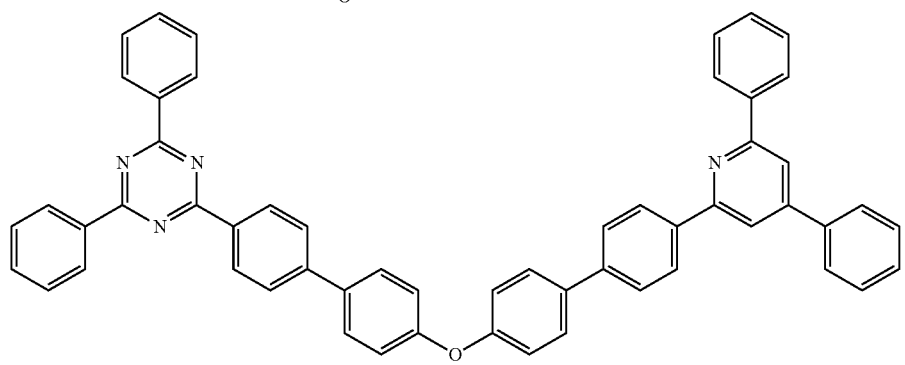
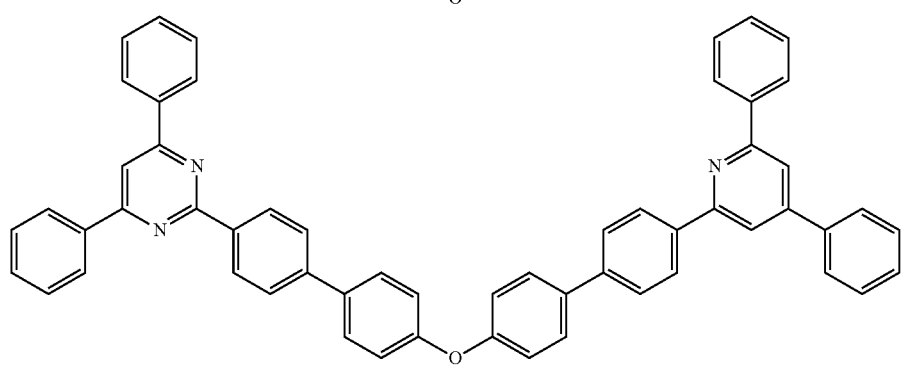

-continued
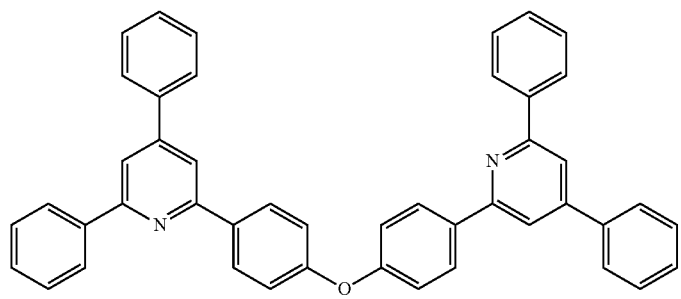
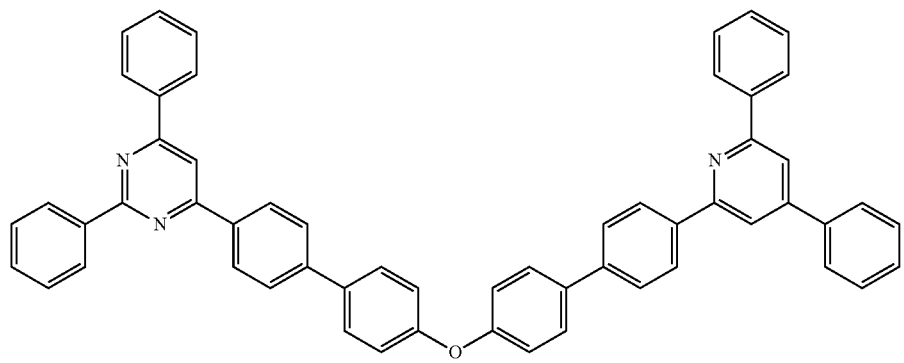
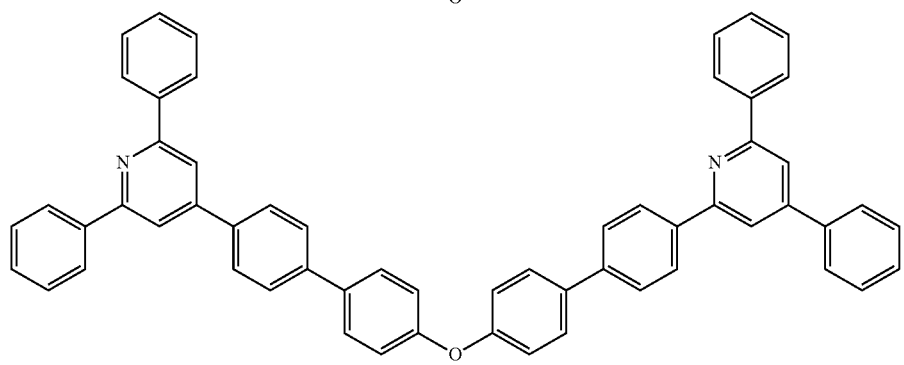
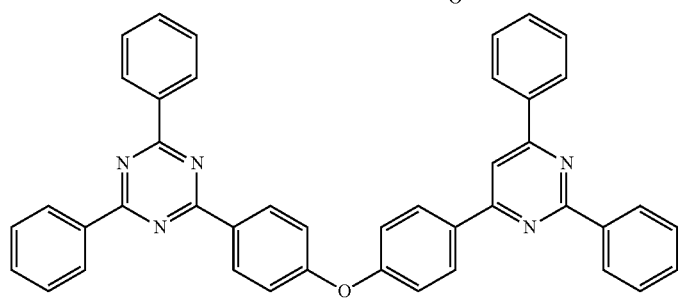
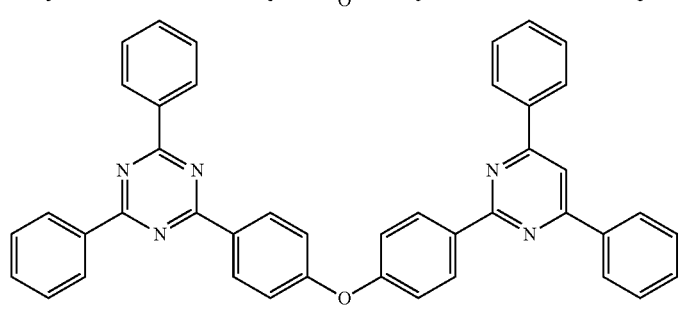

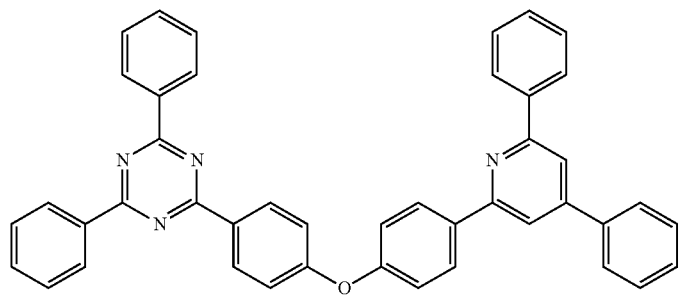
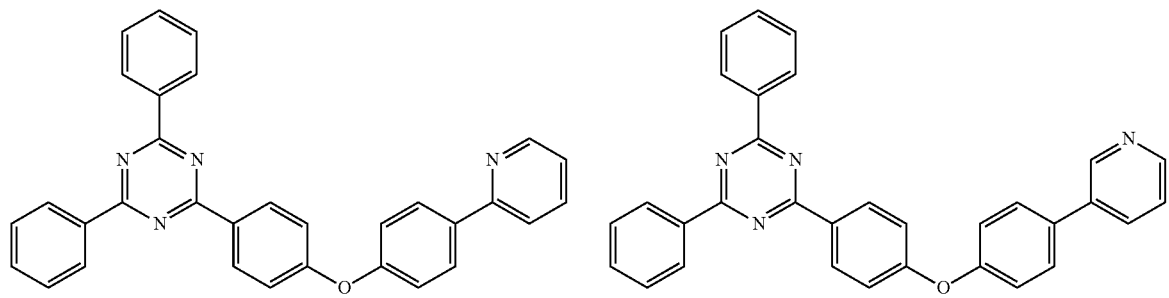
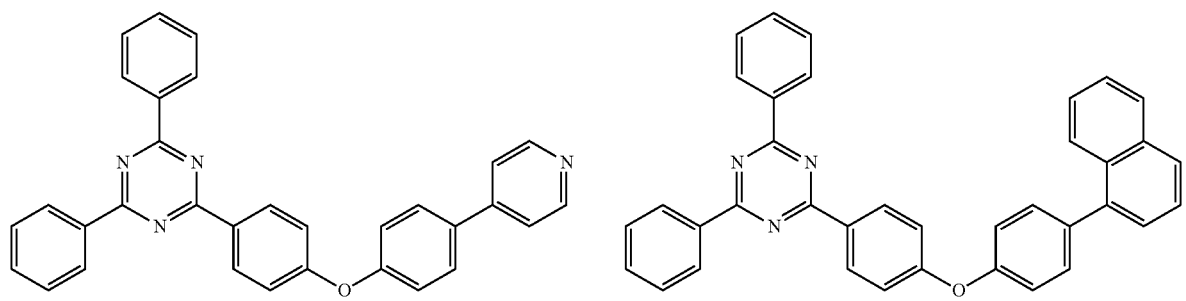
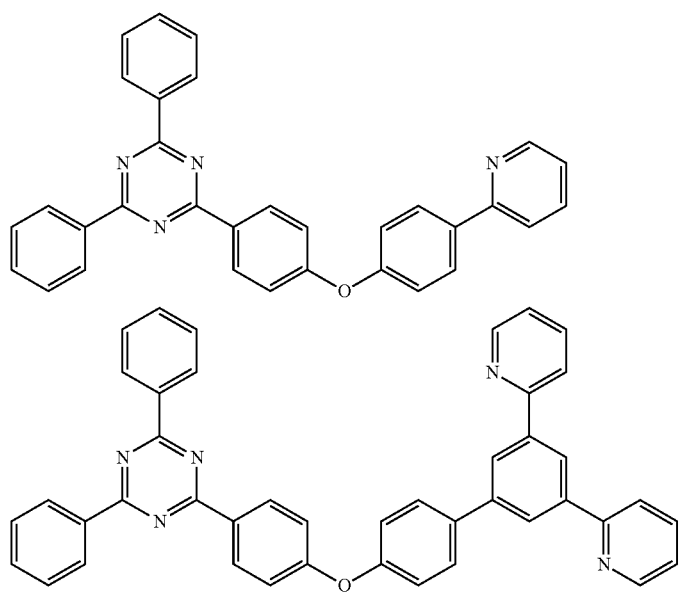

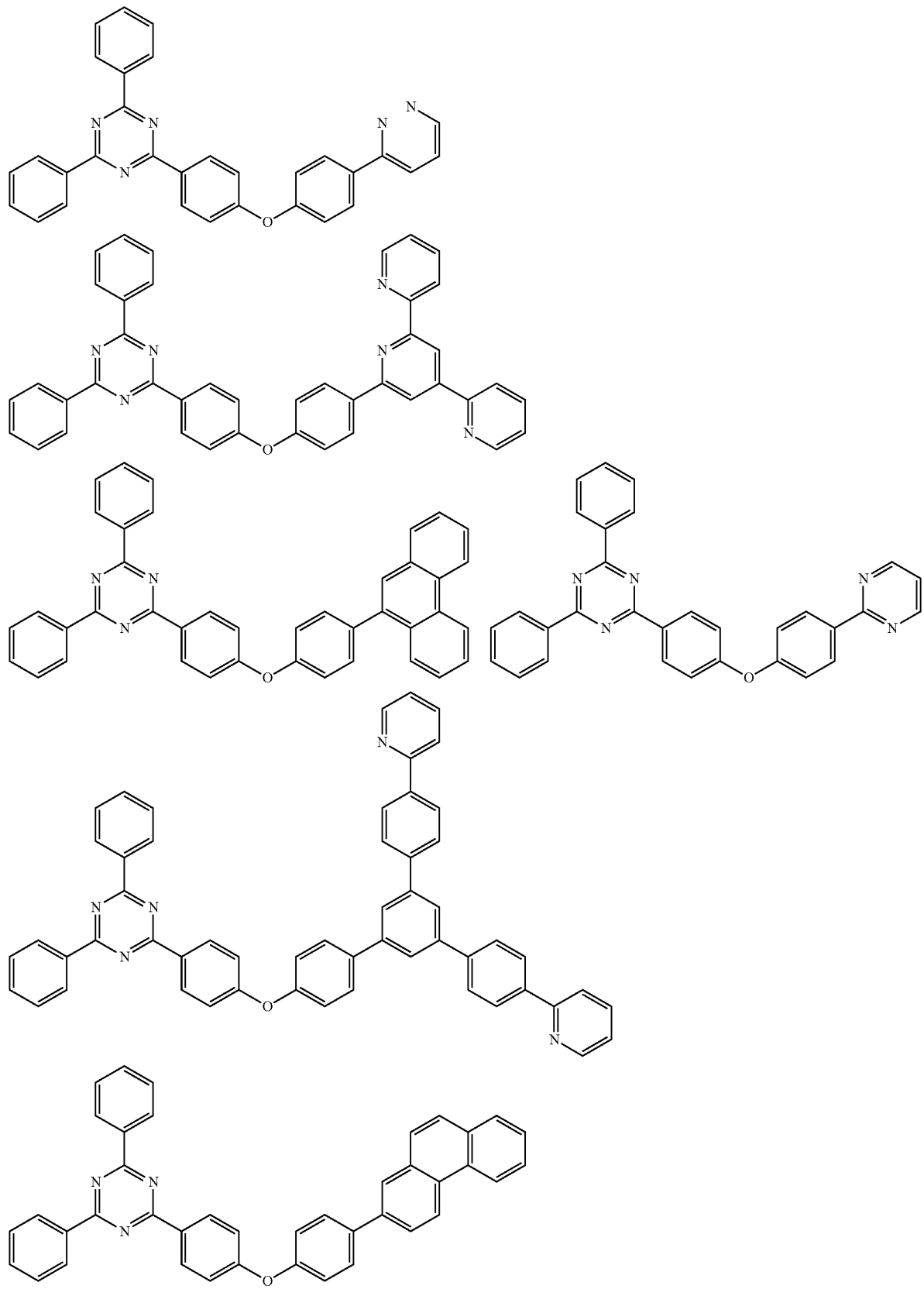

-continued
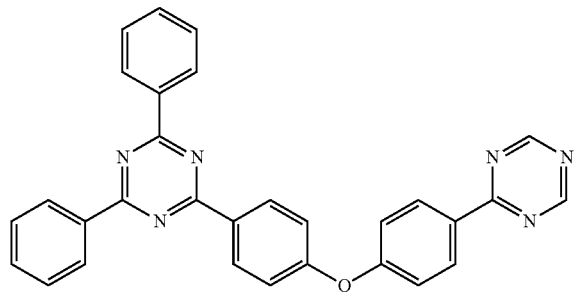
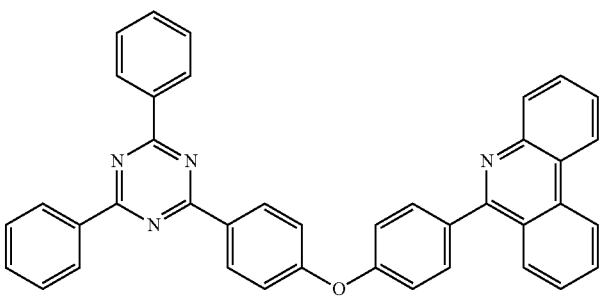
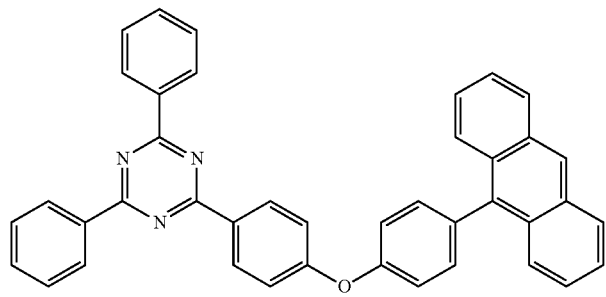
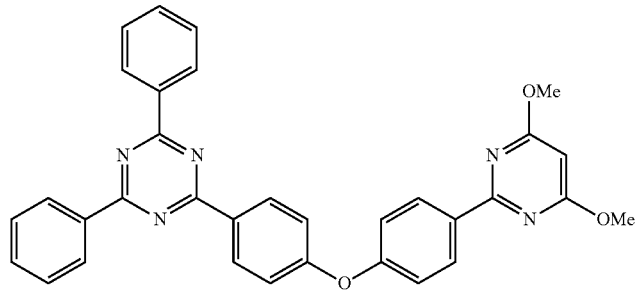
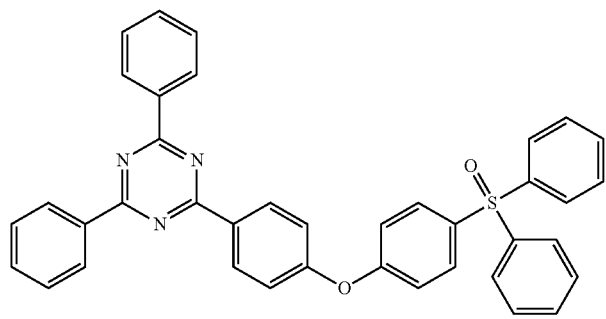
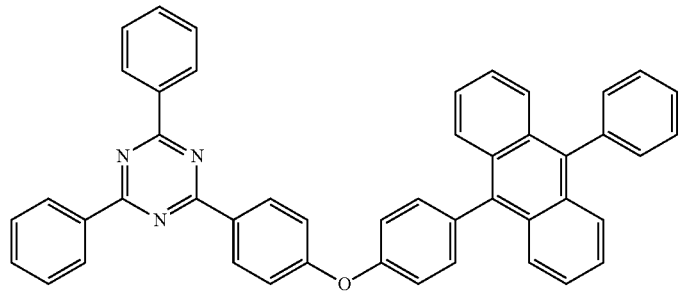

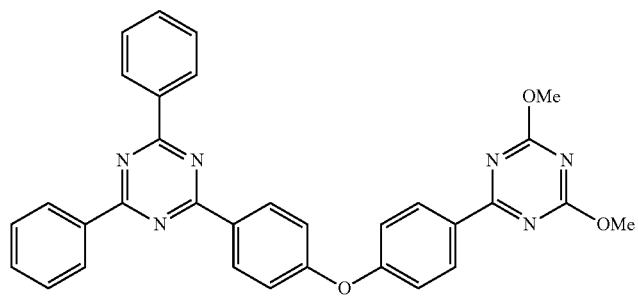
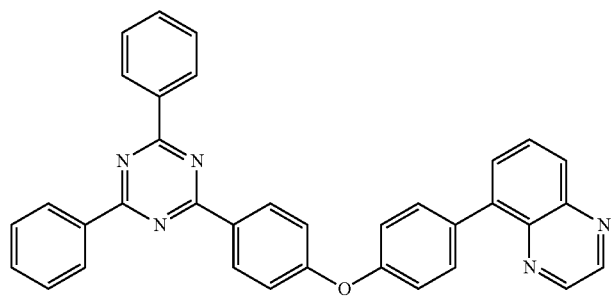
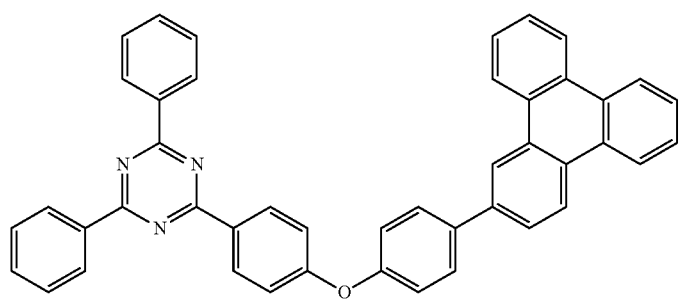
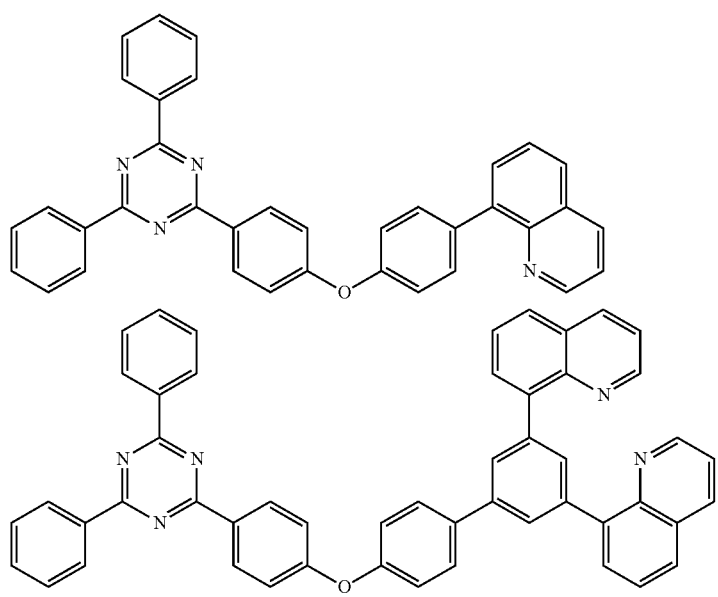

-continued
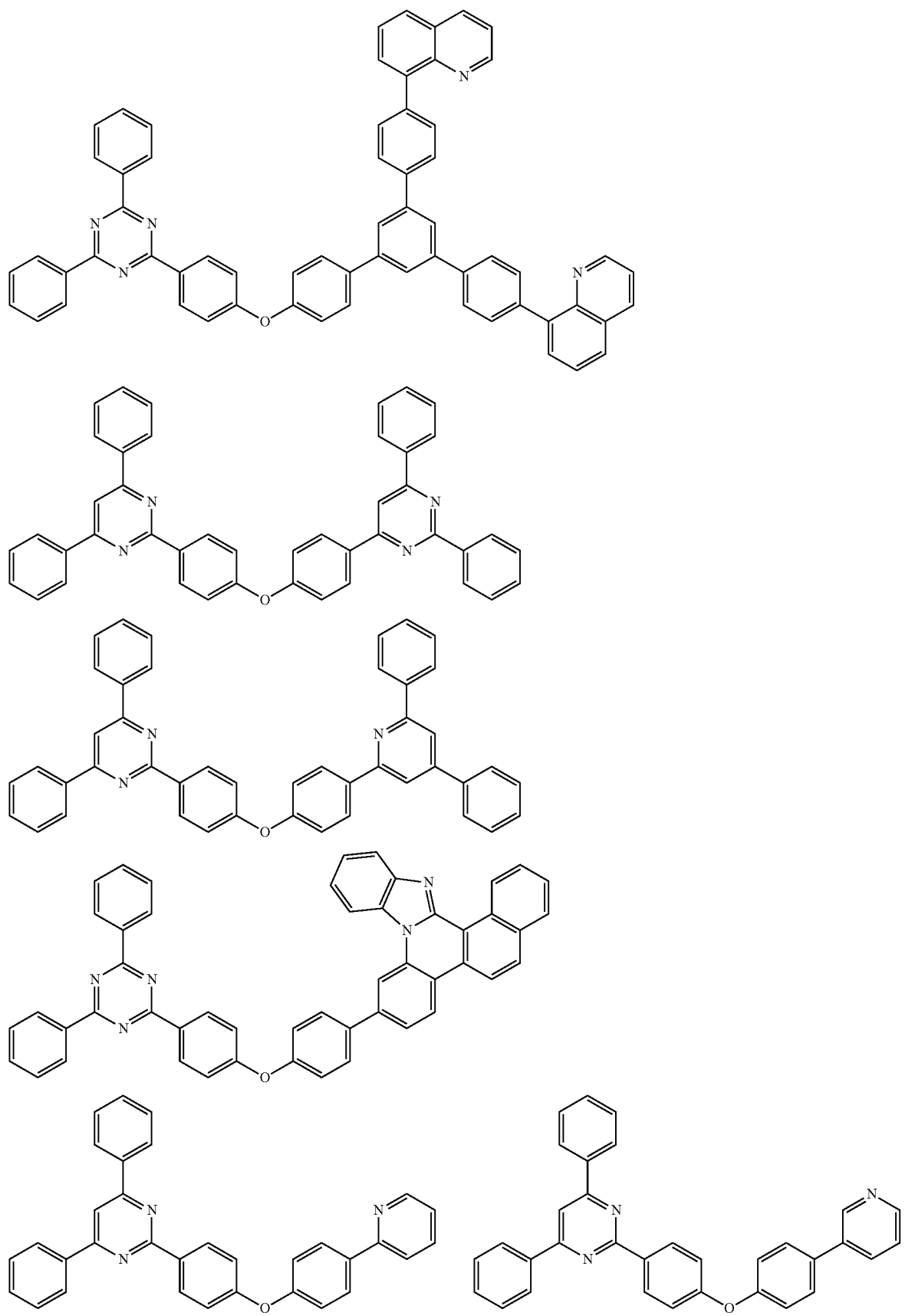

-continued
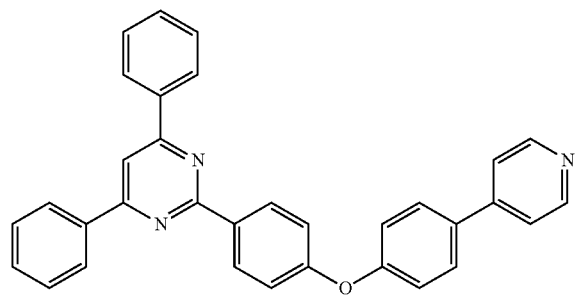
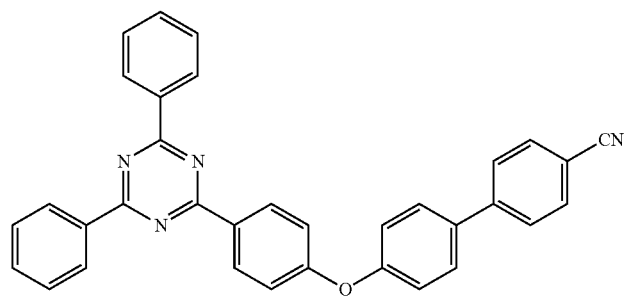
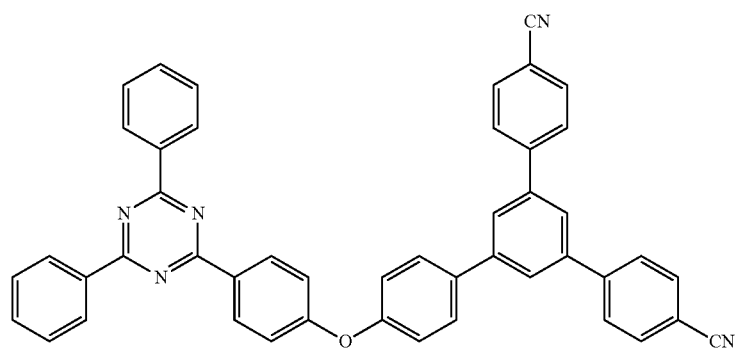
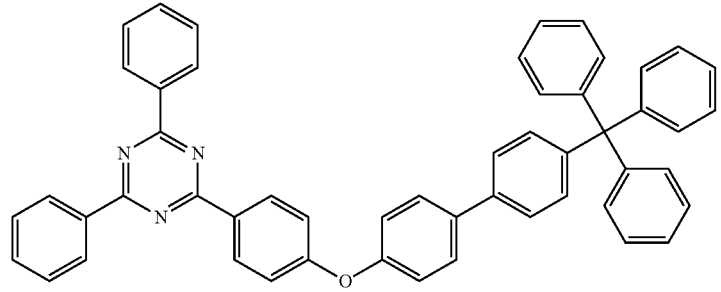
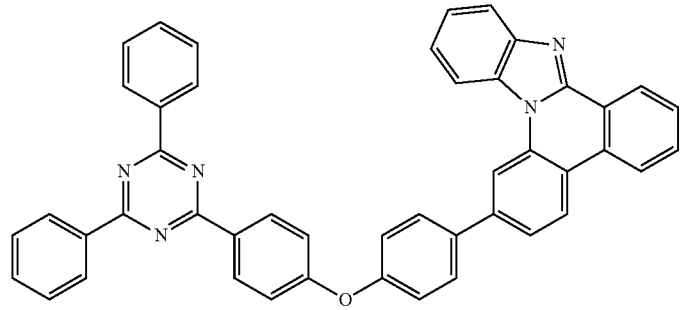

-continued
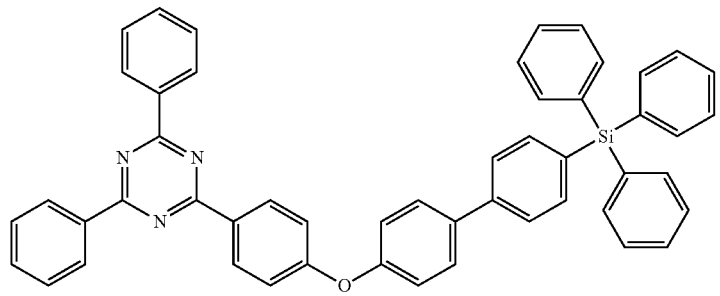
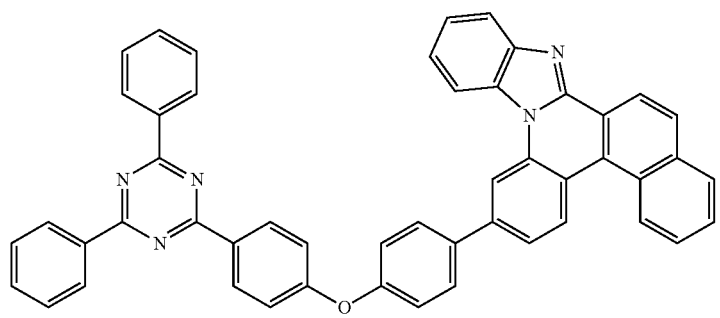
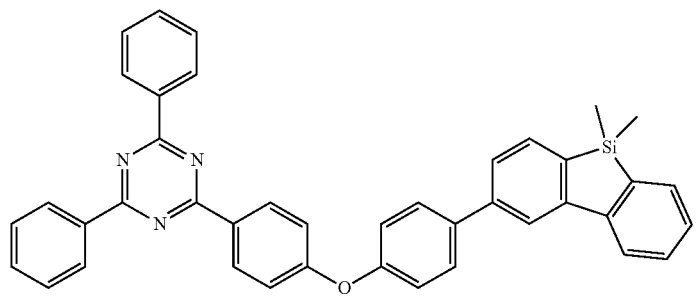
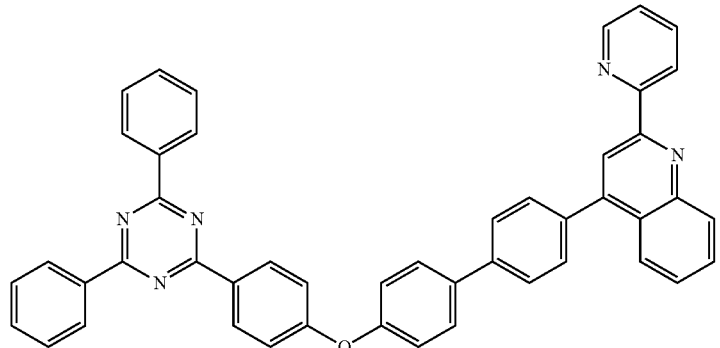
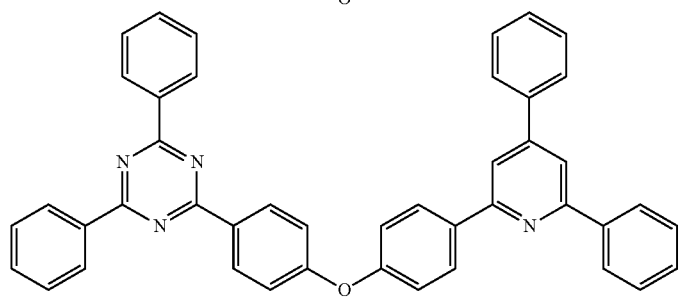

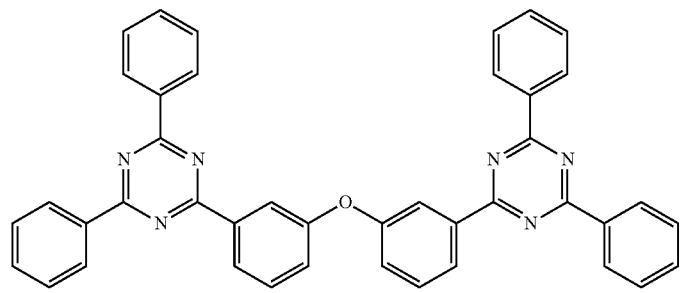
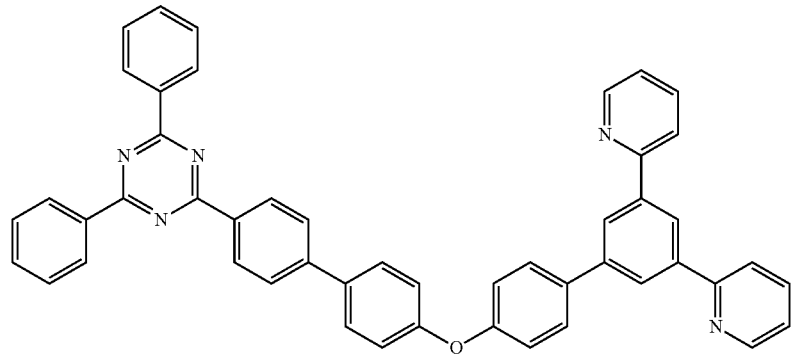
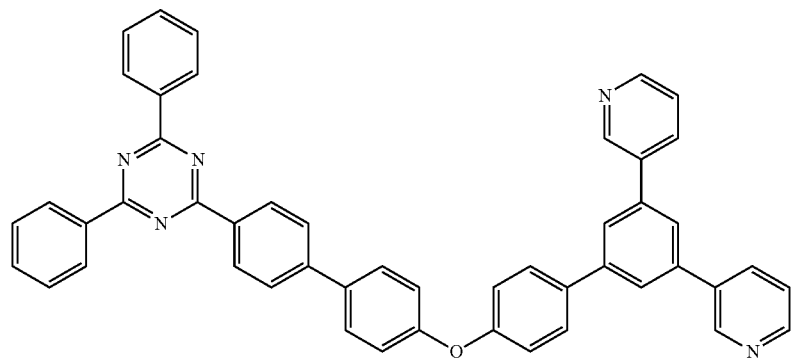
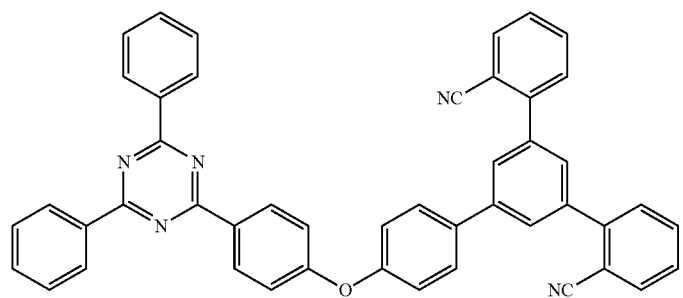
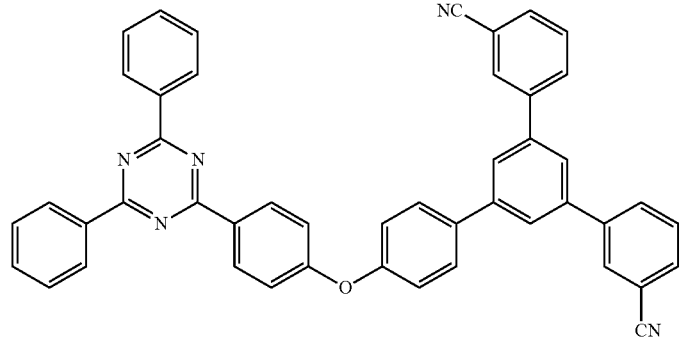

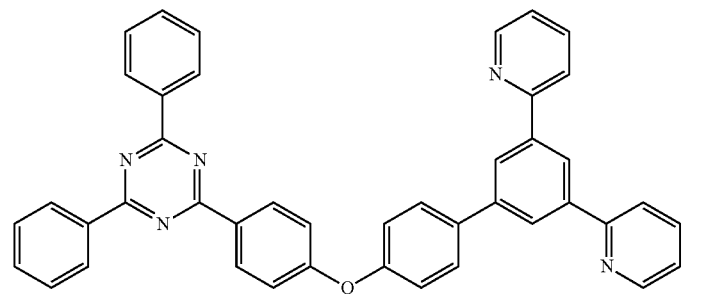
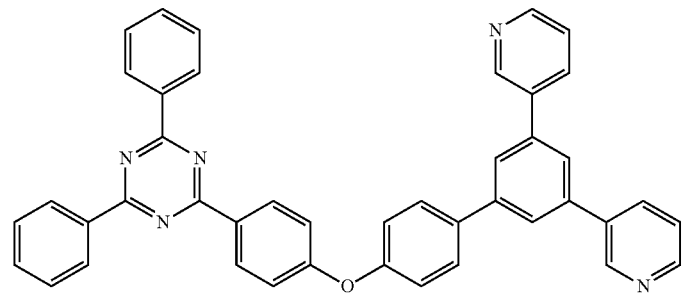
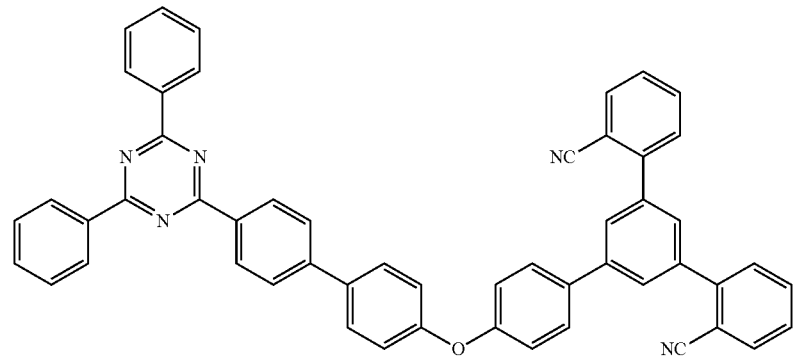
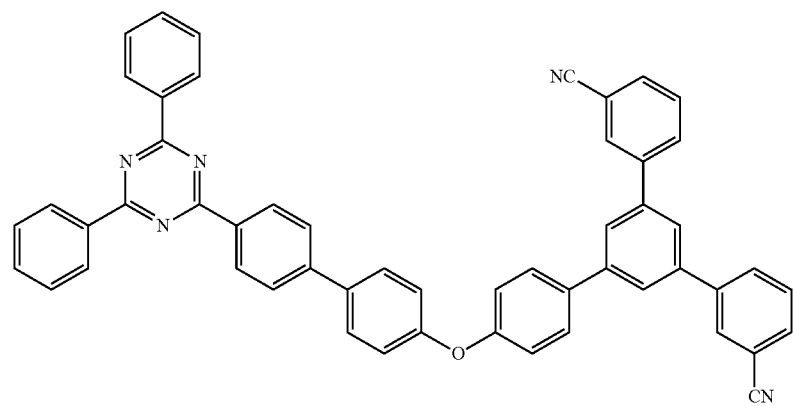
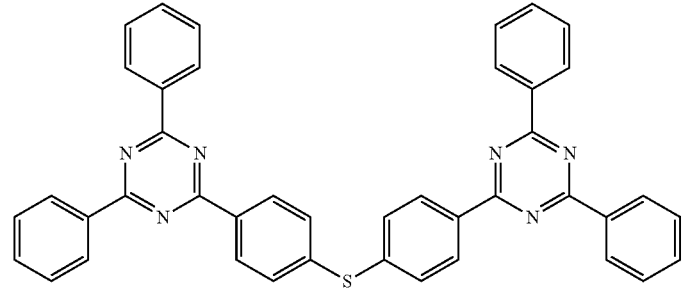

-continued
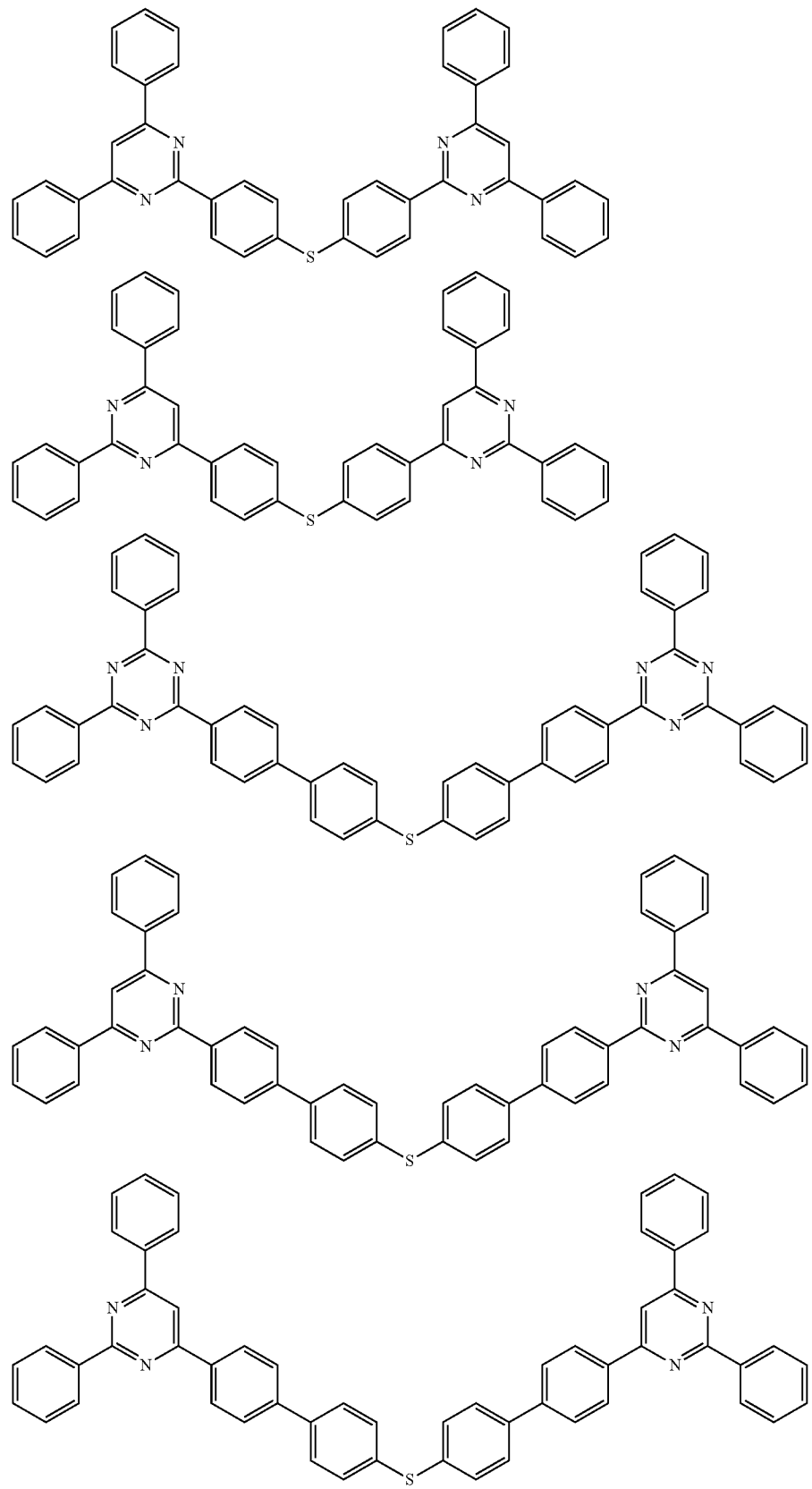

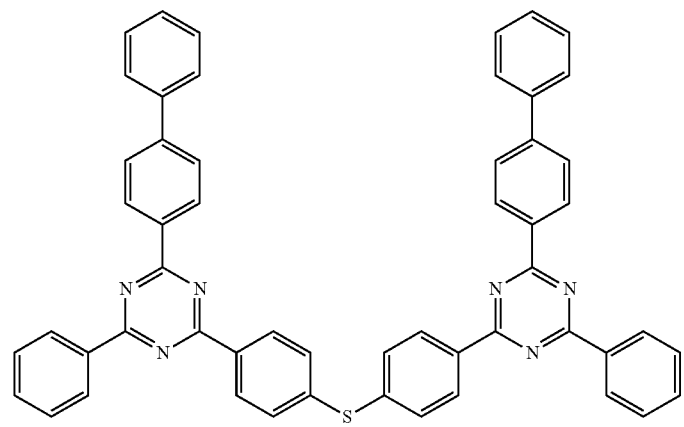
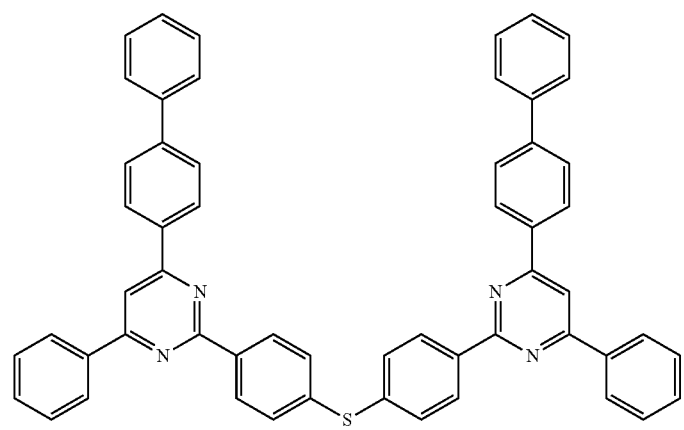
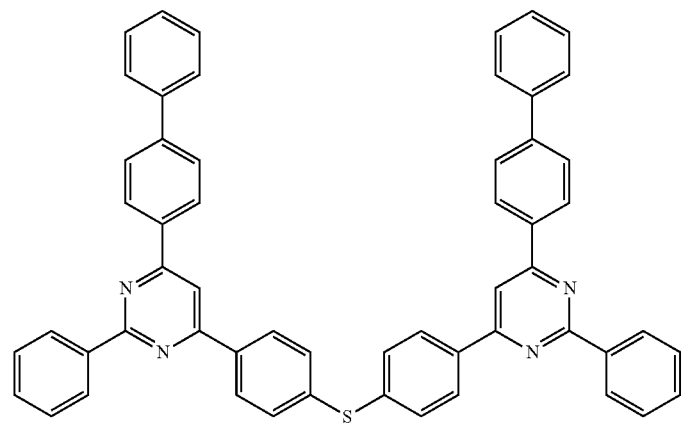
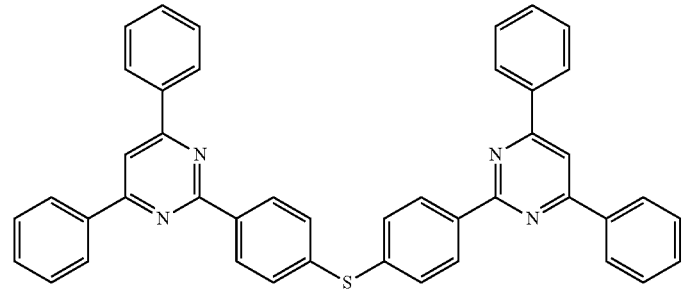

-continued
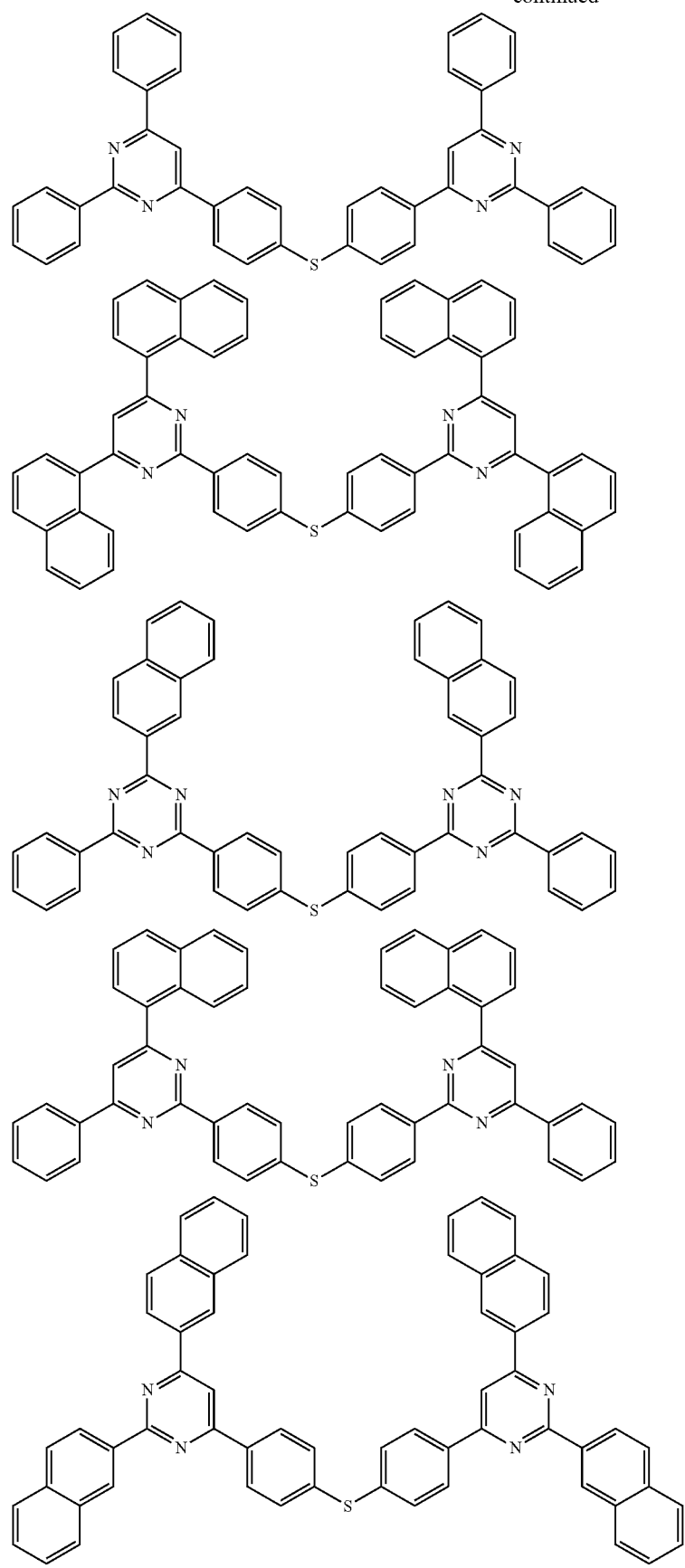

-continued
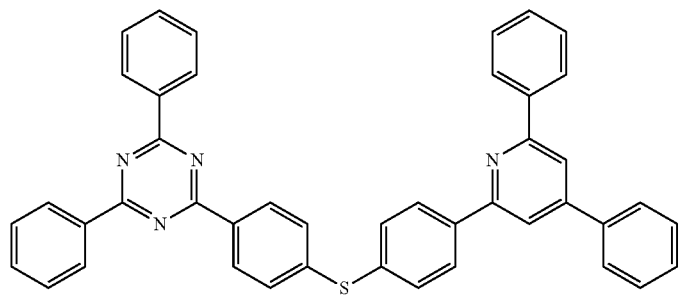
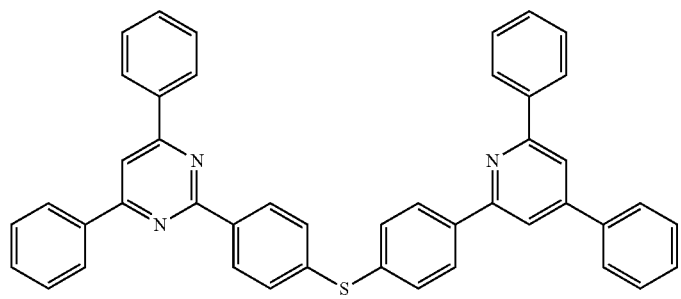
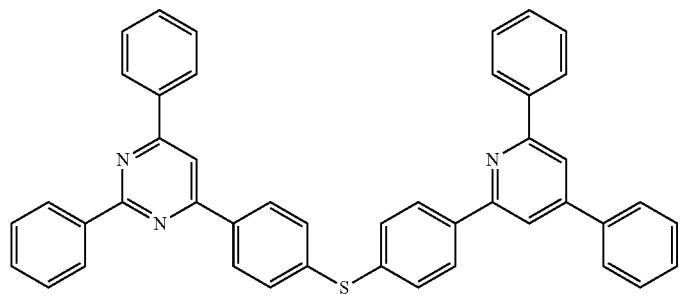
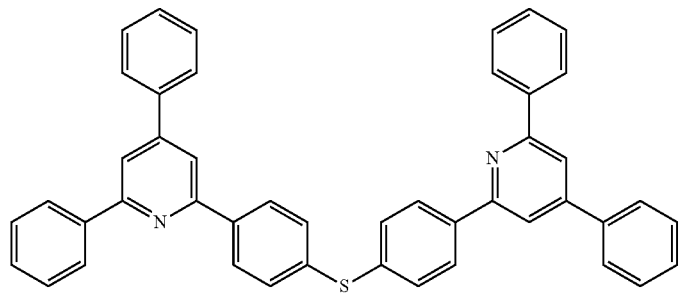
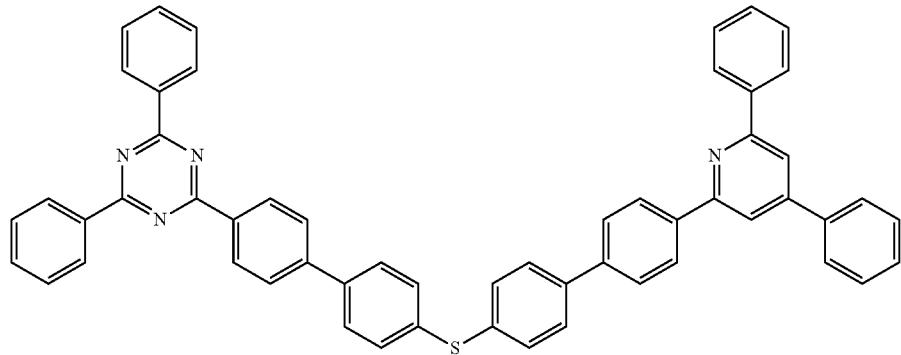

-continued
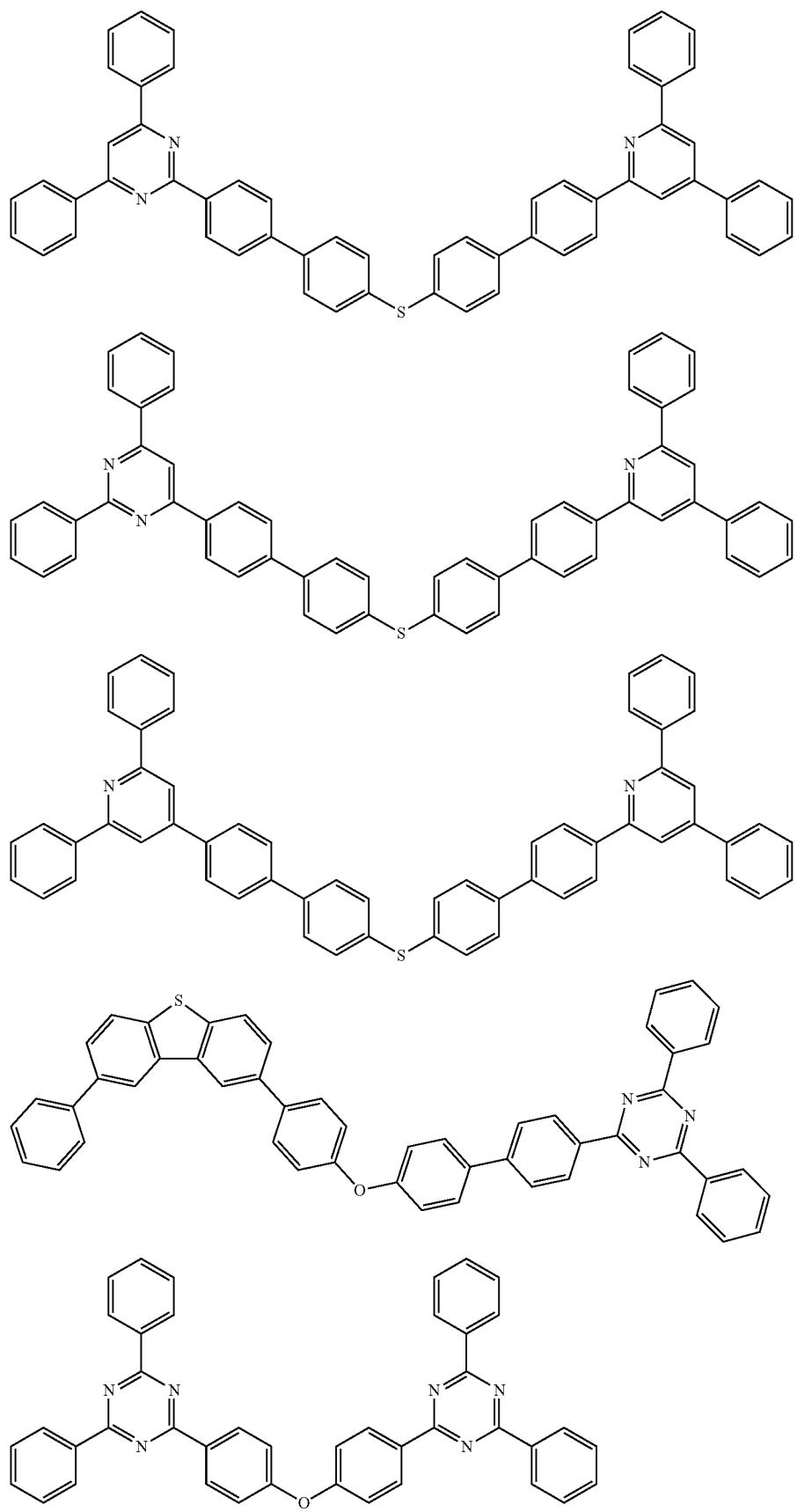

-continued

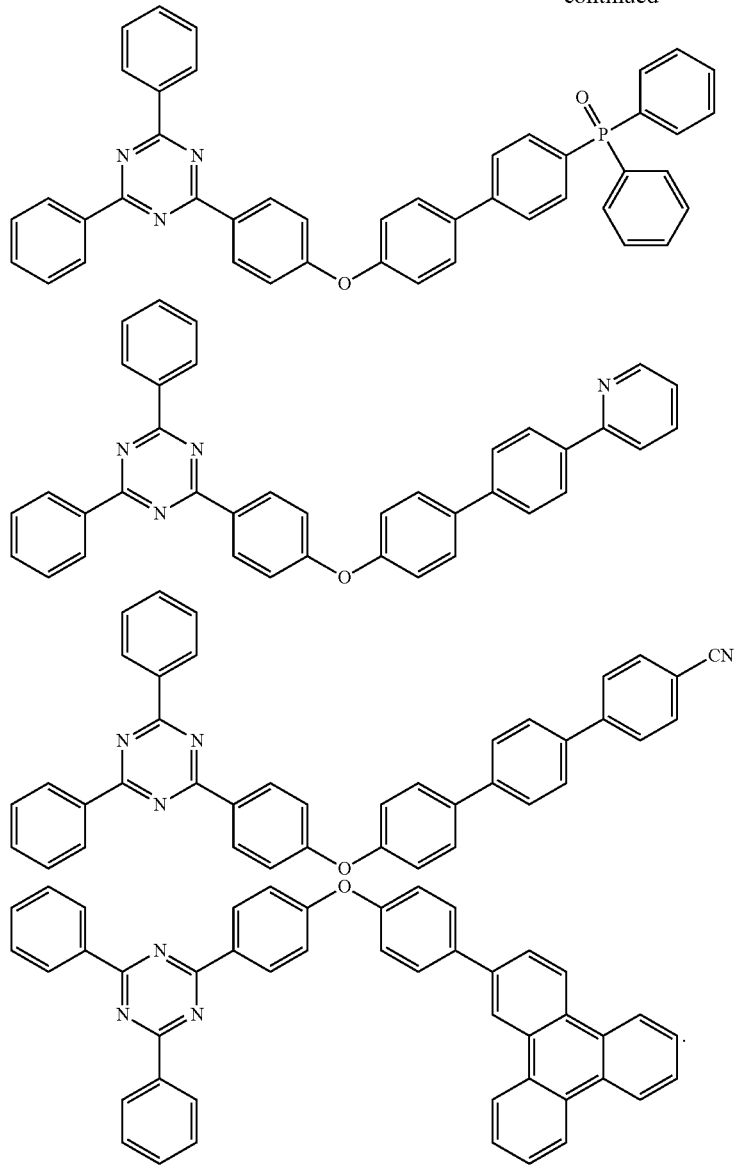

8. An organic electronic device comprising:
a first electrode;
a second electrode provided to face the first electrode; and
one or more layers of an organic material layer provided between the first electrode and the second electrode,
wherein the one or more layers of the organic material layer comprise the compound of claim 1.

9. The organic electronic device of claim 8, wherein the organic material layer comprises a hole injection layer, a hole transport layer, or a hole injection and transport layer, and at least one of the hole injection layer, the hole transport layer, or the hole injection and transport layer comprises the compound.

10. The organic electronic device of claim 8, wherein the organic material layer comprises an electron injection layer, an electron transport layer, or an electron injection and transport layer, and at least one of the electron injection layer, the electron transport layer, or the electron injection and transport layer comprises the compound.

11. The organic electronic device of claim 8, wherein the organic material layer comprises a light emitting layer, and the light emitting layer comprises the compound.

12. The organic electronic device of claim 8, further comprising:
one or two or more layers selected from an electron transport layer, an electron injection layer, an electron blocking layer, or a hole blocking layer.

13. The organic electronic device of claim 8, wherein the organic electronic device is selected from a group consisting of an organic light emitting device, an organic phosphorescent device, an organic solar cell, an organic photoconductor (OPC), and an organic transistor.

14. The organic electronic device of claim 8, wherein the organic material layer comprises a light emitting layer, and the light emitting layer comprises a compound represented by the following Chemical Formula A:

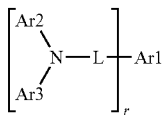

[Chemical Formula A]

in Chemical Formula A,

Ar1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L is a direct bond; a substituted or unsubstituted arylene group; or a substituted or unsubstituted heteroarylene group, Ar2 and Ar3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or optionally combine with each other to form a substituted or unsubstituted ring, r is an integer of 1 or more, and when r is 2 or more, the substituents in the parenthesis are the same as or different from each other.

15. The organic electronic device of claim 14, wherein L is a direct bond, Ar1 is a substituted or unsubstituted divalent pyrene group, Ar2 and Ar3 are the same as or different from each other, and are each independently an aryl group which is unsubstituted or substituted with a silyl group substituted with an alkyl group, and r is 2.

16. The organic electronic device of claim 8, wherein the organic material layer comprises a light emitting layer, and the light emitting layer comprises a compound represented by the following Chemical Formula B:

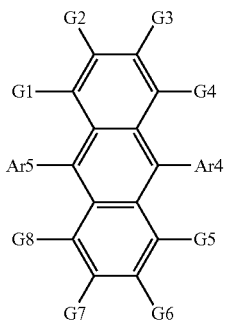

[Chemical Formula B]

in Chemical Formula B,

Ar4 and Ar5 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

17. The organic electronic device of claim 16, wherein Ar4 and Ar5 are a 2-naphthyl group, and G1 to G8 are hydrogen.

18. The organic electronic device of claim 14, wherein the light emitting layer further comprises a compound represented by the following Chemical Formula B:

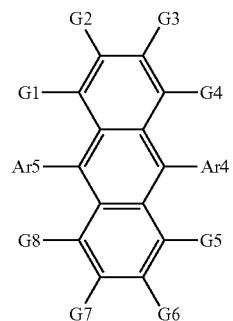

[Chemical Formula B]

in Chemical Formula B,

Ar4 and Ar5 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

* * * * *